(12) United States Patent
Miller et al.

(10) Patent No.: US 8,384,024 B2
(45) Date of Patent: Feb. 26, 2013

(54) TANDEM DIFFERENTIAL MOBILITY SPECTROMETERS AND MASS SPECTROMETER FOR ENHANCED ANALYSIS

(75) Inventors: Raanan A. Miller, Chestnut Hill, MA (US); Erkinjon G. Nazarov, Lexington, MA (US); Paul Vouros, Concord, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 25 days.

(21) Appl. No.: 12/873,493

(22) Filed: Sep. 1, 2010

(65) Prior Publication Data

US 2011/0133076 A1   Jun. 9, 2011

Related U.S. Application Data

(63) Continuation of application No. 11/823,666, filed on Jun. 28, 2007, now Pat. No. 7,812,305.

(60) Provisional application No. 60/817,663, filed on Jun. 29, 2006.

(51) Int. Cl.
*H01J 49/04* (2006.01)

(52) U.S. Cl. ........ 250/288; 250/281; 250/282; 250/283; 250/287

(58) Field of Classification Search ........... 250/281–300
See application file for complete search history.

(56) References Cited

U.S. PATENT DOCUMENTS

| | | | |
|---|---|---|---|
| 6,504,149 B2 | 1/2003 | Guevremont et al. | |
| 6,639,212 B1 | 10/2003 | Guevremont et al. | |
| 6,822,224 B2 * | 11/2004 | Guevremont | 250/287 |
| 6,940,095 B2 | 9/2005 | Hung et al. | |
| 2003/0038235 A1 * | 2/2003 | Guevremont et al. | 250/287 |
| 2003/0052263 A1 | 3/2003 | Kaufman et al. | |
| 2003/0106996 A1 | 6/2003 | Covey et al. | |
| 2003/0150986 A1 | 8/2003 | Guevremont | |
| 2003/0153087 A1 * | 8/2003 | Guevremont et al. | 436/86 |
| 2004/0004185 A9 * | 1/2004 | Guevremont et al. | 250/287 |
| 2004/0094704 A1 * | 5/2004 | Miller et al. | 250/287 |
| 2005/0051719 A1 | 3/2005 | Miller et al. | |
| 2005/0139762 A1 | 6/2005 | Miller | |
| 2005/0218320 A1 * | 10/2005 | Guevremont et al. | 250/292 |
| 2006/0060768 A1 * | 3/2006 | Kaufman et al. | 250/281 |
| 2009/0014641 A1 * | 1/2009 | Bateman et al. | 250/282 |
| 2009/0140140 A1 | 6/2009 | Raznikov et al. | |
| 2009/0173877 A1 * | 7/2009 | Bateman et al. | 250/282 |

OTHER PUBLICATIONS

Levin et al. "Characterization of Gas-Phase Molecular interactions on Differential Mobility Ion Behavior Utilizing an Electrospray Ionization-Differential Mobility-Mass Spectrometer System", Anal. Chem. Jan. 1, 2006, 78, 96-106.*

Eiceman et al. "Separation of Ions from explosives in Differential Mobility Spectrometry by Vapor-Modified Drift Gas", Analytical Chemistry, vol. 76, No. 17, Sep. 1, 2004, 4937-4944.*

Guevremont, R. et al, "Atmospheric pressure ion trapping in a tandem FAIMS-FAIMS coupled to a TOFMS: studies with electrospray generated gramicidin S ions," Journal of the American Society for Mass Spectrometry, Elsevier Science Inc., New York, NY, US., vol. 12, No. 12, Dec. 2001, pp. 1320-1330, XP004329084 (Figure 6).

* cited by examiner

*Primary Examiner* — Michael Logie

(57) ABSTRACT

The invention relates generally to systems, methods and devices for analyzing samples and, more particularly, to systems using a differential mobility spectrometer in combination with a mass analyzer to enhance the analysis process of constituents of a sample.

7 Claims, 38 Drawing Sheets

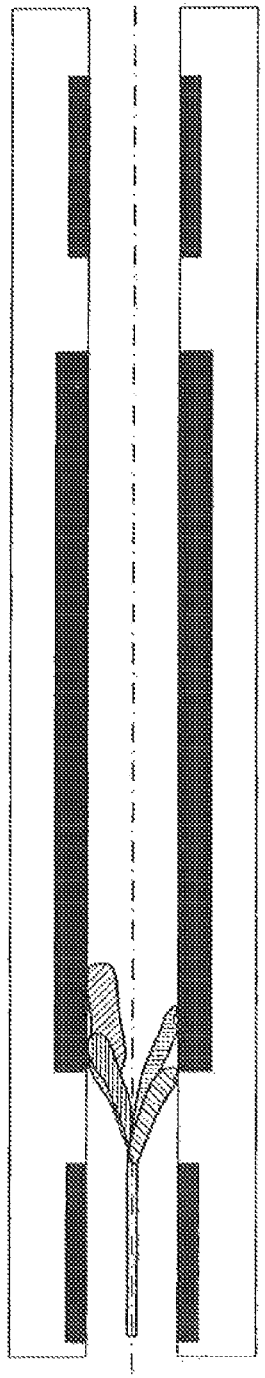
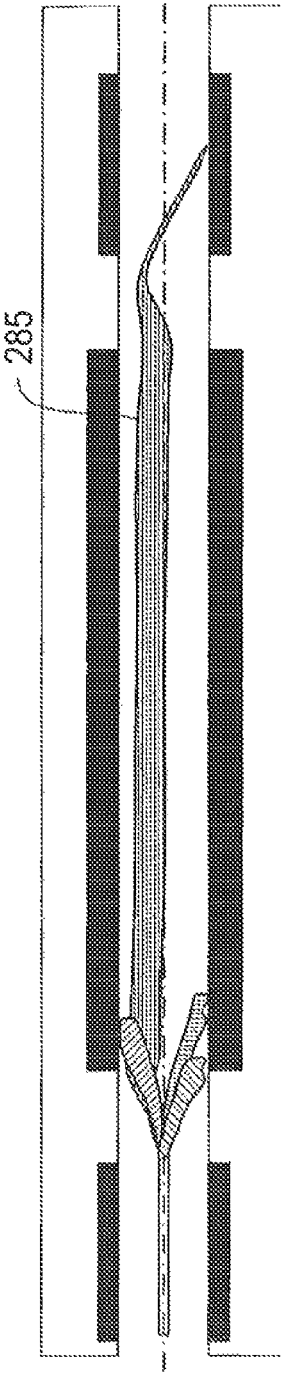
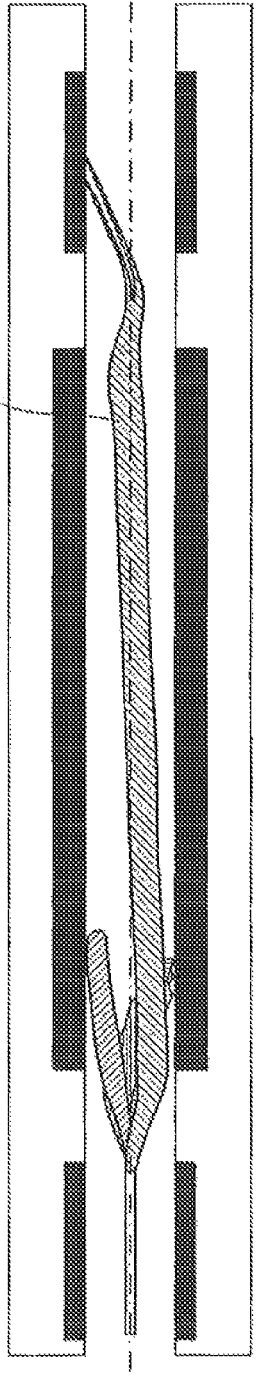
Figure 2C
Figure 2D
Figure 2E

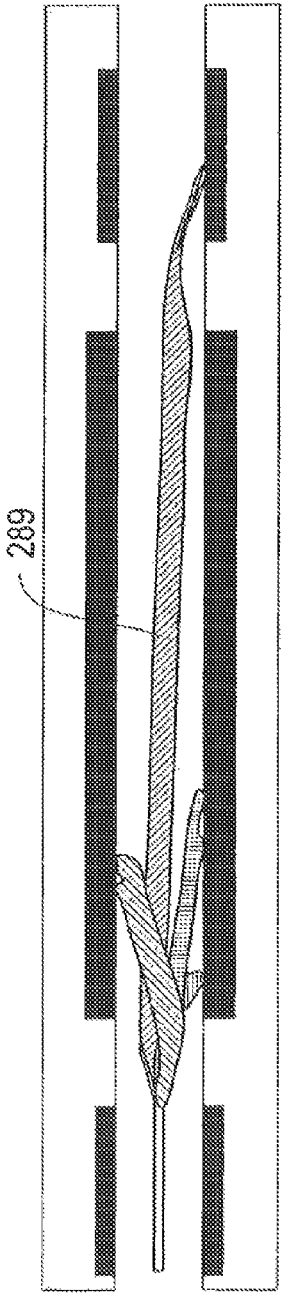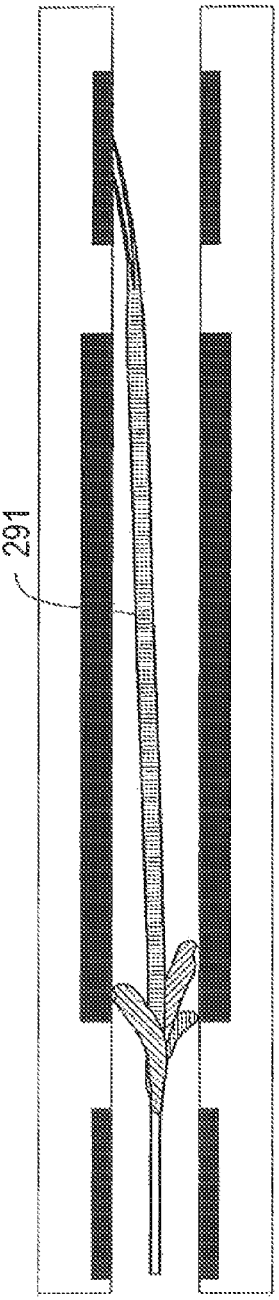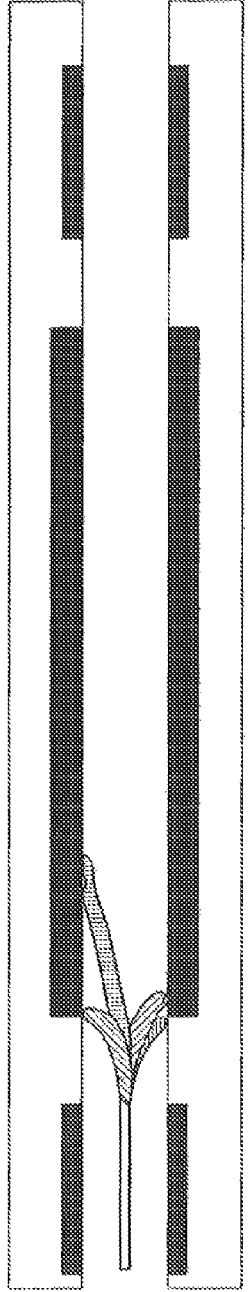

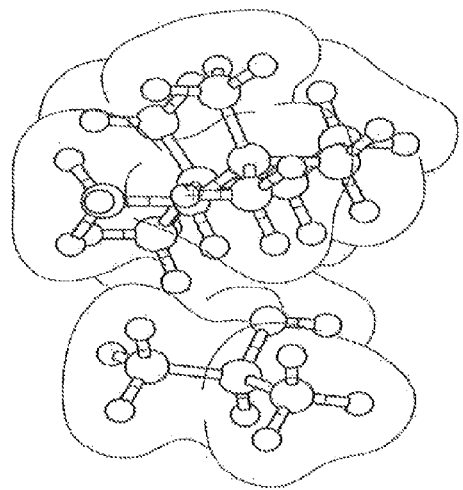
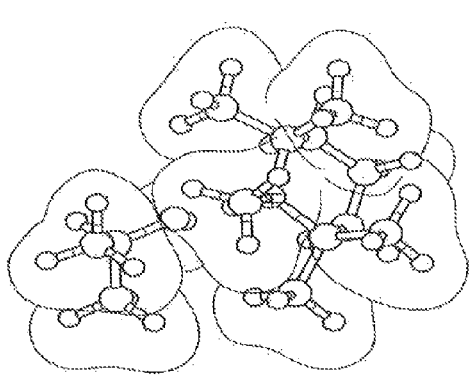
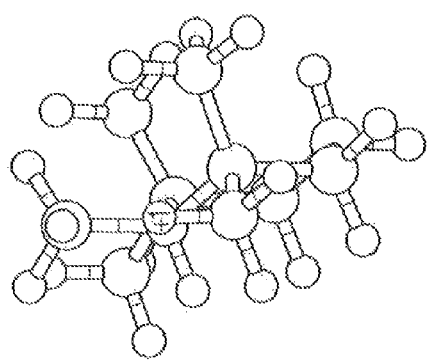
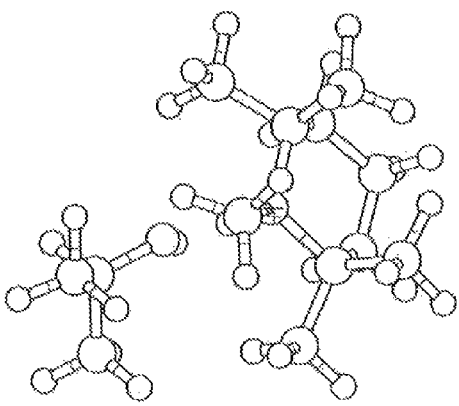
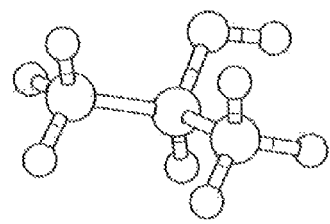
Figure 16A
Figure 16B

TANDEM DIFFERENTIAL MOBILITY SPECTROMETERS AND MASS SPECTROMETER FOR ENHANCED ANALYSIS

REFERENCE TO RELATED APPLICATIONS

This application is a continuation of U.S. patent application Ser. No. 11/823,666 filed on Jun. 28, 2007, entitled "Tandem Differential Mobility Spectrometers and Mass Spectrometer For Enhanced Analysis," which claims priority to and the benefit of: U.S. Provisional Application No. 60/817,663, filed on Jun. 29, 2006, entitled "Tandem Differential Mobility Spectrometers and Mass Spectrometer For Enhanced Analysis." This application is related to U.S. patent application Ser. No. 11/441,305, filed on May 24, 2006. The entire contents of the above referenced applications are incorporated herein by reference.

FIELD OF THE INVENTION

The invention relates generally to systems, methods and devices for analyzing samples. More particularly, in various embodiments, the invention relates to systems and related methods using tandem differential mobility spectrometers with a mass spectrometer to enhance the analysis process of constituents of a sample.

BACKGROUND

There are a number of different circumstances in which it is desirable to perform an analysis to identify and/or measure compounds in a sample. Such samples may be taken directly from the environment or they may be provided by front end specialized devices to separate or prepare compounds before analysis.

Differential Mobility Spectrometry (DMS), also referred to as High Field Asymmetric Waveform Ion Mobility Spectrometry (FAIMS) and Field Ion Spectrometry (FIS), are technologies for gas phase ion sample separation and analysis. Researchers have interfaced DMS with mass spectrometry to take advantage of the atmospheric pressure, gas phase, and continuous ion separation capabilities of DMS and the detection specificity offered by mass spectrometry.

By interfacing DMS with mass spectrometry, researchers have demonstrated benefits in numerous areas of sample analysis, including proteomics, peptide/protein conformation, pharmacokinetic, and metabolism analysis. In addition to pharmaceutical/biotech applications, DMS has been incorporated into products designed for trace level explosives detection as well as petroleum monitoring. Despite the demonstrated success of the technology, ion behavior during the differential mobility separation is not well understood for the wide range of analytes that are being analyzed by this technology. Accordingly, there is a need to enhance separation efficiency and enable predictable separation controls for a differential mobility spectrometer (DMS) interfacing with a mass spectrometer (MS).

DMS can be viewed as a spin off from conventional ion mobility spectrometry (IMS). In conventional IMS, ions are pulsed into and then pulled through a flight tube by a constant electric field. The ions interact with a bath gas in the flight tube and the interactions affect the time it takes an ion to pass through the flight tube. Unlike time of flight (TOF) MS where an ion's time through a flight tube is based solely on its mass to charge ratio (due to collision free travel in a vacuum), ions in conventional IMS are not separated in a vacuum, enabling interactions with the bath gas molecules. These interactions are specific for each analyte ion of a sample, leading to an ion separation based on more than just mass/charge ratio.

DMS is similar to conventional IMS in that the ions are separated in a bath or drift gas. However, typically, an asymmetric electric field waveform is applied to two parallel electrode plates through which the ions pass in a continuous, non-pulsed, manner. The electrical waveform consists of a high field duration of one polarity and then a low field duration of opposite polarity. The duration of the high field and weak field portions are applied such that the net voltage being applied to the electrode is zero. FIG. 1 includes an illustration 100 of the high and low voltages of opposite polarity applied to generate the asymmetric electrical waveform (identified as an Rf (field) voltage, correlating to the high voltage value) and a conceptual diagram of a DMS filter 102 where the path of an ion $M^+$ is subject to an asymmetric field resulting from the asymmetric waveform. As can be seen in illustration 100, after one cycle of the waveform, the net voltage applied to the DMS filter electrode is zero.

However, the ion's mobility in this asymmetric electric field demonstrates a net movement towards the bottom electrode plate of the DMS filter 102. This example shows that, in DMS, an ion's mobility is not proportional under the influence of a low electric field compared to a high electric field. Since an ion may experience a net mobility towards one of the electrode plates during its travel between the plates, a compensation voltage (Vc) is applied to maintain a safe trajectory for the ion through the DMS filter 102 plates without striking them. The ions are passed between the two electrodes by either being pushed through with a pressurized gas flow upstream of the electrode plates or pulled through by a pump downstream from the electrodes.

In conventional IMS, as well as DMS, ions are separated in a gas at pressures sufficient for the occurrence of collisions between ions and the neutral gas molecules. The smaller the ion, the fewer collisions it will experience as it is pulled through the drift gas. Because of this, an ion's cross sectional area may play a significant role in it's mobility through the drift gas. As shown in FIG. 1, an ion's mobility is not proportional under the influence of a low electric field compared to a high electric field. This difference in mobility may be related to clustering/de-clustering reactions taking place as an ion experiences the weak and strong electric fields. An ion experiences clustering with neutral molecules in the drift gas during the weak field portion of the waveform, resulting in an increased cross sectional area. During the strong field portion of the waveform, the cluster may be dissociated, reducing the ion's cross sectional area.

Recently, DMS research has focused on understanding the gas phase molecular interactions taking place and how they influence an ions' mobility in the DMS sensor. Existing FAIMS-MS systems have demonstrated DMS separation between certain monomer ions and non-covalently bound cluster/dimer ions. These systems have provided evidence that non-covalently bound dimer/cluster ions can have different differential mobility behavior from their monomer counterparts. This indicates that the cluster/dimer ions were created prior to entering the DMS sensor, and were not dissociated back to their monomer counterparts upon entering the asymmetric electric field of the sensor and/or DMS filter. The formation of these cluster/dimer ions may effect the detection of ions of interest within a sample analysis system such as a DMS-MS. Accordingly, there is a need for compensating for and/or accounting for the presence of cluster/dimer ions and other compounds that result from gas phase molecular interactions in a sample analysis system to enhance the accuracy and resolution of these systems.

Existing DMS-based systems have analyzed sample ions through the use of various vapor modified drift gases for which the proposed process is via clustering/de-clustering interactions between a monomer analyte ion and neutral drift gas modifier/dopant molecule in which the analyte ion's effective cross sectional area is changed. While existing DMS-based systems have shown a change in an analyte ion's differential mobility behavior through the use of drift gas modifiers or dopants, there remains a need for a clear model with regards to the underlying interactions between the modifier and analyte, and the mechanism(s) by which those interactions change an analyte ion's differential mobility behavior.

By employing a DMS as a pre-filter to a MS, existing FAIMS-MS and/or DMS-MS systems have increased the detection sensitivity and resolution of sample analysis by reducing the amount of contaminants or unwanted particles that interact with the ions of interest in a MS. Electrospray ionization (ESI) has been employed with FAIMS-MS to facilitate the analysis of certain liquid samples. However, direct infusion of samples using ESI has typically been avoided, particularly with complex samples, because of problems with competitive ion suppression. Competitive ion suppression has limited the accuracy of existing ESI-FAIMS-MS systems by reducing the quantity of ions of interest that are eventually detected in the MS. Because of ion suppression, analyte separation techniques prior to ESI, such as Liquid Chromatography (LC), Gas Chromatography (GC), and Capillary Electrophoresis (CE), have been utilized to minimize ion suppression effects. Accordingly, there is a need for providing an ESI-DMS-MS system having enhanced capabilities that reduce competitive ion suppression and/or compensate for the effects of such suppression when quantizing certain ion species.

It has long been known that the conformational structure of a protein has an effect on a wide spectrum of its biological activities including the control of signaling pathways, biosynthesis, its interaction with binding ligands, the transport of drugs and other chemical agents. In addition to equilibrium related intermediates, there has also been interest in the so-called transient folding states which represent a highly dynamic system that may play an important role in biological functions. Traditionally, nuclear magnetic resonance (NMR) has been the common instrumental technique for monitoring these physical transformations in solution. However, the development of electrospray ionization (ESI) techniques has introduced new opportunities for studying protein conformational features by mass spectrometry. Since conformational change effectively reflects a change in the volume of space occupied by the protein, and thus its cross sectional area, ion mobility mass spectrometry provides an attractive complementary approach for the study of such processes. Two basic mass spectrometric approaches are typically used to examine variations in the conformational structure of a protein:

(i) shift of the charge-state distribution pattern during electrospray ionization and, (ii) hydrogen/deuterium (H/D) exchange.

For example, it has long been known that, upon electrospray ionization, a folded (spherically shaped) protein is able to accommodate fewer positive charges on its surface due to increased coulombic repulsion and/or due to reduced exposure of possible protonation sites of basic amino acids. Significantly, if two conformations co-exist in the same solution, the ESI spectrum may exhibit a bimodal pattern representative of the isomeric mixture. In turn, the folding status is also known to influence the exchange of highly labile (amino or carboxylic) hydrogens with deuterium made available through the solvent medium, and the resulting mass increments are used to, at least qualitatively, establish the occurrence of conformational changes.

In general, simple H/D exchange is not sufficient to identify specific amino acids in the sequence of the protein that may have undergone exchange without enzymatic digestion of the protein and amino acid sequencing of the resulting peptides. For highly labile hydrogens, back exchange is also a major concern. However, H/D may provide some guide toward the identification of protected regions in conformers. It has been demonstrated that the two conformers of DvHY64A, a mutated form of Cytochrome C553, exhibited different levels of H/D exchange indicating that there is a sub-population of amide hydrogens which remain shielded because the folded forms of the two conformers are perfectly stable.

There are several examples of the use of the two aforementioned approaches in conjunction with combined IMS-MS to study protein conformations (See Valentine, et al., *H/D Exchange Levels of Shape-Resolved Cytochrome c Conformers in the Gas Phase*, J. Am. Chem. Soc., 1997, 119, 3558-3566). Valentine et al. showed that variation of the voltage at which protein ions are injected into the drift tube of an IMS resulted in the formation of different conformers. Lower deuterium incorporation was observed for the charge states of compact conformers as opposed to the unfolded forms and, consistent with the discussion presented above, an analogous trend was observed for the respective charge state distributions. More recently, a tandem IMS-IMS-MS combination has been proposed in which the first IMS selects specific ions which are subjected to collision activated dissociation (CAD) and the fragments transferred to the second drift tube for further separation and CAD followed by MS analysis. (See Koeniger et al., *An IMS-IMS Analogue of MS-MS*, 2006, 78, 4161-4174).

In addition to conventional drift tube IMS, the capability of FAIMS or DMS for the study of protein conformations has been explored. Conformers of ubiquitin were generated in solution at set pH values and introduced into the FAIMS-MS system by electrospray ionization. Separation in the FAIMS analyzer was found to be dependent on the structure (conformation) of a given protein ion and several conformers of the same charge state were often resolved in the DMS. Moreover, samples sprayed from solutions of different pH yielded different charge distribution patterns as well as different conformers as indicated from the shifts in the Vc spectra. Of particular significance was the conformer-specific distribution of $Na^+$ and other adduct ions, leading to the conclusion that the addition of "spectator" ions to form protein-spectator adducts may lead to information about the conformational structure of the protein.

Related research has investigated the electrospray mass spectra of the amyloidogenic protein $\beta_2$-microglobulin ($\beta_2$m) using a FAIMS-MS combination over a range of several pH units. As expected, at each pH, a different charge distribution envelope was observed. However, when the different charge states were further screened by combining the Vc and MS spectra, it was determined that each charge state reflected the presence of multiple conformers in the sprayed solution which could then be resolved in the FAIMS filter. (See Borysik et al., *Separation of $\beta_2$-microglobulin conformers by high-field asymmetric waveform ion mobility mass spectrom-*

*etry (FAIMS) coupled to electrospray ionization mass spectrometry*, RCMS, 2004, 18, 2229-2234).

SUMMARY

The invention, in various embodiments, addresses deficiencies in the prior art by providing systems, methods and devices for detecting, identifying, measuring and/or analyzing (collectively "analyzing") constituents in a sample. More particularly, the invention enables the isolation and manipulation and detection of conformations of particular ion species using a tandem DMS configuration in combination with a mass spectrometer.

In one aspect, a sample analysis system includes a first DMS analyzer for filtering or passing through a select ion species. A second DMS analyzer then receives the ion species from the first DMS analyzer. The second DMS analyzer manipulates the conformation of the ion species and passes through a conformer of the ion species. A controller may be employed to controlling at least one condition of the second DMS analyzer to manipulate the conformation of the ion species.

In one configuration, a detector for receives and detects the conformer of the ion species delivered from the second DMS analyzer. In one feature, at least one condition includes at least one of an amount of a ligand and a type of ligand. A data store may be employed for storing a library of ligands while the controller may be configured to control the introduction of an amount of a ligand listed in the library. The controller may introduce each of a set of ligands into the second DMS analyzer to adjust the conformation of the ion species in relation to each ligand. The controller may introduce each ligand sequentially.

In another configuration, at least one condition includes temperature of a flow path through the second DMS analyzer. The controller may adjust at least one of the magnitude and frequency of an asymmetric field through which the ion species flow to adjust the temperature of the ions and, thereby, adjust the conformation of the ion species.

In a further configuration, at least one condition may includes at least one of an amount of dopant, a type of dopant, pressure, and flow rate. In one feature, manipulating includes creating at least one new conformer. In one configuration, the detector includes a mass spectrometer. Also, the mass spectrometer may be a time-of-flight mass spectrometer.

The present invention addresses various deficiencies in the prior by providing, at least the following advantageous features:

- Ultra fast (millisecond time scale) separation and selection of different ionic species.
- Ability to rapidly set or scan the ion RF separation voltage to modulate protein conformation, and consequently to evaluate its affinity and activity. The kinetics of protein conformational change can be visualized by observing two dimensional plots, i.e., changes in DMS spectra under the effect of RF voltage (dispersion plots).
- Small overall DMS-DMS system size (3 cm×2 cm×1 cm) and the potential for further miniaturization.
- Modulation of protein conformation via the use of electric fields.
- Operation in a continuous as opposed to pulsed mode for specific ion filtration and subsequent screening of selected ion species.
- Ability to perform separations of individual protein conformers in milliseconds, effectively in real time.
- Quantification of selected analytes by rapid scanning (e.g., less than about 1 second) of compensation voltage in combination with MS detection.
- Capability for simultaneous separation (or isolation) in real time of both positive and negative ions in different parts of the DMS.
- Rapid modulation of protein conformation upon interaction with chemical reagents (modifiers) and detection of protein conformation in the gas phase, which may be important for understanding and characterizing the kinetics of how protein conformations change.
- Operation of the DMS filter at atmospheric pressure allows a more accurate simulation of condensed phase conditions and, thereby, the acquisition of mass spectrometric data that more closely reflect the function of proteins in their natural (physiological) environment.

In effect, in certain aspects, the inventive systems and methods are capable of rapidly visualizing in both a temporal and a spatial domain, the conformational changes and chemical interactions of the different forms of a protein with selected chemical species. This rapid analysis is enabled by the small size of the DMS filters, e.g. about the size of a U.S. 25-cent coin, which enables a short sample residence. Furthermore, the DMS filter and subsequently, DMS-DMS systems can be readily incorporated into virtually any types of mass spectrometers or adapted for field use in miniaturized systems.

BRIEF DESCRIPTION OF THE DRAWINGS

These and other features and advantages of the invention will be more fully understood by the following illustrative description with reference to the appended drawings, in which like elements are labeled with like reference designations and which may not be to scale.

FIGS. 2C-2H shows the modeled flow of ions through a DMS filter depending on the compensation voltage Vc setting according to an illustrative embodiment of the invention.

FIG. 16A is an exemplary view of a protonated pentamethyl-piperidine complex with and without an associated electron density cloud.

FIG. 16B is an exemplary view of a neutral 2-propanol complex with and without an associated electron density cloud.

ILLUSTRATIVE DESCRIPTION

The invention, in various embodiments, provides systems, methods and devices for detecting, identifying, measuring and analyzing (collectively "analyzing") constituents in a sample. The samples and constituents may include any material; chemical or biological, organic or inorganic. In particular illustrative embodiments, the invention is directed to an ESI-DMS-MS combination system, which employs enhanced modeling techniques to compensate for effects of competitive ion suppression and, thereby, provide better sample resolution and quantization.

In one embodiment, Electrospray ionization (ESI) combined with Differential Mobility Spectrometry (DMS) and Mass Spectrometry (MS) is utilized for rapid analyte quantization of a directly infused ESI sample. In another embodiment, the ESI-DMS-MS system includes a micromachined, nanomachined, and/or nanoESI-DMS-MS platform for rapid quantitative analysis.

Figure 2A:
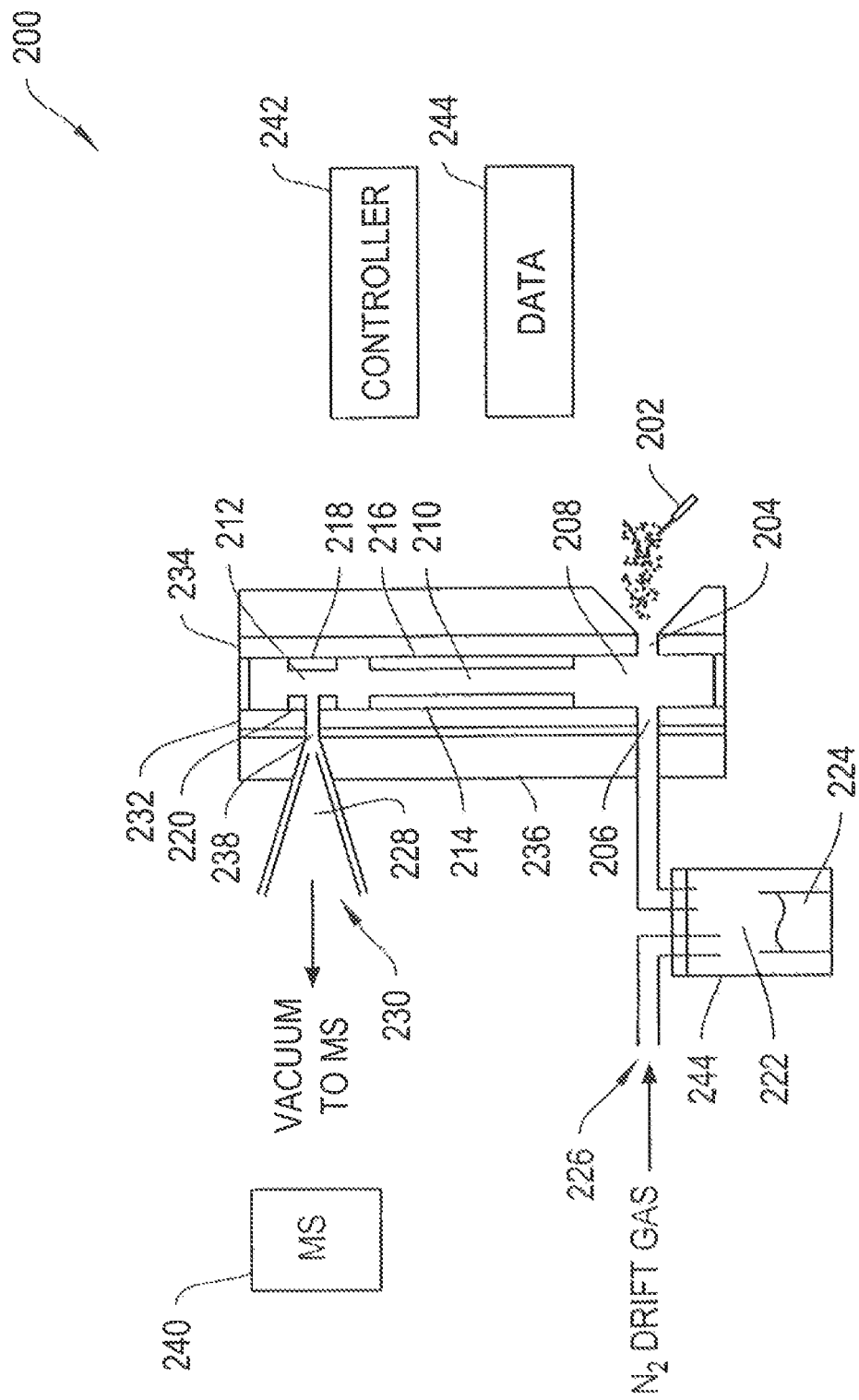
FIG. 2A is a conceptual diagram of a ESI-DMS-MS system according to an illustrative embodiment of the invention.

FIG. 2A is a conceptual diagram of a ESI-DMS-MS system 200 according to an illustrative embodiment of the invention. The ESI-DMS-MS system 200 includes a nanospray source 202, a flow path 208, a DMS filter 210, a DMS detector 212, a MS analyzer 240, an MS inlet cone 228, a drift gas inlet 226, a mixing region 222, a vial 244, a dopant reservoir 224, a DMS analyzer inlet 206, an ESI inlet 204, a DMS analyzer housing 236, DMS filter electrodes 214 and 216, DMS ion detector plates 218 and 220, substrates 232 and 234, electronic controller 242, and orifice 238. The DMS filter 210 may include a Sionex SDP-1 modified sensor, while the MS analyzer 240 may include a Micromass ZQ detector. The electronic controller 242 may include a microprocessor for regulating one or more conditions of the ESI source 202, the flow path 208, the DMS filter 210, the DMS detector 212, the mixing region 222, and the MS analyzer 240.

For example, the controller 242 may adjust the compensation voltage (Vc) applied to at least one of the filter electrodes 214 and 216 or a condition of a time-varying voltage waveform (Vrf) to the filter electrodes 214 and 216 to effect ion separation in the DMS filter 210. A condition of the filter 210 may include the asymmetry, duty cycle, magnitude, frequency of the waveform (See FIG. 1). The controller 242 may regulate the flow of $N_2$ gas through the inlet 226, the mixing period and/or amount within region 222, and the amount and/or flow rate of mixed or unmixed gas that is introduced via inlet 206 into the flow path 208. The controller 242 may control the operation of the ESI source 202. The controller 242 may further control the operation of the MS analyzer 240.

The controller 242 may interface with a data store 244 which may include a database, list, array, or like data structure containing information, such as condition information, associated with system 200.

In one embodiment, the ESI-DMS-MS system 200 is contained within a single integrated circuit (IC) package. In another embodiment, the ESI-DMS is included in an IC package that includes an interface portion capable of detachable connection to a standard MS analyzer 240.

In operation, a sample S is introduced into the flow path 208 via the ESI inlet 204 from the ESI source 202. The sample S may originally be in a liquid form until processed at the ESI source 202 and injected into the flow path 208 as a spray of ions. The ions are then transported by a drift and/or carrier gas, introduced via inlet 206, to the DMS filter 210. While passing through the DMS filter 210, the ions are subject to a time-varying electric field and compensation field that separates and/or allows certain ion species to pass through the filter 210 while other ions are directed toward one of the filter electrodes 214 or 216 and neutralized. A portion of the ions that reach the detector 212 may be detected by one or both of the detector electrodes 218 and 220. In one embodiment, certain ions are directed through the orifice 238, embedded in electrode 220 to the MS analyzer 240 via the inlet cone 228 for mass spectrometric detection. The controller 242 may process either or both of the detected spectra from the DMS detector 212 and the MS analyzer 240. The controller 242 may include a processor for executing software, firmware, and/or hardware programs that control a portion of the components and/or operations of the system 200.

The carrier gas may include pure nitrogen, some other gas, or a gas including one or more dopants. The controller 242 may selectively adjust the dopant concentration within the carrier gas depending on the ion species of interest and/or to be detected. The controller 242 may include a data store, database, memory storage, grouping, and/or list of condition information associated with known ion species. The condition information, for example, may include compensation voltage settings and/or peak ranges of the DMS filter 210 associated with at least ion species and related MS analyzer 240 spectra to enable identification of certain ion species.

In one embodiment, the combined fast compensation voltage (Vc) scanning capability of the DMS filter 210 (e.g., in milliseconds) and the selective mass-to-charge (m/z) ion signal generation of the MS analyzer 240, enable the rapid generation of a selected ion DMS spectra with which the DMS peak area of the selected m/z value is integrated and the peak apex compensation voltage Vc is used for accurate analyte identification, similar to how retention time is used for liquid or gas chromatography. Since ESI can potentially produce isobaric background ions of the same m/z as an analyte of interest, the use of the DMS peak apex compensation voltage for matching with that of a reference standard enables accurate identification of an analyte of interest from that of a background ion signal which is particularly important at trace quantization levels.

This approach to analyte analysis enables rapid quantization of multiple analytes of interest from a single sample. The limiting factor to the speed of analysis time is the scanning speed of the MS analyzer 240, which needs to be fast enough to enable the collection of sufficient data points across the DMS filter 210 Vc spectra range. In one embodiment, the MS analyzer 240 includes of a time-of-flight mass spectrometer having fast mass scanning capabilities. Using the time-of-flight MS analyzer 240, it is reasonable to generate a DMS spectra for each sample in the low seconds (1-5 sec.) time frame for a large m/z window. The larger the m/z window, the greater the number of selected ion DMS spectra which are extracted from a single Vc scan, enabling the quantization of multiple analytes from a single sample Vc scan (DMS filter 210 spectra).

In certain embodiments, a slower scanning MS analyzers 240, such as a quadrupole mass spectrometer, is employed. Thus, a single ion monitoring mode may be required to maintain the mass scan speeds necessary for the low second Vc scan times.

In other embodiments, the combined rapid Vc scanning of the DMS filter 210, the selective m/z ion signal detection of MS analyzer 240, the DMS filter 210 peak apex compensation voltage matching, and the use of direct sample infusion to the ESI source 202, enable an ideal platform for ultra high-throughput analysis. The use of a multi-sample, automated, direct infusion nanoESI source 202, such as the Nanomate from Advion Biosciences Inc., combined with the DMS-MS separation, detection, and quantization platform of system 200, encompasses the type of system capable of performing ultra high-throughput analysis for numerous applications. With regards to speed of analysis, the system 200 enables significantly faster sample analysis times compared to other high-throughput approaches such as fast-LC, e.g., less than about 5 seconds, less than about 4 seconds, less than about 3 seconds, less than about 2 seconds, and less than about 1 second.

While Flow Injection Analysis (FIA) and direct sample infusion without the use of DMS are capable of achieving sample analysis times, within an order of magnitude greater than 1-5 seconds, FIA and direct sample infusion do not provide any ion separation prior to the MS analyzer 240. Thus, these systems cannot provide the analyte specificity and quantitative accuracy expected from the ESI-DMS-MS system 200. Both FIA and direct sample infusion have been combined with the use of FAIMS-MS, however they have not been used to rapidly generate selected ion DMS spectra via rapid Vc scanning, and then utilize the DMS spectra peak area for quantitative analysis. The present approach advantageously improves sample analysis time, sensitivity, specificity, and quantitative accuracy, compared to the other FAIMS-MS approaches. Preliminary data indicates that the process of DMS Vc scanning may provide an absolute increase in ion signal (via ion focusing or some other process) compared to the mass spectra ion signal alone.

Direct infusion of samples with ESI has typically been avoided, particularly with complex samples, because of problems with competitive ion suppression. Because of ion suppression, analyte separation techniques prior to ESI, such as Liquid Chromatography (LC), Gas Chromatography (GC), and Capillary Electrophoresis (CE), have been utilized to minimize ion suppression effects. However, with the recent advances in low flow nano-electrospray ionization, ion suppression can be minimized, and possibly eliminated for many samples. In one embodiment, the ESI-DMS-MS system 200 employs a nano-electrospray source 202 to minimize ion suppression, enabling nanoESI-DMS-MS analysis platform and/or system 200 to revolutionize sample analysis for a wide spectrum of applications, such as quantitative and qualitative analysis requiring faster throughput.

One of the primary analytical techniques being utilized in a high-throughput manner for various applications is LC-MS. In another embodiment, the nanoESI-DMS-MS analysis system 200 is ideally suited to replace a LC-MS for many of the current high-throughput applications, such as drug-discovery, ADME (Adsorption, Distribution, Metabolism, Excretion), biomarker/diagnostic screening, pharmacokinetic/pharmacodynamic, and drug-protein binding. In addition, numerous drug product quality control based assays for process control, product release, and stability testing may benefit from the ESI-DMS-MS system 200. Unlike LC based instruments, where each instrument can typically only run a single method between column and mobile phase changes, the nanoESI-DMS-MS analysis system 200 is capable of instantaneous and/or concurrent automated switching between optimized DMS filter 210 settings for different analytes.

In a further embodiment, a slightly different approach to operating the system 200, a specific MS analyzer 240 ion signal is used to generate an ion specific DMS dispersion plot (Rf vs. Vc vs. ion signal) instead of the DMS detector 212 spectra. In one embodiment, an ion specific DMS dispersion plot may require more analysis time to generate than the DMS spectra, but provides a greater degree of analyte specificity due to analyte compensation voltage matching across multiple time-varying Vrf voltages. The generation of an ion specific DMS dispersion plots may be valuable for numerous applications where an increased degree of analyte specificity is desired.

Figure 2B:
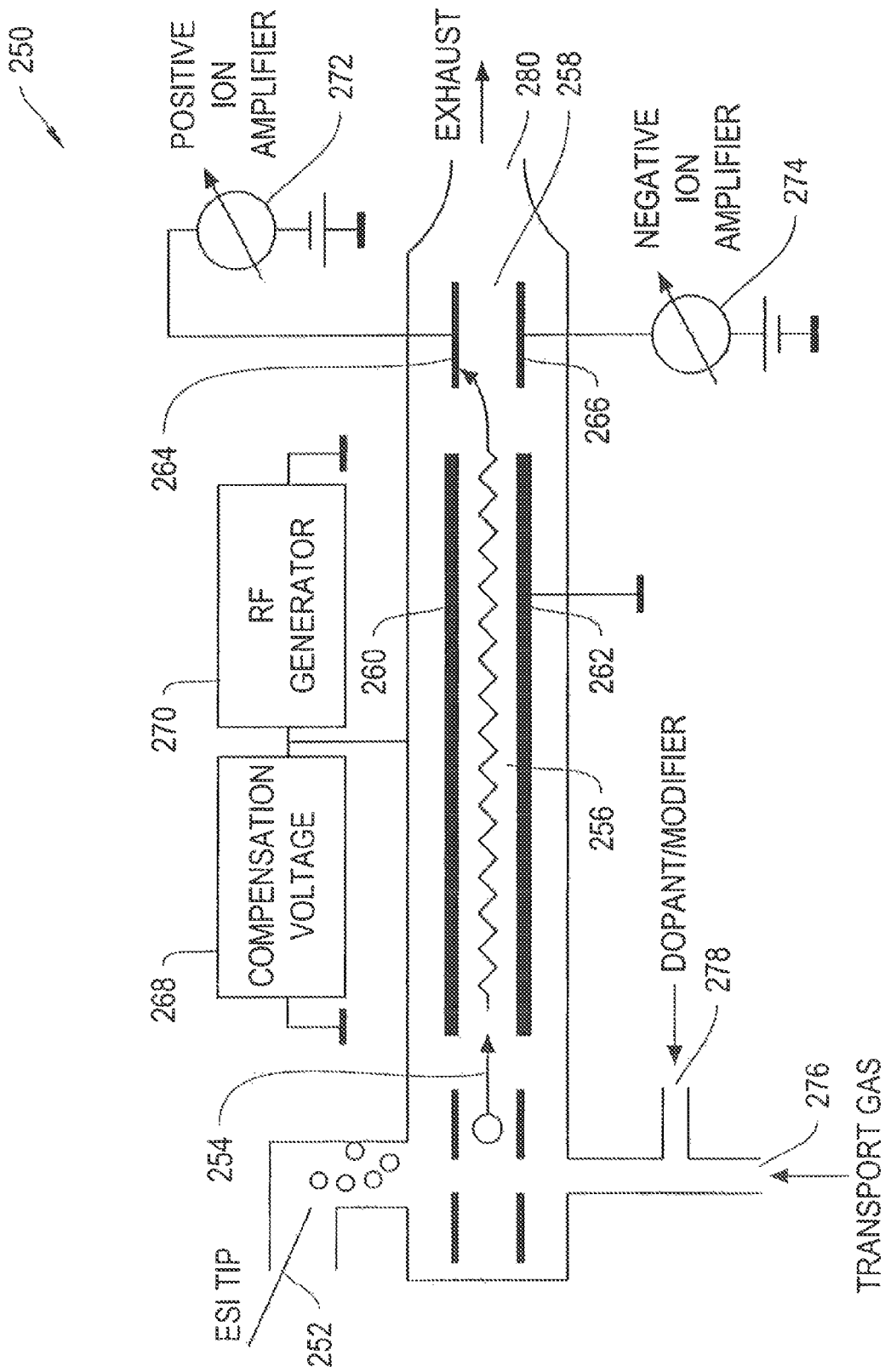
FIG. 2B is a conceptual diagram of a ESI-DMS system according to an illustrative embodiment of the invention.

FIG. 2B is a conceptual diagram of a ESI-DMS system 250 according to an illustrative embodiment of the invention. The ESI-DMS system 250 includes an electrospray ionization source 252, a flow path 254, a DMS filter 256, a DMS detector 258, DMS filter electrodes 260 and 262, DMS ion detector plates 264 and 266, compensation voltage source 268, RF voltage generator 270, positive and negative ion amplifiers 272 and 274 respectively, transport gas inlet 276, dopant inlet 278, and exhaust 280. An electronic controller, such as controller 242 may include a microprocessor for regulating one or more conditions of the ESI source 252, the flow path 254, the DMS filter 256, the DMS detector 258, the dopant inlet 278. The exhaust 280 may be in communication with one or more mass spectrometers such as MS 240.

In operation, ions are produced at the ESI source 252 and mix with the transport gas from the inlet 276 and/or one or more dopants from the dopant inlet 278. The ions flow along the flow path 254 and through the DMS filter 256. Depending on the Vc setting from the source 268 and the Vrf setting from the generator 270, selected ion species are allowed to pass through the DMS filter 256 between the fields generated by the electrodes 260 and 262. The DMS detector 258 may detect one or both positive and negative ions via detector electrodes 264 and 266 respectively. The amplifiers 272 and 274 may amplify the detected positive and negative ion intensities detected at electrodes 264 and 266, and then provide such signal information to a processor and/or controller for further processing, analysis, and/or data storage. The controller 242, for example, may receive the ion intensity signals from the amplifiers 272 and 274 for processing and analysis, and use a data store such as data store 244 to store or retrieve certain processing information.

The ESI-DMS system 250 has capabilities for trace level analysis by rapid (1-5 second) scan of the Vc spectra in combination with a mass spectrometer such as MS 240. In certain embodiments, an asymmetric electric field waveform is applied to the two parallel conductive plates, e.g., electrodes 260 and 262, enabling the ions to pass through in a continuous, non pulsed, manner. In one embodiment, the electrical waveform consists of high field duration (up to 30,000 V/cm) of one polarity and then low field duration (less than 1000 V/cm) of opposite polarity, such that the integrated voltage-time being applied to the electrode 260 is zero.

In one embodiment, the ESI-DMS system 250 separates ions at ambient pressure, based on the non-linear dependence of the mobility coefficient K(E) on the applied electric field according to equation (1).

$$K(E)=K(0)[1+\alpha_2(E/N)^2+\alpha_4(E/N)^4+\ldots]= K(0)[1+\alpha(E/N)] \quad (1)$$

where: K(0) is the mobility coefficient for low E conditions;
the $\alpha_i$ parameters show the dependence of K on the electric field, and N is density of gas molecules.

Figure 1:
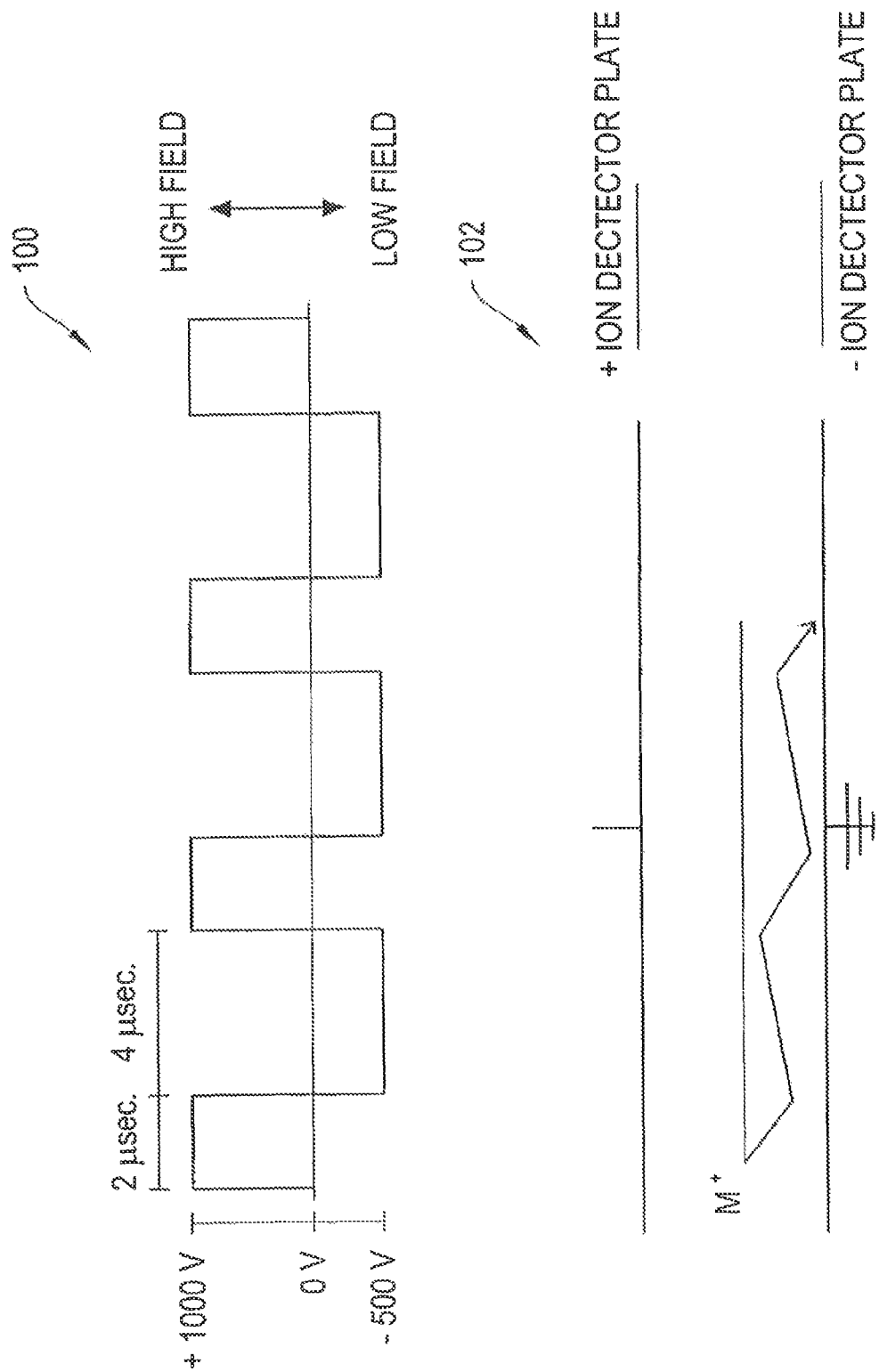
FIG. 1 includes an illustration of the high and low voltages of opposite polarity applied to generate the asymmetric electrical waveform and a conceptual diagram of a DMS filter where the path of an ion $M^+$ is subject to an asymmetric field resulting from the asymmetric waveform.

Non-symmetric waveform RF impulses applied to the electrodes cause an oscillatory motion of the ions transverse to the flow as shown in FIG. 1. This oscillatory motion draws ions towards one or the other electrode 260 or 262 with different velocity, v(t)=K(E)*E(t), in each portion of the waveform. Ions can pass through the narrow channel between the electrodes 260 and 262 and subsequently be detected only if the net displacement caused by the high and low voltage portions of the non-symmetric RF pulses approaches zero. If an ion has some net lateral displacement, i.e. different $\alpha$ parameters for the high and low field periods, after a certain time it will collide with one of the electrodes 260 or 262 and not pass through the DMS filter 256.

The lateral displacement of any ion species through the analytical gap between electrodes 260 and 262 can be adjusted to zero by imposing an additional DC potential or compensation voltage Vc, which compensates the ions' lateral displacements under effect of the RF voltages Vrf. The Vc may be scanned to record a DMS spectrum. In certain embodiments, both positive and negative ions are carried together through the analytical gap of DMS filter 256 by a transport gas and can therefore be detected concurrently at the detector 258 as the Vc is scanned. In one embodiment, the detector ion current, as a function of Vc, provides spectral information characteristic of ions having different $\alpha$ values. Since the dependence of $\alpha$ on the RF amplitude is non-linear, the amplitude is one more variable or signal characteristic that may also be scanned to provide additional information.

FIGS. 2C-2H show the modeled flow of ions through a DMS filter such as DMS filter 256 depending on the compensation voltage Vc setting according to an illustrative embodiment of the invention. FIGS. 2C-2H show trajectories simulations for four ion species which were obtained by using the Sionex microDMX™ software, manufactured by the Sionex Corporation of Bedford, Mass. FIGS. 2C-2H also illustrate the bimodal operation of the DMS: a) simultaneously filtration of positive and negative ions species, just by tuning Vc specific values; and b) ion species screening mode operation when $V_C$ is scanned. In one example, four ions species are formed where all ions have different alpha parameters and charges (e.g., two species are positive and two species are negative polarity ions).

FIG. 2C includes a plot 282 that shows the ion flow through a DMS filter when Vc=−27.8V which locks and causes all ion species to be filtered and/or neutralized by the filter electrodes. Thus, no ions pass through the filter for detection. FIG. 2D includes plot 284 that shows the ion flow through a DMS filter when Vc=−25.80V which provides filtration and detection of positive ions 285 having the highest alpha parameter which are recorded at the positive ion detector. FIG. 2E includes plot 286 that shows the ion flow through a DMS filter when Vc=−21.00V which provides filtration and detection of the negative ions species 287. The negative ion species 287 are detected at the negative ion detector. FIG. 2F includes plot 288 that shows the ion flow through a DMS filter when Vc=−16.60V provides filtration of positive ion species 289 having a lower alpha parameter. FIG. 2G includes plot 290 that shows the ion flow through a DMS filter when Vc=−9.60V which provides filtration of negative ion species 291 having the lowest alpha parameter. The negative ion species 291 are then detected at the negative ion detector. FIG. 2H includes plot 292 that shows the ion flow through a DMS filter when Vc=−0.2 V which results in the lock out, neutralization, or filtering out of all ions species.

Figure 3:
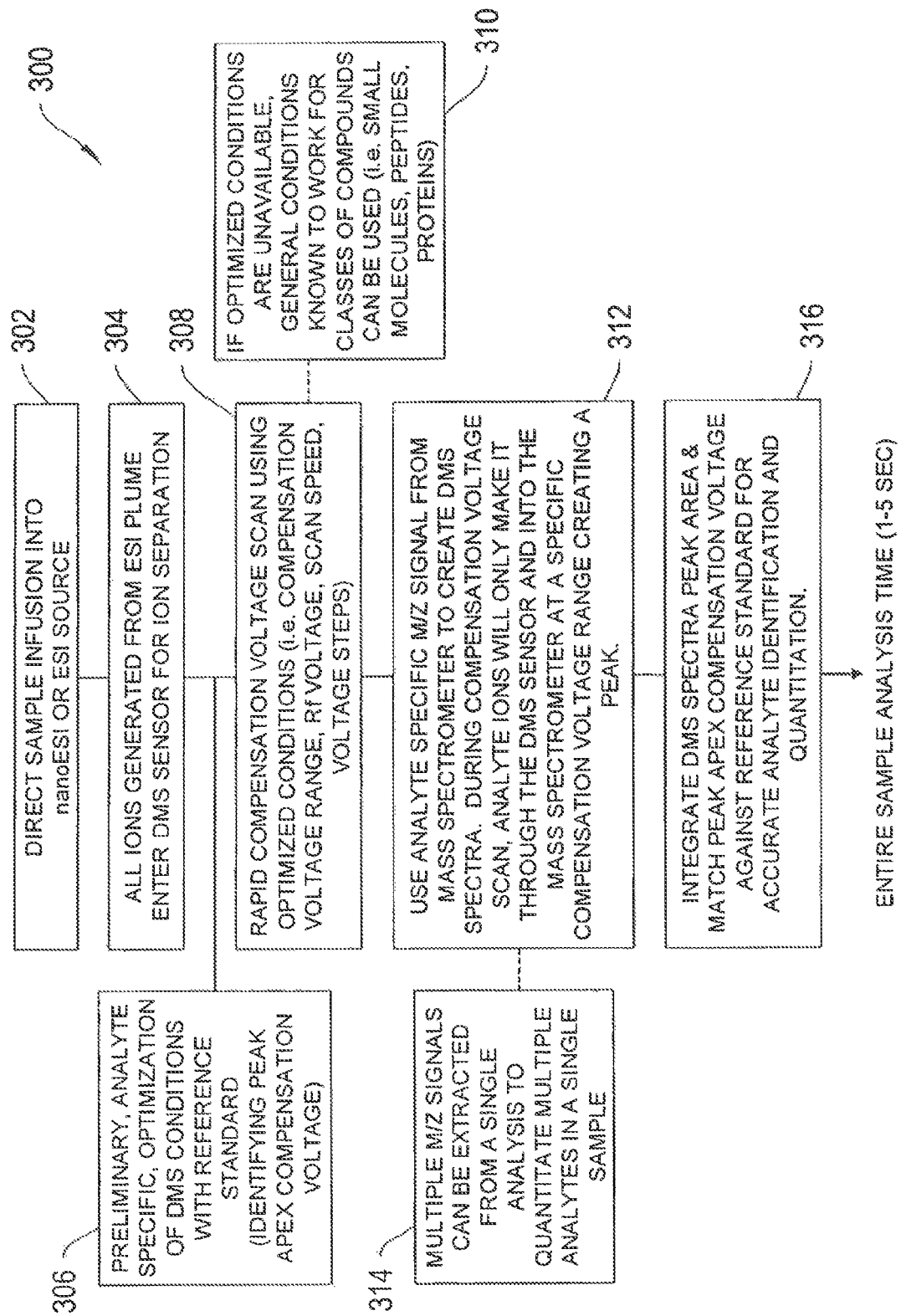
FIG. 3 is a flow diagram of an exemplary sample analysis method for accurate ion identification and quantization according to an illustrative embodiment of the invention.

FIG. 3 is a flow diagram 300 of an exemplary sample analysis method for accurate ion identification and quantization according to an illustrative embodiment of the invention.

First, direct sample S infusion into the nanoESI and/or ESI source 202 is performed (Step 302). Next, all ions generated from an ESI plume enter the DMS sensor and/or filter 210 via the flow path 208 for ion separation (Step 304). A preliminary analyte specific optimization of the DMS filter 210 conditions is performed with reference to a standard whereby the peak apex compensation voltage (Vc) is identified (Step 306). Then, the DMS filter 210 performs a rapid compensation voltage scan using the optimized conditions (e.g., compensation voltage range, Vrf, scan speed, and voltage steps) (Step 308). The optimized condition settings of the DMS filter 210 and other elements of the nanoESI-DMS-MS system 200 may be stored in a data store and/or memory and retrieved at some later time by the controller 242 to set the optimized nanoESI-DMS-MS system 200 conditions. If optimization conditions are not available and/or stored with the controller 242 data store, general conditions know to work for certain ion species and/or classes may be used (Step 310). Classes may include, without limitation, small molecules, peptides, or proteins. Next, the system 200 uses an analyte specific m/z signal from the MS analyzer 240 to create a DMS spectra. During Vc scan, certain analyte ions will pass through the DMS filter 210 and into the MS analyzer 240 over a specific Vc range, creating a ion intensity peak (Step 312). Multiple m/z ion signals may be extracted from a single analysis, DMS filter 210 scan, and/or DMS filter 210 ion intensity peak, to quantize multiple analytes in a single sample (Step 314). Then, the nanoESI-DMS-MS system 200 integrates the DMS ion intensity spectra peak area and matches the peak apex compensation voltage against the reference standard for accurate analyte identification and quantization (Step 316).

For example, the nanoESI-DMS-MS system 200 may be employed for peptide quantization to perform the above Vc scanning approach with directly infused samples. The nanoESI-DMS-MS system 200 may utilize control software, operated by the controller 242, that is configured to identify the DMS peak apex compensation voltage for certain rapid DMS filter 210 Vc scans and capable of averaging multiple Vc scans to be displayed as one DMS spectra.

Peptide Quantization

In one experimental example, where the drift gas modifier conditions were optimized, the use of the nanoESI-DMS-MS system 200 for rapid peptide quantization of directly infused samples was investigated, utilizing the 8000 ppm 2-butanol drift gas modifier condition for all analyses. The angiotensin (ang.) fragment peptide was selected as the analyte of interest to be quantified. The peptide samples for quantitation were prepared in 50/50/water/methanol with 0.1% formic acid for improved ionization compared to the, 80/20 water/methanol with 0.1% formic acid, sample solution conditions used for the optimization work.

In addition, the nanospray capillary tip position and mass spectrometer and/or MS analyzer 240 conditions were optimized for analyte ion sensitivity of the $(M+H)^+$ m/z 482 ion. The MS cone 228 voltage was increased to 40 V and the MS inlet source temperature increased to 70° C.

Figure 4:
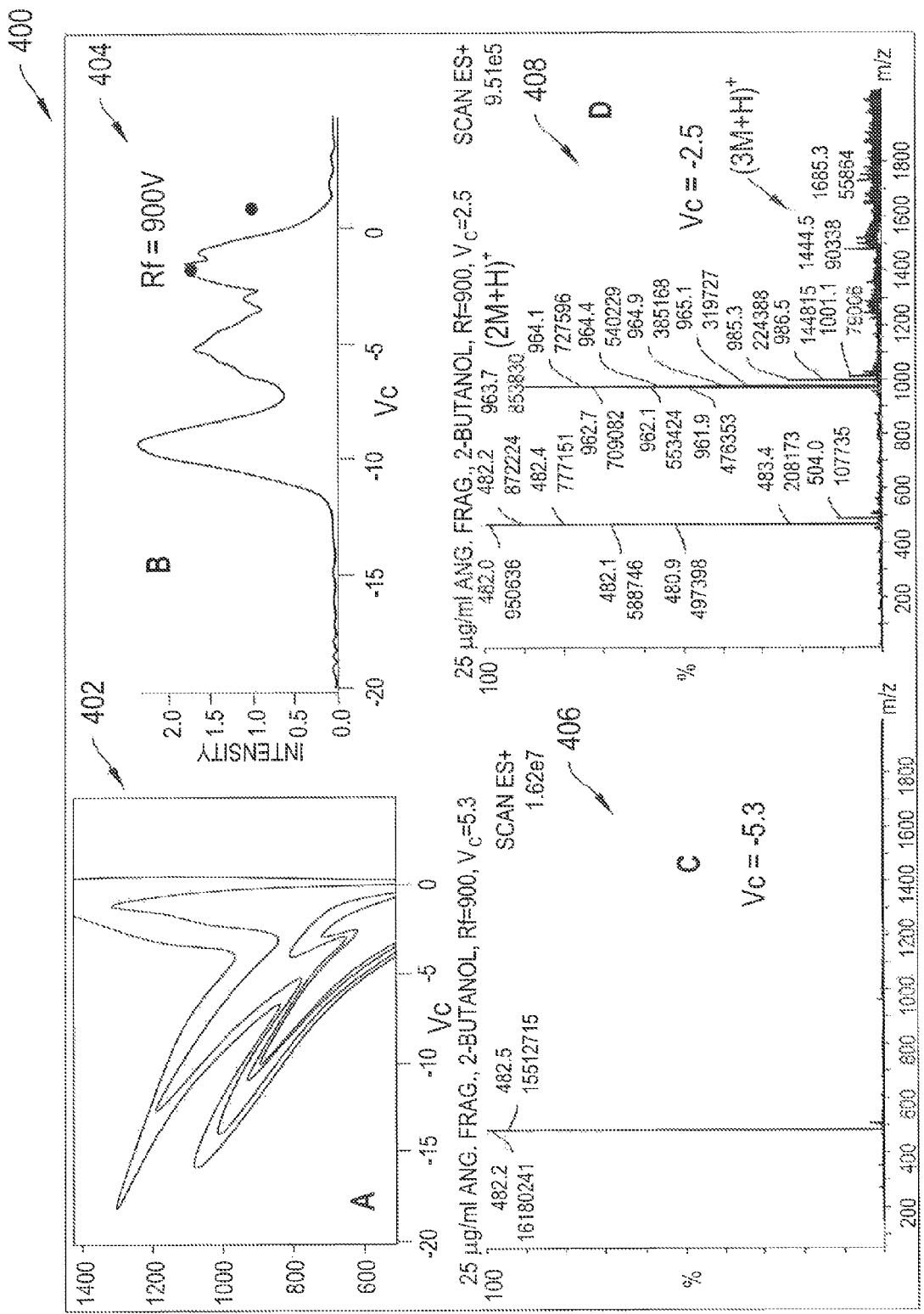
FIG. 4 is a combined graphic display of a three-dimensional plot and an associated two-dimensional plot at Rf=900 v and associated mass spectrometric scans at Vc=−5.3 volts and Vc=−2.5 volts according to an illustrative embodiment of the invention.

FIG. 4 is a combined graphic display 400 of a three-dimensional plot 402 and an associated two-dimensional plot 404 at Rf=900 v and associated mass spectrometric scans 406 and 408 at Vc=−5.3 volts and Vc=−2.5 volts respectively according to an illustrative embodiment of the invention. The plot 402 is a dispersion plot of Vrf versus Vc with ion intensity levels indicated by varying shades of gray. In other embodiments, the plot 402 indicates ion intensity levels by varying color. In another embodiment, the ion intensity may be shown as a surface of varying elevations and/or contours. FIG. 4 shows the DMS dispersion plot 402, DMS spectra at Rf=900 V in plot 404, and the selected Vc point mass spectra 406 and 408 at an Rf=900 V, for a 25 ug/ml ang. fragment reference standard. As support that drift gas modifiers facilitate the de-clustering of higher order peptide aggregate ions, FIG. 4, as illustrated in plots 402, 404, 406, and 408, demonstrates the differential mobility separation of the m/z 482 $(M+H)^+$ monomer ion at a Vc of −5.3 from the m/z 963 $(2M+H)^+$ dimer and 1444 $(3M+H)^+$ trimer ions at a lower Vc of −2.5.

Figure 5:
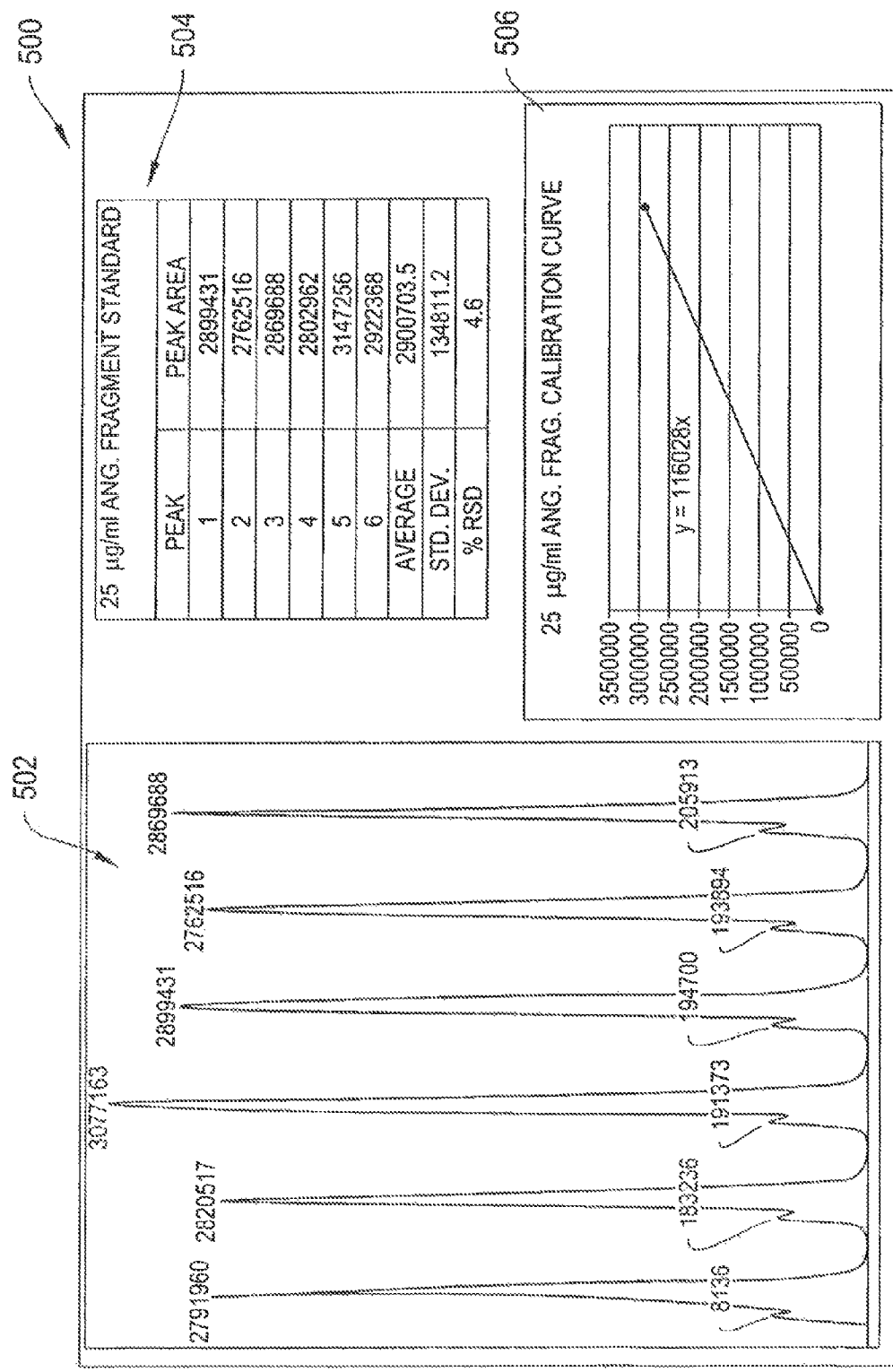
FIG. 5 is a combined graphic view of a multi-scan plot, an associated calibration table of peaks of the multi-scan plot, and calibration curve for 25 ug/ml Ang. Frag. according to an illustrative embodiment of the invention.

FIG. 5 is a combined graphic view 500 of a multi-scan plot 502, an associated calibration table 504 of peaks of the multi-scan plot, and calibration curve 506 for 25 ug/ml Ang. Frag. according to an illustrative embodiment of the invention. To create a reference value reflective of 25 ug/ml angiotensin fragment, ten (10) second Vc scans, at an Rf of 900 V, in m/z 482 selected ion mode, scanning from −15 to 0 V, were collected and the peak area's integrated. The plot 502 shows the m/z 482 peaks generated by six repetitive Vc scans. Repeatability in the generation of the m/z 482 peaks through Vc scans was determined by calculating the percent residual standard deviation (RSD) of the six replicate peaks areas. A RSD of 4.6% for Vc scan peak area repeatability is shown in calibration table 504. The average peak area value was used to generate a calibration line and the equation $y=116028x$ in calibration curve 506, to be used for ang. fragment quantization from a semi-complex peptide sample.

Figure 6:
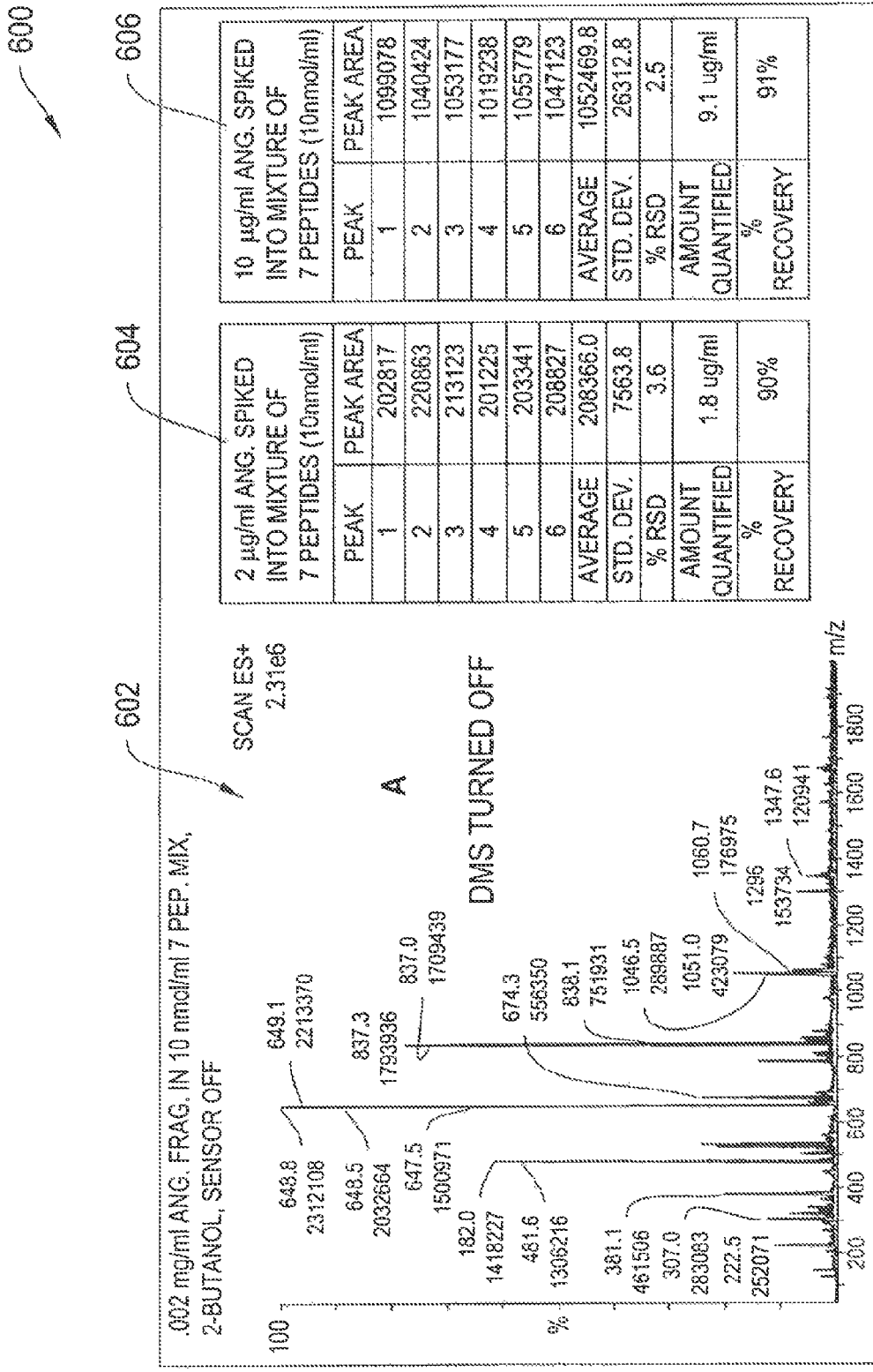
FIG. 6 is a combined graphic view of a mass spectrometric spectra and associated calibration tables for 2 ug/ml and 10 ug/ml Ang. spiked into a mixture of seven peptides according to an illustrative embodiment of the invention.

FIG. 6 is a combined graphic view 600 of a mass spectrometric spectra 602 and associated calibration tables 604 and 606 for 2 ug/ml and 10 ug/ml ang. spiked into a mixture of seven peptides according to an illustrative embodiment of the invention. A sample was created which contained a mixture of the seven different peptides, at 10 nmol/ml each, ranging in mass from 1045 to 1672 Da to create a semi-complex peptide mixture. Two ang. fragment spiked recovery samples were prepared from this peptide mixture, one with an ang. fragment concentration of 10 ug/ml and the other 2 ug/ml. Six replicate 10 second Vc scans were generated for each sample in the same manner as the 25 ug/ml reference standard. FIG. 6 shows the mass spectra 602 for the 2 ug/ml spiked recovery sample with the DMS sensor turned off, demonstrating the ion complexity of the sample. The tables 604 and 606 show the average m/z 482 peak area values and percent RSD for the 2 ug/ml and 10 ug/ml samples respectively.

Based on the average peak area's, ang. fragment recovery values of 90% and 91% for the 2 ug/ml and 10 ug/ml samples were calculated from the equation of the calibration curve 506 of FIG. 5 respectively. The Vc scan % RSD and recovery data illustrate the feasibility for rapid quantization of directly infused samples with the nanoESI-DMS-MS system 200, utilizing fast Vc scanning In another embodiment, Ultra-rapid (0.5-5 sec. range) analysis times are achievable with the fast Vc scanning capabilities of the DMS filter 210 and a fast scanning MS analyzer 240, making the quantitative analysis very desirable for numerous applications in the high-throughput arena.

While certain analyzers have demonstrated a change in an analyte ion's differential mobility behavior through the use of drift gas modifiers and/or dopants, a clear model with regards to the underlying interactions between the modifier and analyte, and the mechanism(s) by which those interactions change an analyte ion's differential mobility behavior, has not been developed. Accordingly, in certain embodiments, the nanoESI-DMS-MS system 200 is configured and/or operated to account for the influence of chemical structure, conformational freedom, H-bonding, electrostatic attraction, and steric repulsion, on gas phase interactions and the mechanisms by which they alter an analyte ion's differential mobility behavior. The proposed mechanisms are significant for a wide spectrum of DMS applications. Based on our results, two gas phase interaction mechanisms which detail drift gas modifier effects on analyte ion differential mobility behavior are defined. Molecular modeling calculations with, for example, CAChe software, enables an in-silico look at the proposed mechanisms. While providing data with strong support of the proposed mechanisms, the molecular modeling data also demonstrated the potential for predictive determinations of differential mobility behavior for an analyte with various drift gas modifiers. In certain embodiments, these predictive determinations are used to analyze a sample to identify certain sample constituents.

Illustrative Experimental Process and/or System Instrumentation

The exemplary nanoESI-DMS-MS system 200, in one embodiment, includes a small size of the DMS sensor (including the DMS filter 210 and DMS detector 212), being approximately 3" in length, about 1" in height, and about ¼" in width. The DMS sensor may also include a simplified interface to the MS analyzer 240 inlet. In one embodiment, the interface allows the DMS sensor to be detachably connectable to the MS analyzer 240. In one configuration, samples were infused into the nanospray ESI source 202 via a Harvard syringe pump at a flow of about 1.25 µL/min. Sample analysis was performed in positive mode nanospray and a capillary voltage of about 3.0 KV was applied. A cone voltage of about 12 V was applied to the inlet MS cone 228 of the MS analyzer 240. The source temperature for the MS analyzer 240 was set to about 40° C.

Returning to FIG. 2, in one embodiment, an ESI-DMS-MS system 200 includes a gas line via inlet 206 into the flow path 208 in the DMS sensor (combined DMS filter 210 and DMS detector 212) opposite of the nanospray inlet 204. This provides an introduction site for the drift gas modifier vapors into the DMS sensor as well as a curtain gas for the nanospray inlet 204. The two detector plates 218 and 220 immediately downstream from the separation electrodes 214 and 216 provide an ion signal for both positive and negative ions. In one embodiment, a hole and/or orifice 238 is included in one of the detector plates 220 to allow for ion transmission into the MS analyzer 240. Despite the hole 238, in one embodiment, an ion signal was still generated by the detector plate and/or electrode 220. In another embodiment, the detector plates 218 and 220 are biased +5 and −5 volts depending on the ion signal polarity desired. In certain embodiments, the positive ion detector plate was assigned to the detector plate 220 with the hole 238. The vacuum generated by the MS analyzer 240 provided the gas flow (measured at approx. 1 L/min) through the DMS sensor and into the MS analyzer 240. The gas line and inlet 226 opposite the DMS sensor inlet 206 had a constant flow of nitrogen at approximately 0.7 L/min (with or without the modifier added). The drift gas modifiers were introduced at a concentration of approximately 150 ppm of the total gas flow through the DMS sensor. In certain embodiments, the DMS sensor was operated at ambient environmental temperature.

Chemicals

Five related compounds, piperidine, cis-dimethyl-piperidine, tetramethyl-piperidine, pentamethyl-piperidine, and 3-hydroxy-piperidine were used as test analytes in the ESI-DMS-MS system 200. The samples were all prepared at 0.5 mM in a solution of 90% HPLC grade water (sigma) and 10% HPLC grade methanol (sigma). 2-propanol, 2-butanol, and cyclopentanol were tested as the various drift gas modifiers (sigma). As shown in FIG. 2, the drift gas modifier vapors were introduced into the DMS sensor by filling a 5-mL glass reservoir 224 with the appropriate modifier and placing it within a gas trap style apparatus and/or vial 244, allowing the modifier to mix with the drift gas in a mixing region 222 before introduction into the DMS sensor. Each of the five analytes were tested with and without all three drift gas modifiers.

Molecular Modeling

Molecular modeling experiments were performed with, for example, CAChe Worksystem Pro Ver. 6.1.10 software (Fujitsu Corp.) on a Compaq Presario 2100 laptop with an Athlon XP 1800+ processor and 512 mb DDR RAM. Global minimum conformation energy values for all complexes were determined by performing the following experiment; property of: Chemical Sample Conformations (CAChe 5.0 experiments), property: Sequence of Conformations, Using: Global Minimum search with MM2. Prior to performing the global minimum conformation calculation for each complex, a single Chemical Sample File containing each component molecule, within close proximity, was created. The surface volume was determined for the minimum energy conformation of the particular complex or individual ion. The change in conformational freedom for a given analyte ion was determined by superimposing the eight lowest energy conformations for that analyte ion and calculating the surface volume of all eight superimposed conformations. The difference in surface volume between the minimum conformation versus all eight superimposed was then determined.

Procedures

For each sample condition tested, a DMS dispersion plot was generated from the DMS sensor positive ion detector plate 220 signal and by scanning compensation voltages (Vc) from about −20 to +5 V for each Rf voltage ranging from about +500 to +1500 V, in approximately 10 V increments.

Figure 7:
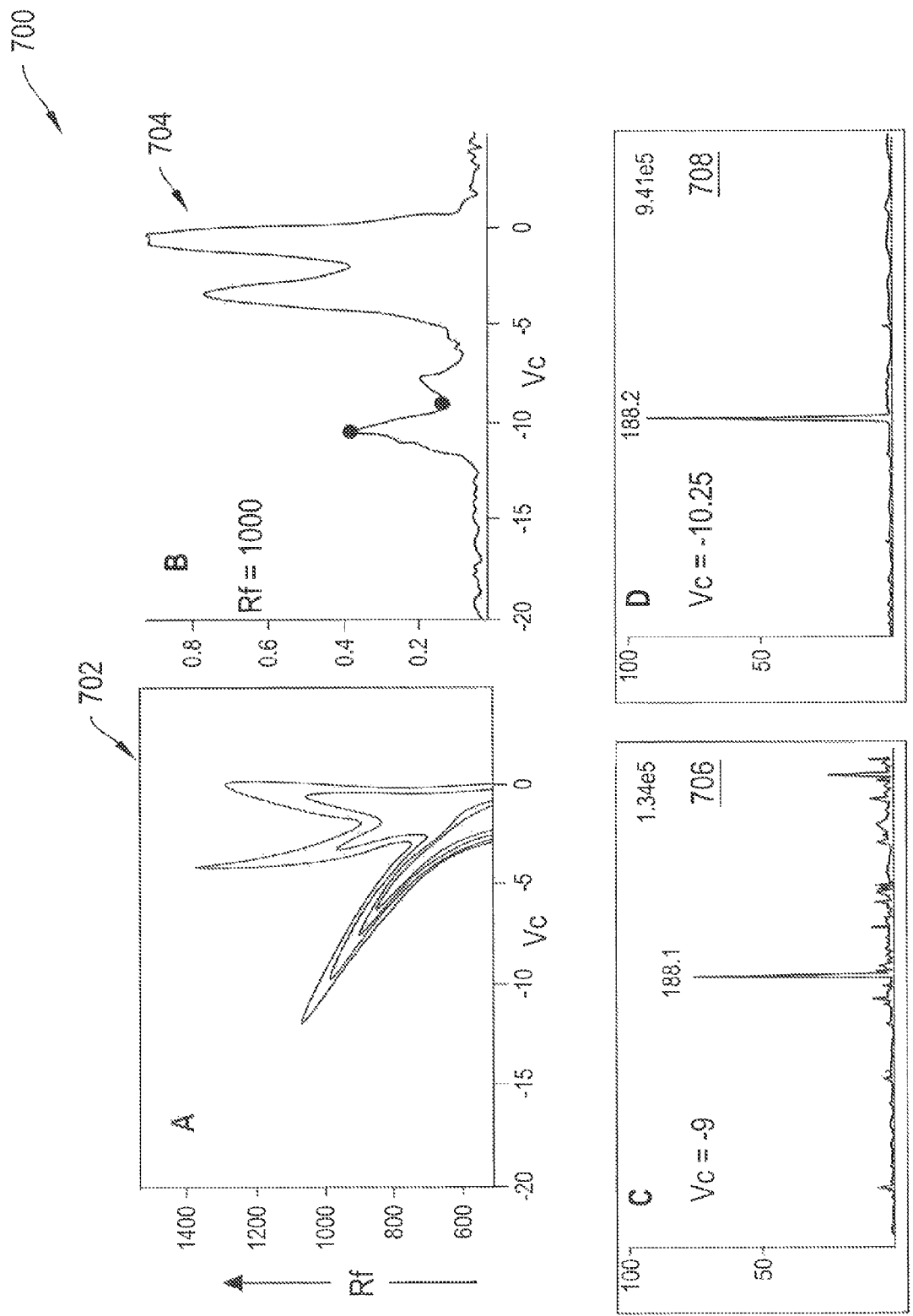
FIG. 7 is a combined graphic view of a three-dimensional plot and an associated two-dimensional plot at Rf=1000 v and associated mass spectrometric spectra at Vc=−9 volts and Vc=−10.25 volts respectively according to an illustrative embodiment of the invention.

FIG. 7 is a combined graphic view 700 of a three-dimensional dispersion plot 702 and an associated two-dimensional plot 704 at Rf=1000 v and associated mass spectrometric spectra 706 and 708 at Vc=−9 volts and Vc=−10.25 volts respectively according to an illustrative embodiment of the invention. The sample differential mobility dispersion plot 702 demonstrates DMS separation of various ions. As the Vrf voltage is increased, the mobility/velocity of some ions away from DMS filter electrode 214 and/or 216 is increased, requiring a larger Vc of opposite polarity for safe travel to the detector plate 220. A scan rate of about 1.03 sec/scan was used for each Vc scan, consisting of 100 steps between about −20 and +5 volts, enabling an entire dispersion plot to be generated in approximately 100 seconds.

From the dispersion plot 702 data, a DMS spectra (Vc vs. ion signal), shown in plot 704, can be generated for a given Rf voltage Vrf. For any Rf and Vc setting on the dispersion plot 702, a mass spectra can be collected by the MS analyzer 240, providing insight into the ion make up at a particular Vc point on the dispersion plot 702. The point D and C are selected Vc points for which mass spectra were collected, enabling the determination of the Vc position corresponding to the maximum m/z 188 ion signal, shown in plots 706 and 708. After the generation of a dispersion plot 702 for each sample condition, Rf and Vc points were selected throughout the plot 702 to collect associated and/or matching mass spectra via the MS analyzer 240. For each selected Rf and Vc voltage setting, a mass spectra was collected which averaged about 30 seconds worth of 0.1 second mass scans. Mass spectra were also collected at the MS analyzer 240 for each sample condition with the DMS sensor turned off, allowing all the ions to enter the MS analyzer 240. The combination of dispersion plots and the selected Rf and Vc point mass spectra enabled the construction of accurate Rf versus Vc plots of the maximum ion intensity for all the analyte ions of interest. The Rf versus Vc plots identify the effects of the drift gas modifiers on shifting the analyte ions' Vc for a given Rf. Molecular modeling was used to examine the proposed molecular gas phase interaction mechanisms taking place.

Dimer Ion Formation and Separation

In one experimental operation of the ESI-DMS-MS system 200, five piperidine analytes were chosen to investigate chemical differences in dimer/cluster ion formation. It was presumed that the amine in each of the compounds would be the main site for dimer formation. By sterically restricting access to the amine, through methylating the adjacent C atoms, and the amine itself in the case of pentamethyl-piperidine, a reduction in dimer formation was expected. In contrast, with the addition of a hydrogen bonding group, as in 3-hydroxy-piperidine, it was expected that dimer formation would be enhanced.

Figure 8:
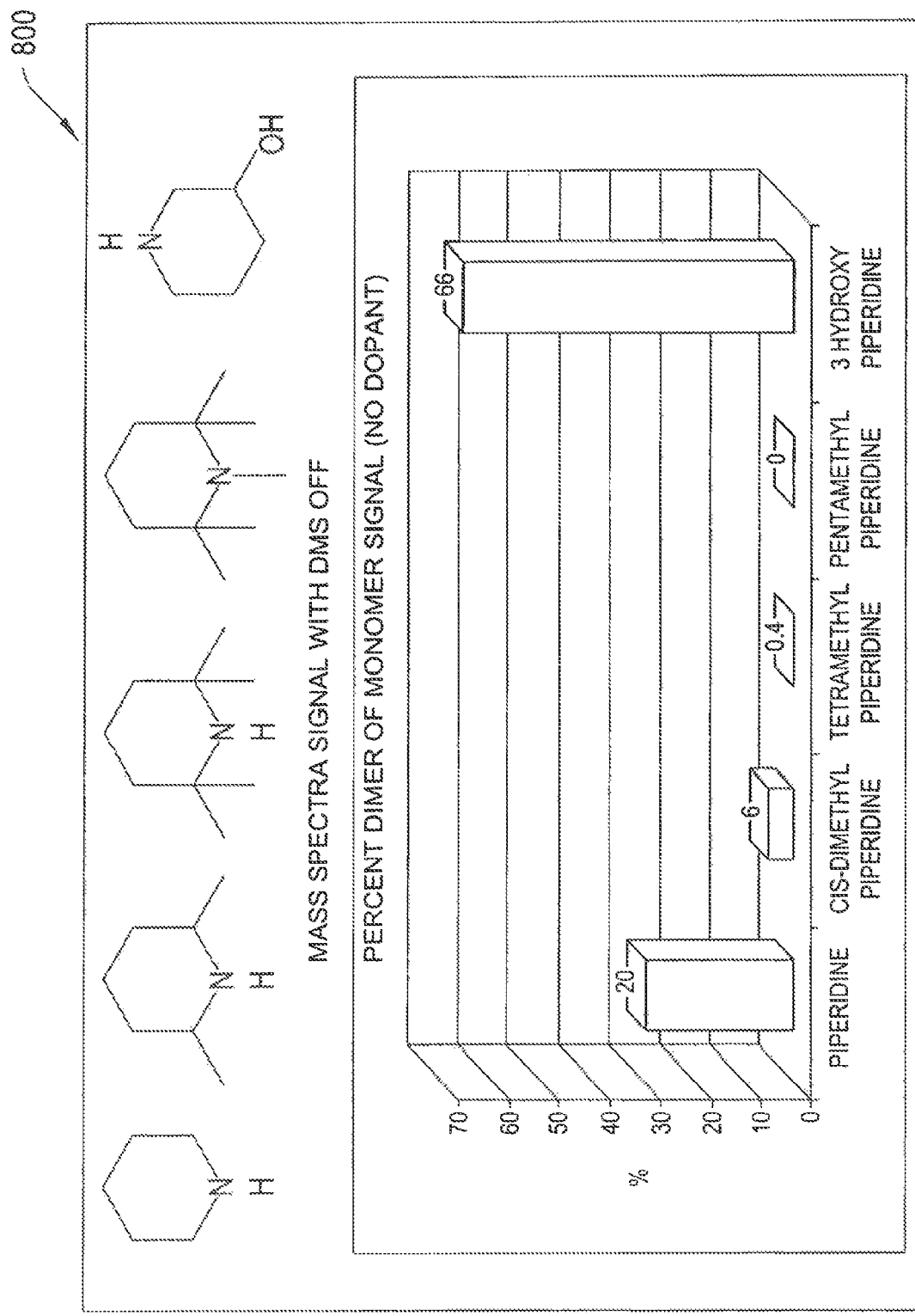
FIG. 8 is a bar graph of the percentage of dimer ion signal to monomer ion signal for each analyte with no drift gas modifier and a DMS pre-filter turned off.

FIG. 8 is a bar graph 800 that shows the percentage of dimer ion intensity to monomer ion intensity, calculated from the mass spectra collected by the MS analyzer 240, for each of the analyte samples with the DMS sensor turned off. As illustrated, with the increase in steric hindrance around the amine, dimer intensity decreases. The pentamethyl-piperidine sample, having the most limited access to the amine, demonstrated no detectable dimer ion. In contrast, the 3-hydroxy-piperidine sample demonstrated a greater than 2-fold increase in dimer signal compared to the piperidine sample. For the analytes capable of generating sufficient dimer ion signal, DMS separation using the DMS filter 210 between the monomer and dimer ions was observed.

Figure 9:
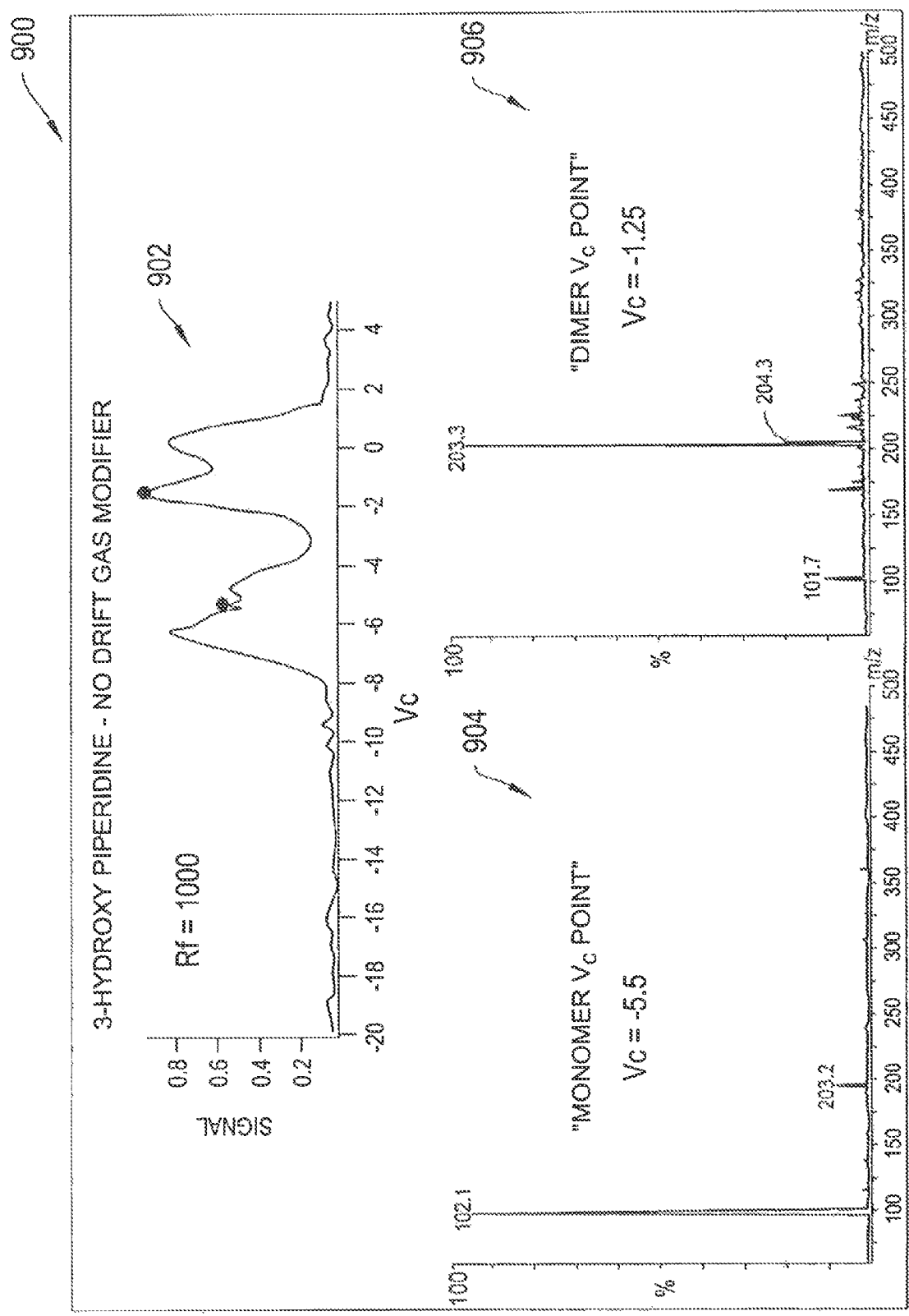
FIG. 9 is a combined graphic view the DMS spectra for 3-hydroxy piperidine with no gas modifier and associated mass spectrometric spectra at Vc=−5.5 volts (monomer Vc point) and Vc=−1.25 volts (dimer Vc point) respectively.

FIG. 9 is a combined graphic view 900 of the DMS spectra for 3-hydroxy piperidine with no gas modifier and associated mass spectrometric spectra at Vc=−5.5 volts (monomer Vc point) and Vc=−1.25 volts (dimer Vc point) respectively. FIG. 9 shows the DMS spectra detected at the DMS detector 212 and corresponding mass spectra detected by the MS analyzer 240 for the 3-hydroxy-piperidine sample with no drift gas modifier at an Rf voltage of 1000 volts. At the Vc point of −1.25 volts, the 3-hydroxy-piperidine dimer ion of 203 m/z $[2C_5H_{11}NO+H^+]^+$ is shown, while at the Vc point of −5.5 volts, the 102 m/z singly protonated monomer ion is shown, as well as the 203 m/z dimer ion. The presence of a dimer ion, at the "monomer ion Vc point" has been attributed to dimer formation by reaction of the monomer ion with neutral analyte molecules after the monomer ion has passed through the DMS. As a result, the dimer ion has not been identified as a contributor to the "monomer ion Vc point" position.

In certain configurations, dimer ions that are present at the "monomer ion Vc point" may participate as part of an ion' equilibrium, consisting of monomer ion and monomer-neutral molecule cluster ions, that comprise the "monomer ion Vc point". It appears that, in many cases, the intensity of dimer/cluster ion signal offered by the mass spectra of a MS analyzer in conventional systems may be significantly under representing the true contribution of the dimer/cluster ions to the equilibrium. When viewing a Vc point as an ion' equilibrium, the effective cross sectional area for that point must take into account the cross sectional area for each ion and their contributing amounts. It is likely that conventional mass spectrometry by itself is unable to provide an accurate view of the ion' equilibrium composition that contributes to a particular Vc point. Specifically, there is a high potential for de-clustering of non-covalently bound ions as they pass through the MS inlet via the MS cone 228. Thus, in certain embodiments, the ESI-DMS-MS system 200 employs the lowest feasible MS cone 228 voltage setting in order to maintain as much dimer/cluster ion signal as possible.

If the dimer ion is to be considered a true component of the monomer ion Vc point, it is necessary to define it's presence in two well separated Vc points for a given Rf voltage. In certain configurations, it appears that two types of dimer formations are present, and are responsible for the differences in Vc point position. Equations 1 and 2 below show the two proposed dimer ion formations.

$$MH^+_{(gas)} + M_{(gas)} \rightarrow MH^+ \ldots M_{(gas)} \qquad \text{Eq.1}$$

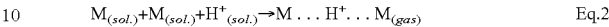

$$M_{(sol.)} + M_{(sol.)} + H^+_{(sol.)} \rightarrow M \ldots H^+ \ldots M_{(gas)} \qquad \text{Eq.2}$$

Figure 10A:
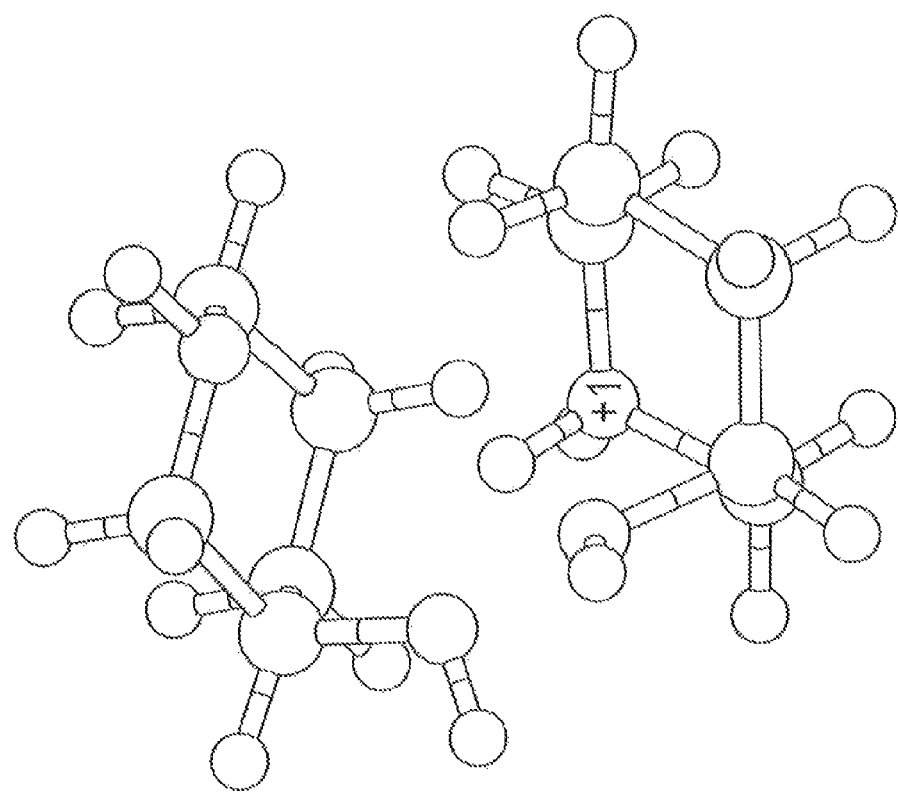
FIG. 10A is an exemplary view of a dimer ion structure that may be present in the monomer Vc point of FIG. 9.
Figure 10B:
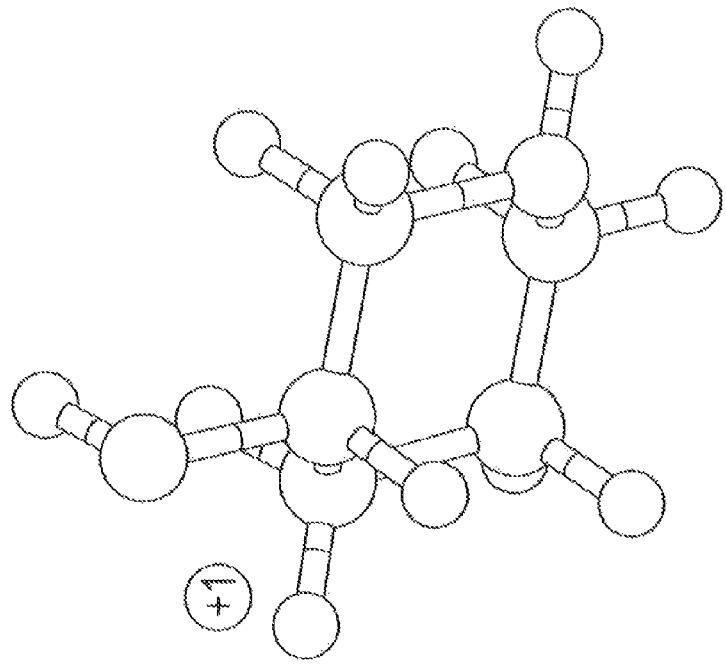
FIG. 10B is an exemplary view of a dimer ion structure that is formed as a shared proton between two neutral analyte molecules which may be present in the dimer Vc point of FIG. 9.
Figure 10B:
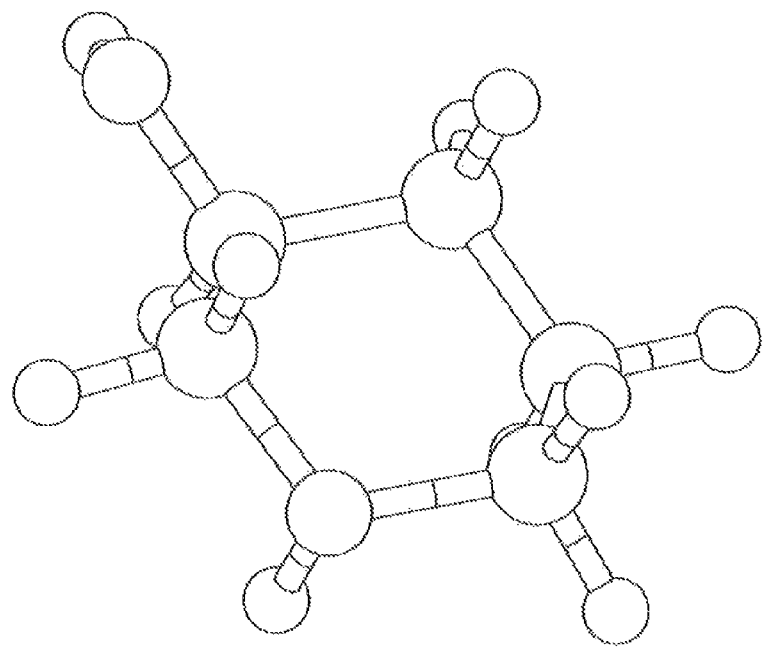

FIGS. 10A and 10B show the CAChe global minimum energy conformation determination for the two proposed dimer formations using the 3-hydroxy-piperidine compound as a model.

FIG. 10A is an exemplary view 1000 of a dimer ion structure that may be present in the monomer Vc point of FIG. 9. FIG. 10A represents a post electrospray ionization dimer formation between an already protonated analyte ion and neutral analyte molecule. This type of formation would correlate to the dimer ion that exists as part of the monomer Vc point and is representative of a clustering/de-clustering process. Under certain conditions, an analyte ion could cluster with a neutral polar water molecule(s) in the drift gas during the low field portion of the electrical waveform, effectively increasing the cross sectional area of the analyte ion. During the high field portion of the waveform, the cluster would be dissociated, reducing its effective cross sectional area. In this scenario, the dimer ion would be continuously forming and dissociating as part of the monomer ion' equilibrium. The stronger the attraction between the analyte ion and analyte neutral, the longer the dimer ion exists and contributes to the overall cross sectional area of the ion' equilibrium.

FIG. 10B is an exemplary view 1002 of a dimer ion structure that is formed as a shared proton between two neutral analyte molecules which may be present in the dimer Vc point of FIG. 9. This type of dimer would form during the electrospray process in which two neutral analyte molecules compete for the proton addition, resulting in a stable shared proton dimer configuration. The shared proton dimer model has previously been demonstrated by infrared multi-photon photodissociation (IRMPD) spectroscopy for shared proton $H_2O$ dimer ions in the gas phase formed by atmospheric ion spray. This type of dimer structure correlates to the dimer ion present in the "dimer ion Vc point", and would represent a structure that may not be as easily dissociated as the dimer structure in FIG. 10A, leading to a larger overall cross sectional area and lower Vc point position. This type of dimer structure may also be favorable for higher degrees of clustering which will be discussed later herein.

Monomer Ion' Equilibrium-Core Mechanism

In one exemplary configuration, three drift gas modifiers were selected to investigate trends with regards to electrostatic and H-bonding based interactions between the neutral gas phase modifier molecules and analyte ions. Preliminary tests with hydrocarbon gas phase modifiers, acting as non-polar controls, indicated that having electrostatic attraction between the modifier and analyte ions was vital to altering the analyte ion's differential mobility behavior. It was expected that an electrostatic attraction would exist between the hydroxy group of the alcohol modifiers and the positively charged N on the protonated monomer analyte ions. Equation 3 below depicts the adduct ion formed between a protonated analyte monomer ion and neutral modifier molecule.

$$MH^+_{(gas)} + Modifier_{(gas)} \rightarrow MH^+ \ldots Modifier_{(gas)} \qquad \text{Eq. 3}$$

Figure 11:
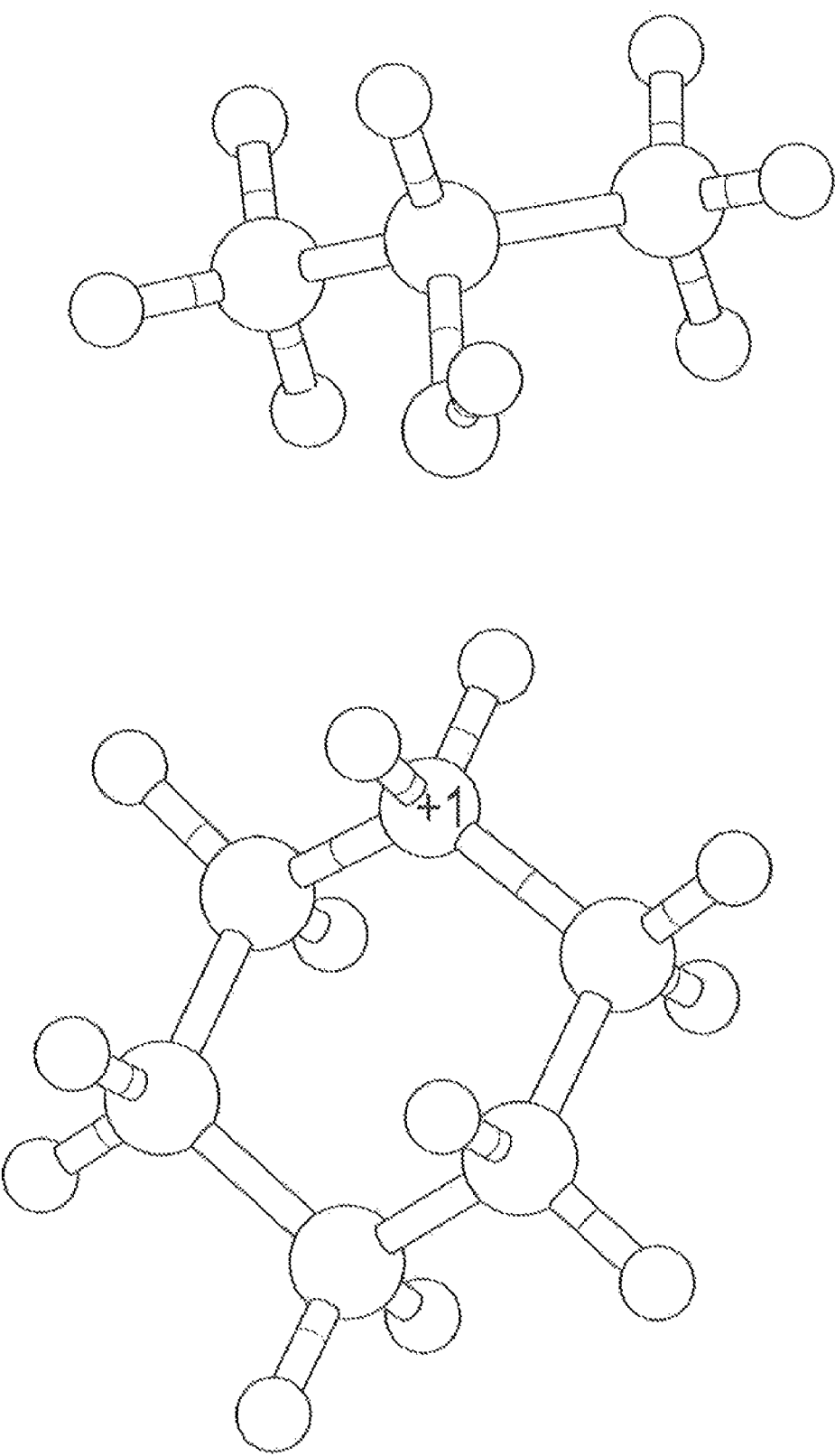
FIG. 11 is an exemplary view of a protonated piperidine and neutral 2-propanol molecule.

FIG. 11 is an exemplary view 1100 that shows the CAChe global minimum energy conformation determination for the interaction between the protonated piperidine analyte and the neutral 2-propanol molecule. As anticipated, the hydroxy group in 2-propanol coordinates with the positively charged N in piperidine.

Figure 12:
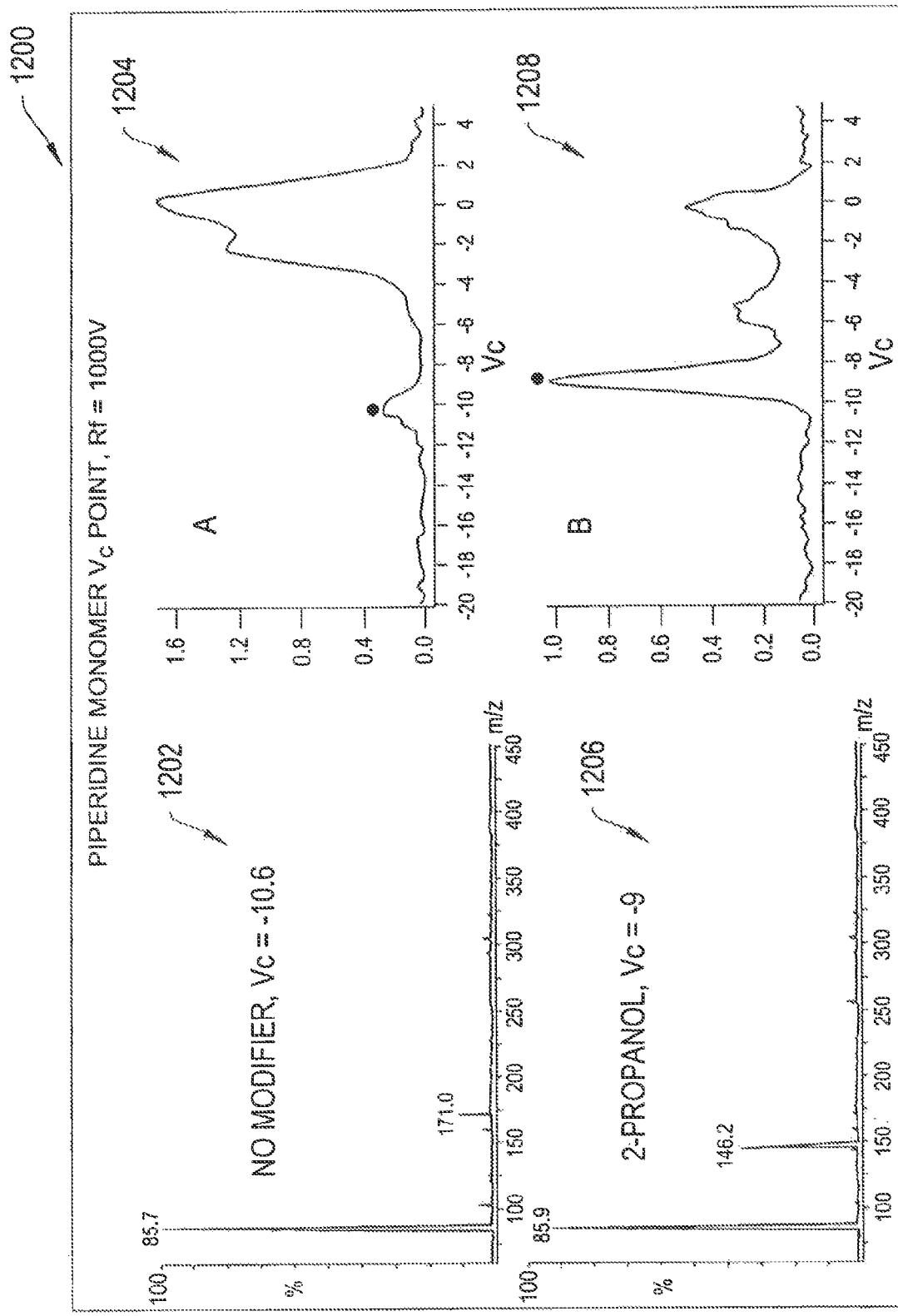
FIG. 12 is a combined graphic view of the DMS spectra for piperidine at an Rf=1000 volts with no modifier and associated mass spectrometric spectra and the DMS spectra with a 2-propanol modifier and associated mass spectrometric spectra.

FIG. 12 is a combined graphic view 1200 of the DMS spectra 1204 for piperidine at an Rf=1000 volts with no modifier and associated mass spectrometric spectra 1202 and the DMS spectra 1208 with a 2-propanol modifier and associated mass spectrometric spectra 1206. FIG. 12 compares the DMS spectra for piperidine with and without the 2-propanol drift gas modifier at an Rf voltage of 1000. The mass spectra 1202 and 1206 were collected at the Rf and Vc settings corresponding to the monomer ion peak maximum for each DMS spectra 1204 and 1208. The m/z 86 ion corresponds to the protonated piperidine monomer ion $C_5H_{11}NH^+$, the m/z 171 ion is the protonated piperidine dimer ion $[C_5H_{11}+C_5H_{11}NH^+]^+$, and the m/z 146 ion is the 2-propanol-piperidine adduct ion $[C_5H_{11}NH^++C_3H_7OH]^+$. It can be seen that the addition of the 2-propanol modifier produced a new analyte-modifier adduct ion (the m/z 146 ion), which resulted in a shift of the monomer Vc point to a lower Vc, reflecting an increase in the overall cross sectional area of the monomer ion' equilibrium in the presence of the 2-propanol drift gas modifier. While the MS analyzer 240 ion signal intensity of the non-covalently bound ions is likely not quantitative with respect to the monomer ion signal, the dimer and modifier adduct ion signal intensities relative to the monomer ion signal do provide valuable comparative data.

The mass spectra 1202 and 1206 indicate that the addition of the 2-propanol modifier to the drift gas induces a competitive formation in favor of the analyte-alcohol adduct ion over that of the dimer ion. Table 1 shows the calculated minimum conformation energy values and surface volume values for the piperidine dimer and piperidine-2-propanol adduct ion complexes.

TABLE 1

Minimum conformation energy and surface volume values for piperidine dimer and 2-propanol adduct complexes

|  | Minimum Conformation Energy (kcal/mol) | Surface Volume |
|---|---|---|
| piperidine(+)-piperidine | 6.3 | 7075 |
| piperidine(+)-2-propanol | −16.1 | 6535 |

The lower minimum energy value for the adduct ion indicates a greater likelihood of formation for the adduct ion than the dimer ion, consistent with the mass spectral data. The CAChe surface volumes shown in Table 1 provide values reflective of the cross sectional area for the complex ions'. While the dimer ion has a greater cross sectional area than the modifier adduct ion, a larger contribution of modifier adduct ions to the monomer ion' equilibrium, compared to dimer ion contribution when no modifier is used, could result in an overall increase in the monomer ion' equilibrium's cross sectional area when the 2-propanol modifier is used.

This explains the shift of the monomer ion Vc point to a lower Vc with the addition of the 2-propanol modifier to the drift gas. This type of effect is referred to as the Core interaction mechanism, where the drift gas modifier molecule interacts with the analyte ion to form a new ion entity that exists as part of the analyte ion' equilibrium. The same Core mechanism can be seen in FIG. 13 for the dimethyl-piperidine analyte with and without 2-butanol as a drift gas modifier.

Figure 13:
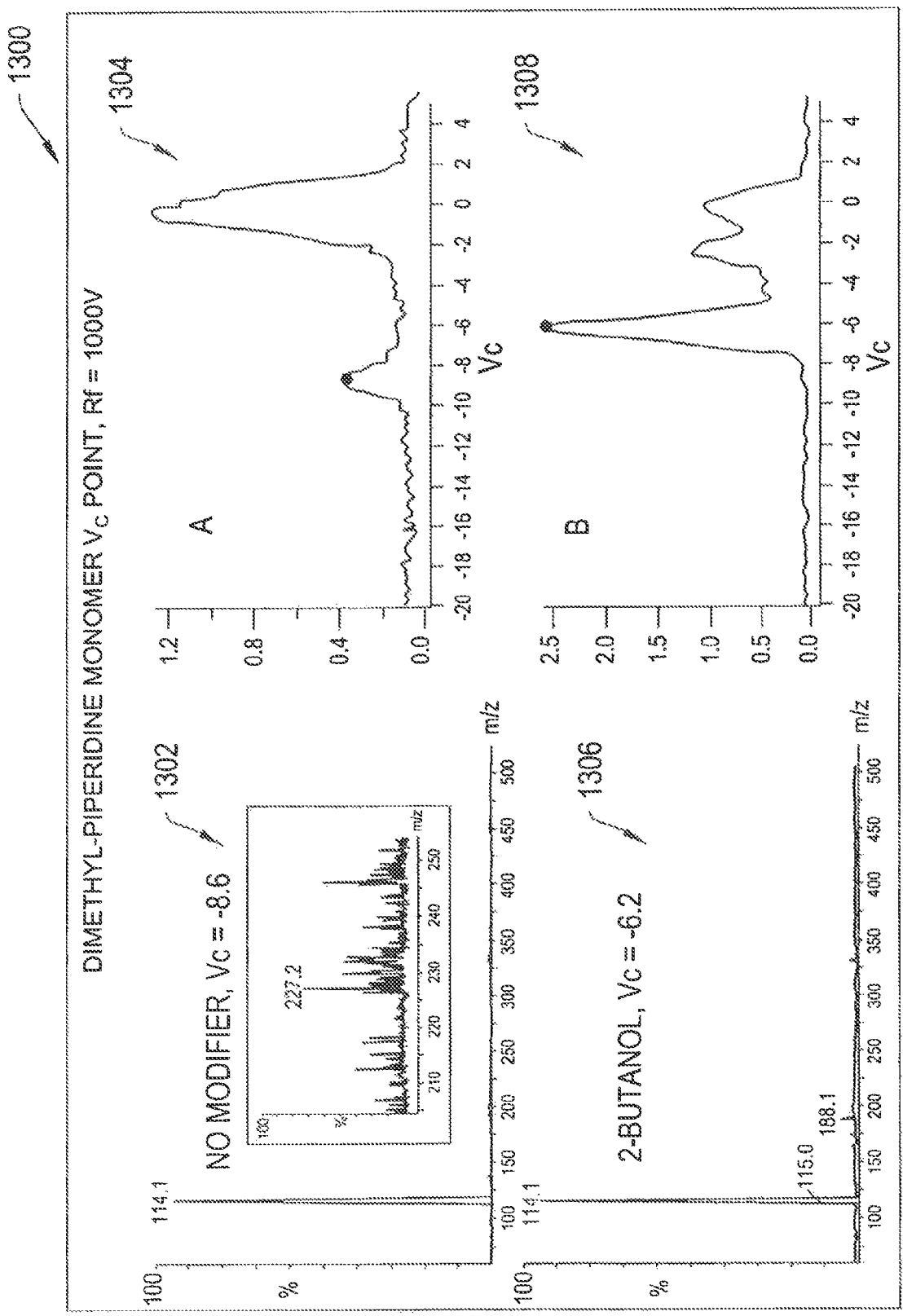
FIG. 13 is a combined graphic view of the DMS spectra for dymethyl-piperidine at an Rf=1000 volts with no modifier and associated mass spectrometric spectra and the DMS spectra with a 2-butanol modifier and associated mass spectrometric spectra.

FIG. 13 is a combined graphic view 1300 of the DMS spectra 1304 for dymethyl-piperidine at an Rf=1000 volts with no modifier and associated mass spectrometric spectra 1302 and the DMS spectra 1308 with a 2-butanol modifier and associated mass spectrometric spectra 1306. The DMS spectra 1304 shows the m/z 114 dimethyl-piperidine monomer ion $C_7H_{15}NH^+$. The m/z 227 dimer ion $[C_7H_{15}N+C_7H_{15}NH^+]^+$ is present at an ion signal only slightly above the noise as shown in the mass spectra 1302. The DMS spectra 1308 shows the monomer ion plus the presence of the dimethyl-piperidine-2-butanol adduct ion $[C_7H_{15}NH^++C_4H_9OH]^+$ at m/z 188. FIGS. 9(a) and 9(b) show the shift of the dimethyl-piperidine monomer Vc point from −8.6 to −6.2 Vc with the addition of 2-butanol vapors to the drift gas.

The 3-hydroxy-piperidine analyte was selected as a test compound because of its increased potential for hydrogen bonding and electrostatic interactions due to the presence of the hydroxyl group. As previously shown in FIG. 8, the 3-hydroxy-piperidine analyte readily forms the greatest dimer/monomer ion ratio out of all five test compounds.

Figure 14:
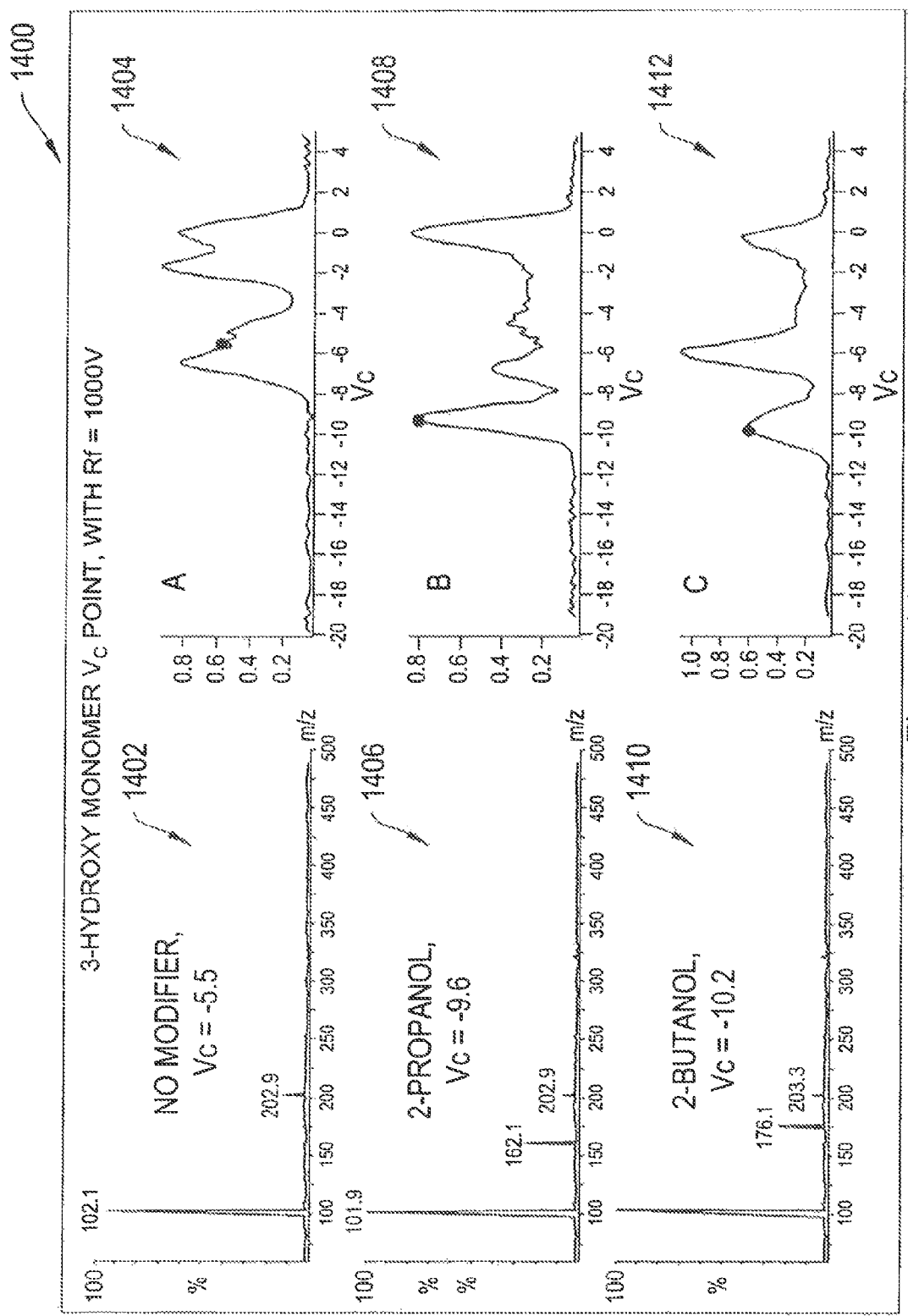
FIG. 14 is a combined graphic view of 3 hydroxy-piperdine at an Rf=1000 volts showing the DMS spectra with no modifier, a 2-propanol modifier, and a 2-butanol modifier along with their associated mass spectrometric spectra respectively.

FIG. 14 is a combined graphic view 1400 of 3 hydroxy-piperidine at an Rf=1000 volts showing the DMS spectra 1404 with no modifier, the DMS spectra 1408 with a 2-propanol modifier, and the DMS spectra 1412 with a 2-butanol modifier along with their associated mass spectrometric spectra 1402, 1406, and 1410 respectively. The DMS spectra 1404, 1408, and 1412 show the mass spectra collected for the monomer Vc point from each condition. The DMS spectra 1404 shows the m/z 102 3-hydroxy-piperidine monomer ion as well as the m/z 203 singly charged dimer ion $[C_5H_{11}NO+C_5H_{11}NOH^+]_+$. The DMS spectra 1408 and 1412 illustrate the presence of the m/z 162 and m/z 176 adduct ions corresponding to the 2-propanol adduct $[C_5H_{11}NOH^++C_3H_7OH]^+$ and 2-butanol adduct $[C_5H_{11}NOH^++C_4H_9OH]^+$ ions respectively. In both of the DMS spectra 1408 and 1412, the 3-hydroxy-piperidine dimer ion is still present at a significant signal relative to the monomer ion. This is different than demonstrated for the piperidine and dimethyl piperidine compounds, where no dimer ion signal was present when the drift gas modifiers were used. Table 2 shows the calculated minimum conformation energy values and surface volume values for the 3-hydroxy-piperidine dimer, 3-hydroxy-piperidine-2-propanol adduct, and 3-hydroxy-piperidine-2-butanol adduct ion complexes.

TABLE 2

Minimum conformation energy and surface volume values for 3-hydroxy-piperidine dimer, 2-propanol adduct, and 2-butanol adduct complexes

|  | Minimum Conformation Energy (kcal/mol) | Surface Volume |
|---|---|---|
| 3hydroxy-piperidine(+)-3hydroxy-piperidine | −29.7 | 7348 |
| 3hydroxy-piperdine(+)-2-propanol | −31.9 | 6529 |
| 3hydroxy-piperidine(+)-2-butanol | −30.2 | 7178 |

The minimum conformation energy values for the dimer and monomer-alcohol adduct complexes are very similar, all within 2.2 kcal/mole difference of each other. This differs significantly from the 22.4 kcal/mole difference between the piperidine dimer ion and piperidine-2-propanol adduct ion energy values shown in Table 1. Unlike what has been demonstrated with the piperidine and dimethyl piperidine compounds, the 3-hydroxy-piperidine compound provides similar clustering strength to form gas phase dimer ions as it does monomer-alcohol adduct ions, resulting in a more balanced contribution to the overall monomer ion' equilibrium from both dimer (larger surface volume) and adduct ions (smaller surface volumes). This results in an overall decrease in the effective cross sectional area for the monomer ion' equilibrium when the 2-propanol or 2-butanol drift gas modifiers are used compared to no modifier. This decrease in the effective cross sectional area of the monomer ion' equilibrium is reflected in the monomer ion Vc point shift to a larger Vc value with the use of either the 2-propanol or 2-butanol drift gas modifier, as shown in FIG. 14.

Monomer Ion' Equilibrium-Facade Mechanism

Understanding and modeling the nature of the gas phase interactions that govern an analyte ions differential mobility behavior is critical to quantization of certain ions. It is clear that each analyte is unique, even within the same class of compounds, and that a given drift gas modification may have opposite effects on shifting analyte Vc point positions for different analytes. However, the Core mechanism does not appear to be the only mechanism by which drift gas modifications can have significant effects on an analyte ion's differential mobility behavior.

The pentamethyl-piperidine compound was selected as a test analyte for the steric hindrance it provides with regard to spatial access to it's protonated N. Of all five piperidine related test compounds, pentamethyl-piperidine has the most sterically blocked N, and demonstrated zero dimer ion signal as shown in FIG. 8.

Figure 15:
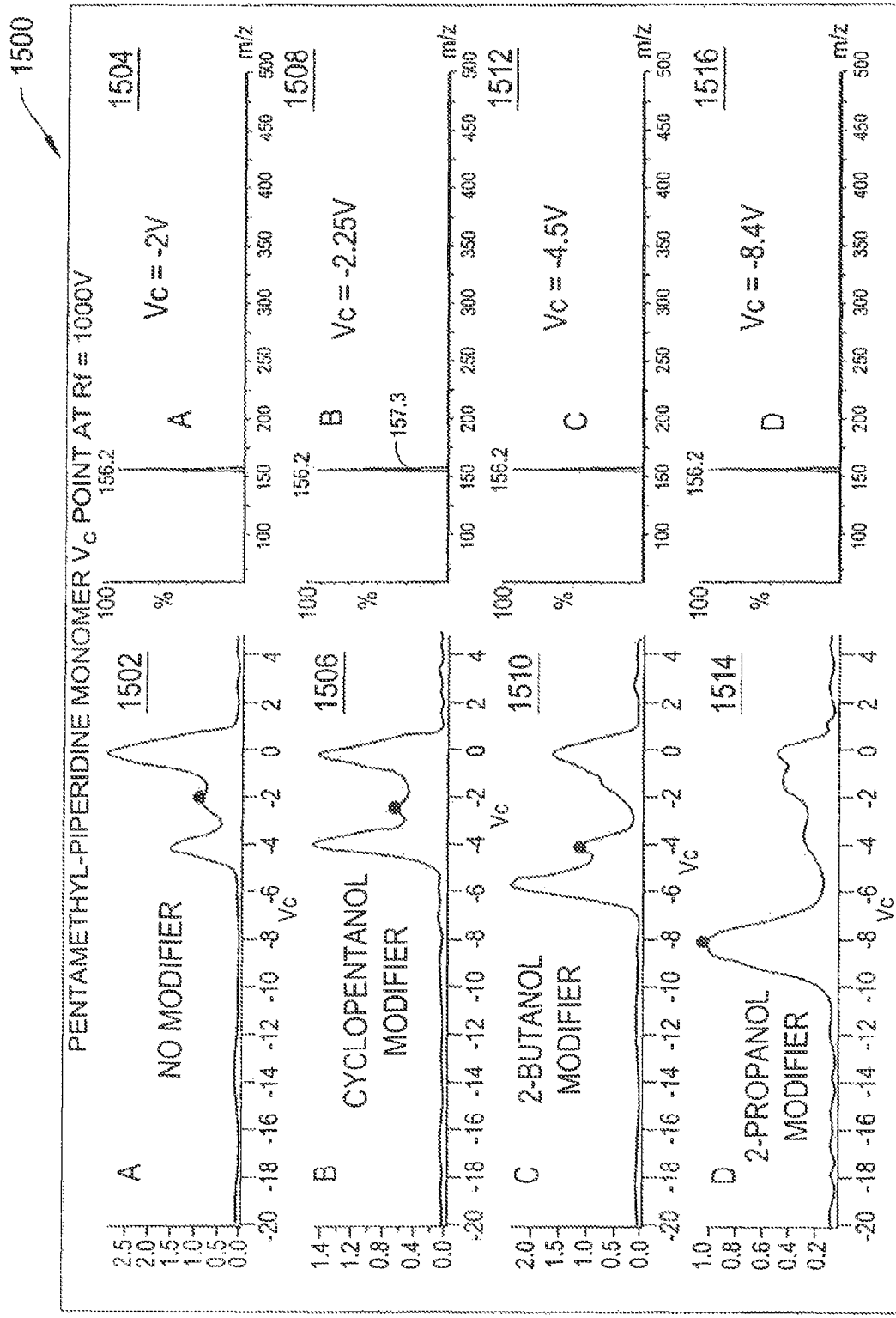
FIG. 15 is a combined graphic view of pentamethyl-piperdine at an Rf=1000 volts showing the DMS spectra with no modifier, a cyclopentanol modifier, a 2-butanol modifier, and a 2-propanol modifier along with their associated mass spectrometric spectra respectively.

FIG. 15 is a combined graphic view 1500 of pentamethyl-piperdine at an Rf=1000 volts showing the DMS spectra 1502 with no modifier, the DMS spectra 1506 with a cyclopentanol modifier, the DMS spectra 1510 with a 2-butanol modifier, and the DMS spectra 1514 with a 2-propanol modifier along with their associated corresponding monomer Vc point mass spectrometric spectra 1504, 1508, 1512, and 1516 respectively. The mass spectra 1504, 1508, 1512, and 1516 corresponding to the monomer Vc points 1502, 1506, 1510, and 1514 show the presence of only the m/z 156 pentamethyl-piperidine monomer ion, $C_{10}H_{21}NH^+$, for all four conditions. None of the mass spectra 1504, 1508, 1512, and 1516 demonstrate dimer or drift gas modifier adduct ions. Despite no mass spectrometer signal for dimer or modifier adduct ions in the monomer Vc points, significant monomer Vc point shifts to larger Vc values occurred with 2-propanol and 2-butanol, as well as a slight Vc shift with cyclopentanol. The monomer Vc point shifts indicate a decrease in the effective cross sectional area for monomer ion' equilibria when the drift gas modifiers are used. Thus, in certain embodiments, a second gas phase drift gas modifier interaction mechanism is employed in which electrostatic attraction between the analyte ion and neutral molecule is still the governing force.

However, unlike the proposed Core mechanism, the interaction between the analyte ion and neutral molecule is short lived or of reduced attraction, such that an analyte-modifier adduct ion is not formed. The effect seen on analyte differential mobility behavior through this mechanism is one of decreasing an analyte ion's conformational freedom which reduces its cross sectional area. The total conformational space or freedom of an analyte ion takes into account all energetically possible bond angles and rotations. Multiple short lived attractions between the analyte ion and drift gas modifier may restrict the analyte ion's conformational freedom.

FIG. 16A is an exemplary view 1600 of a protonated pentamethyl-piperidine complex with and without an associated molecular electron density cloud. FIG. 16B is an exemplary view 1602 of a neutral 2-propanol complex with and without an associated molecular electron density cloud. FIGS. 16A and 16B demonstrate the reduction in conformational freedom imparted on the analyte ion by the modifier molecule. The methyl side chains of pentamethyl-piperidine are restricted from the space occupied by 2-propanol, resulting in an overall decrease in the effective cross sectional area for the pentamethyl piperidine ion. This effect may be referred to as the Façade interaction mechanism.

While both the Core and Façade mechanisms have been described as two independent gas phase interaction mechanisms, both mechanisms may work synergistically on a sliding scale between the two mechanisms, dependent on the specific analyte-modifier interaction. The data presented for the piperidine, dimethyl-piperidine, and 3-hydroxy-piperidine analytes reflected interactions with a strong Core mechanism component, while the pentamethyl-piperidine data reflected interactions with a strong Façade mechanisms component. While no cluster/dimer ions were demonstrated in FIG. 15, the mass spectra may not provide accurate cluster ion representation and the Core mechanism may have contributed to the overall differential mobility behavior of pentamethyl-piperidine with the drift gas modifiers. The sliding scale model for the two mechanisms can be viewed in relation to the various energetically possible conformations between a specific analyte ion and neutral molecule interaction. In certain circumstances, some compound interactions may favor the Core mechanism, resulting in 90% of the possible conformations leading to the formation of a new cluster ion (Core mechanism), while 10% of the conformations reflect the Façade mechanism. For different compounds the scale may slide towards the Façade mechanism. Other compound interactions may result in only 10% of the conformations having the Façade effect and the other 90% of conformations having no effect at all, indicating that the conformations prevented attraction between the two molecules sufficient for either mechanism.

In one embodiment, Molecular modeling (MM) is employed to investigate and/or predict the Core and Façade mechanisms for the monomer ion equilibrium interactions. Molecular modeling data for global minimum conformation energy and surface volume were collected for various test conditions. Additionally, the monomer analyte ion's change in conformational freedom was determined for each of the five analytes.

For analyte conditions with no drift gas modifier, the MM complex data represents the interaction between one protonated analyte ion and one neutral analyte molecule (dimer ion). For analyte conditions with a drift gas modifier, the MM complex data represents the interaction between one protonated analyte ion and one neutral modifier molecule (analyte-modifier ion). Table 3 provides the MM data, representative of the monomer ion' equilibria complexes, for all study conditions.

TABLE 3

Minimum conformation energy and surface volume values for the proposed monomer ion' equilibrium interactions for various conditions

| | Minimum conformation energy (kcal/mol) | Surface Volume | Change in Conformal Energy |
|---|---|---|---|
| piperidine(+)-piperidine | 6.3 | 7075 | 19.7 |
| piperidine(+)-2-propanol | −16.1 | 6535 | |
| piperidine(+)-2-butanol | −15.3 | 6739 | |
| piperidine(+)-cyclopentanol | −7.2 | 6949 | |

TABLE 3-continued

Minimum conformation energy and surface volume values for the proposed monomer ion' equilibrium interactions for various conditions

| | Minimum conformation energy (kcal/mol) | Surface Volume | Change in Conformal Energy |
|---|---|---|---|
| dimethylpip(+)-dimethylpip | 9.1 | 8623 | 25.8 |
| dimethylpip(+)-2-propanol | −13.7 | 7173 | |
| dimethylpip(+)-2-butanol | −12.9 | 7644 | |
| dimethylpip(+)-cyclopentanol | −4.9 | 7689 | |
| tetramethpip(+)-tetramethpip | 23.1 | 9823 | 25.2 |
| tetramethpip(+)-2-propanol | −6.7 | 7811 | |
| tetramethpip(+)-2-butanol | −1.5 | 8270 | |
| tetramethpip(+)-cyclopentanol | 2.53 | 8343 | |
| pentamethpip(+)-pentamethpip | 45 | 10531 | 25.1 |
| pentamethpip(+)-2-propanol | 10.7 | 8070 | |
| pentamethpip(+)-2-butanol | 12.3 | 8565 | |
| pentamethpip(+)-cyclopentanol | 20.2 | 8576 | |
| 3hydroxypip(+)-3hydroxypip | −29.7 | 7348 | 24.5 |
| 3hydroxypip(+)-2-propanol | −31.9 | 6529 | |
| 3hydroxypip(+)-2-butanol | −30.2 | 7178 | |
| 3hydroxypip(+)-cyclopentanol | −22.5 | 7050 | |

Notable is the correlation between the dimer ion minimum conformation energy values in Table 3 and the actual MS dimer ion signal intensity percentages shown in FIG. 8. In order to investigate the effect that a Façade interaction may have on changing an analyte ion's differential mobility behavior, the potential for restriction of the monomer ion's conformational freedom has to be determined. This is represented by calculating the change in surface volume between the global minimum conformation of the monomer ion alone and the surface volume of the superimposed eight lowest energy conformations of the monomer ion.

Figure 17:
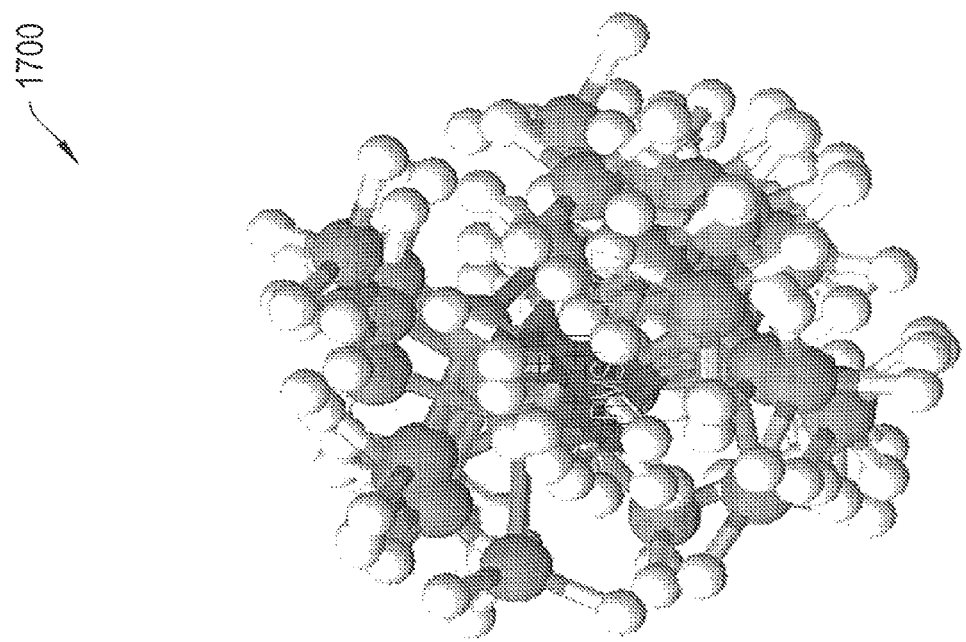
FIG. 17 is an exemplary view of the charge in conformational freedom visual representation for tetramethyl-piperidine monomer ion including the minimum energy conformation and superimposed eight lowest energy conformations.
Figure 17:
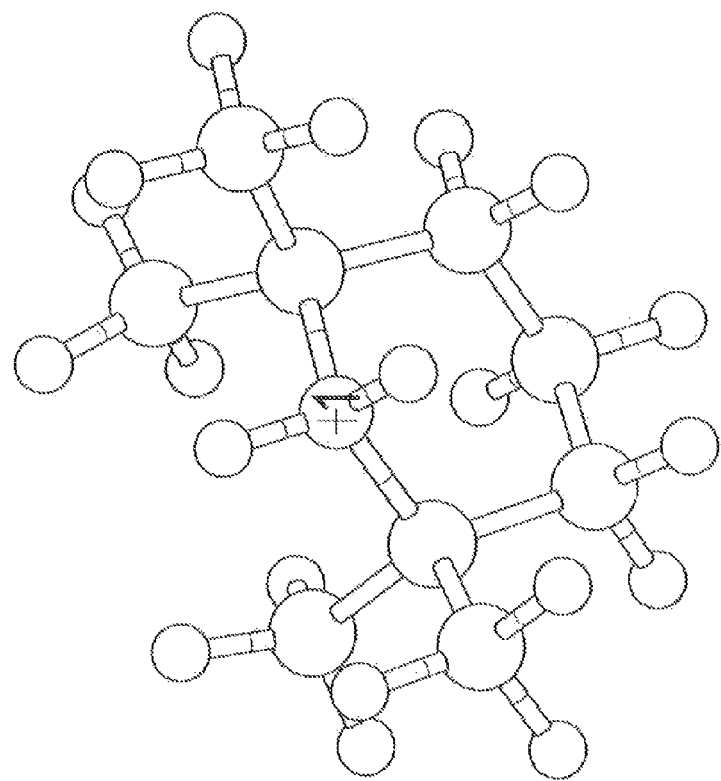
Figure 18A:
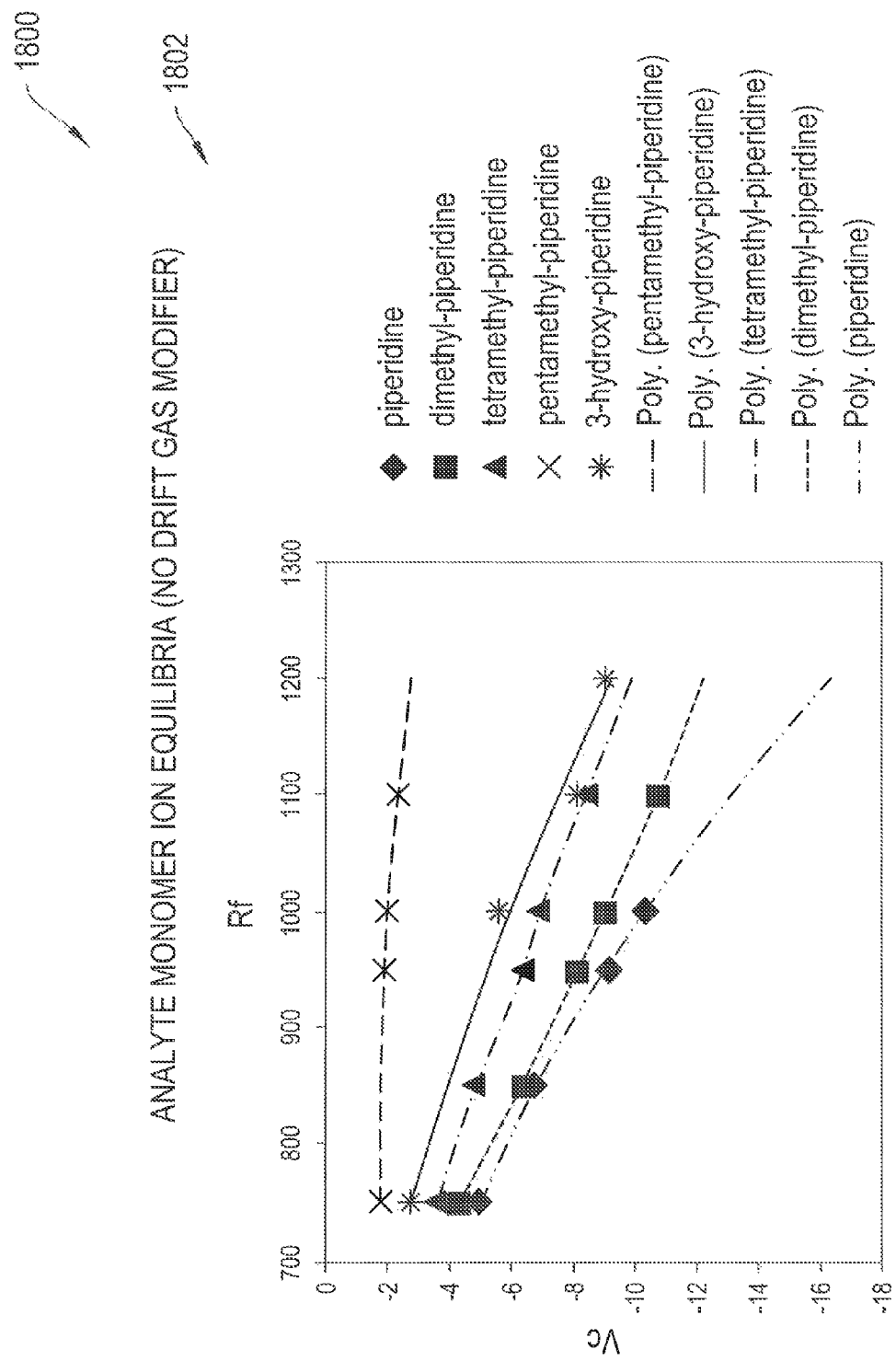
FIG. 18 is a combined graphic view of various monomer ion equilibrium plots of Rf versus Vc under various conditions.
Figure 18B:
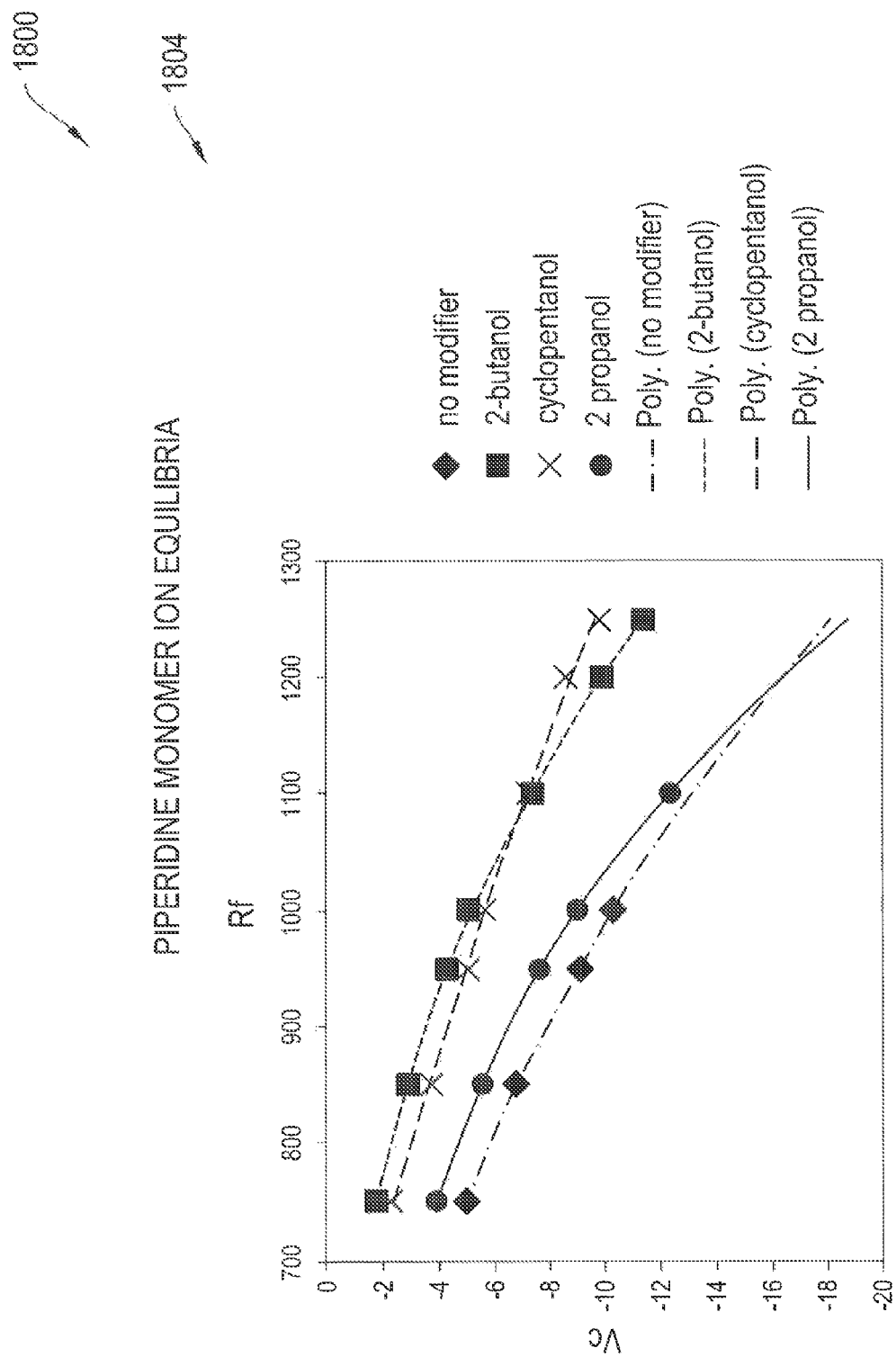
Figure 18C:
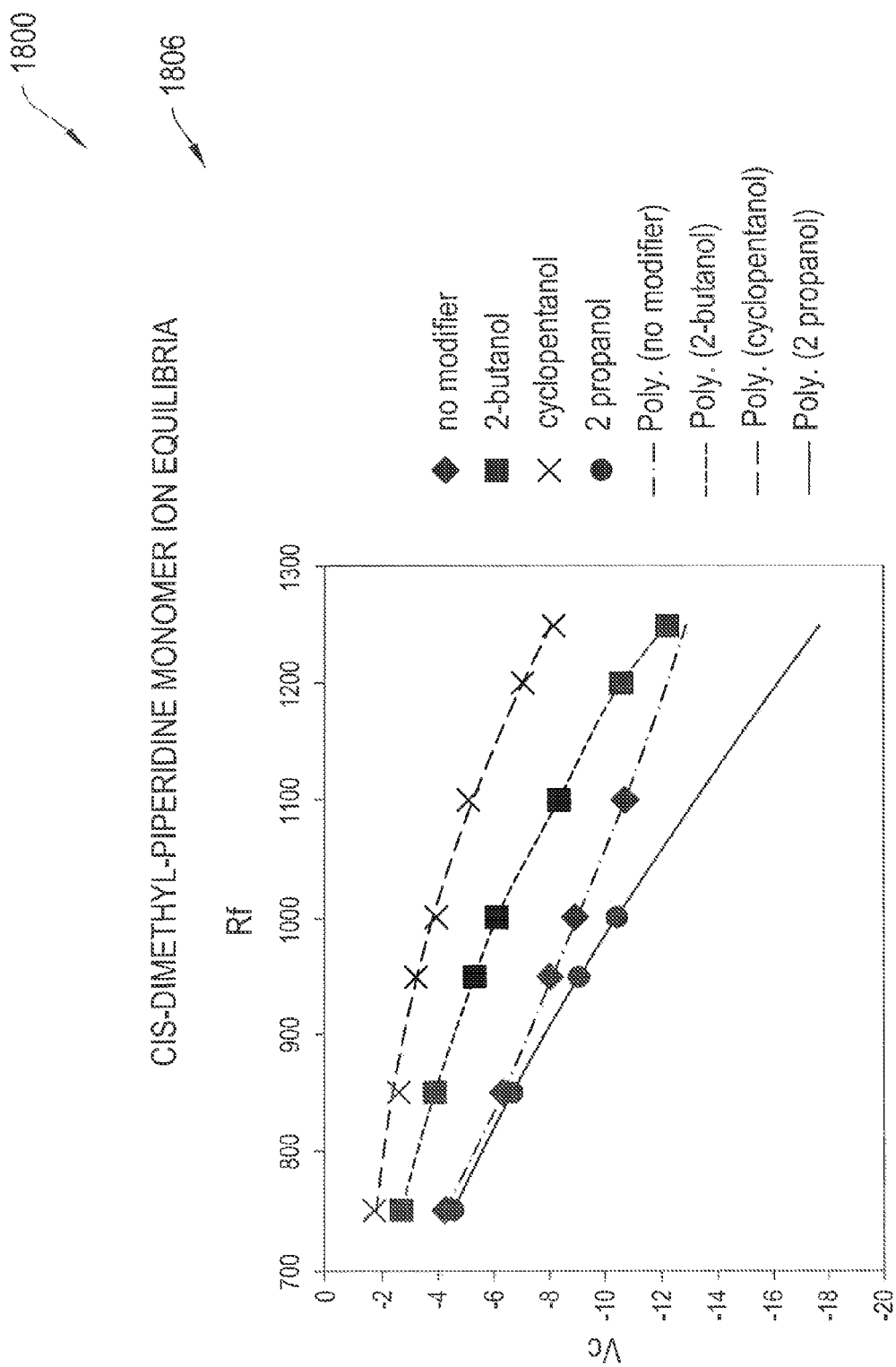
Figure 18D:
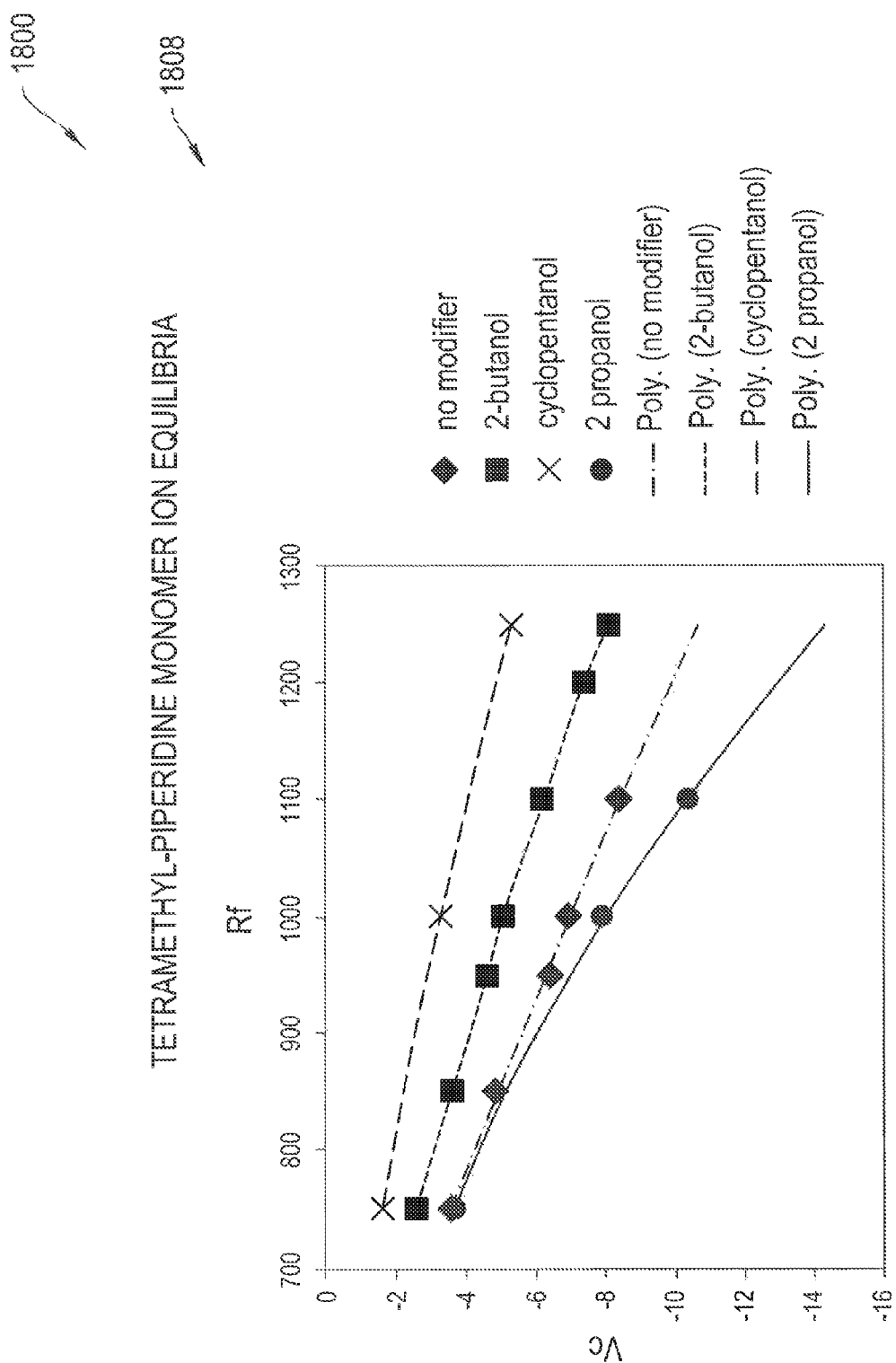
Figure 18E:
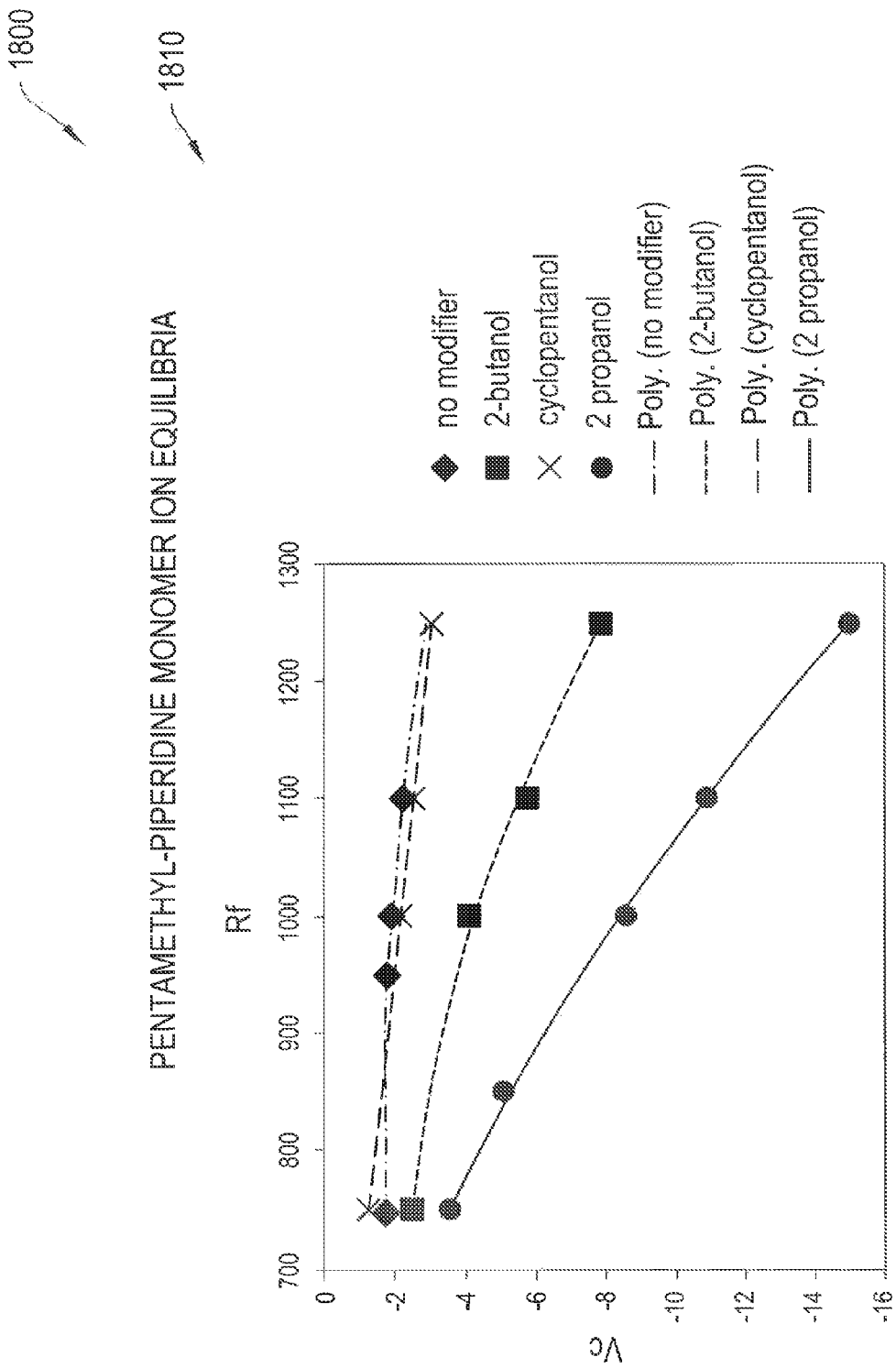
Figure 18F:
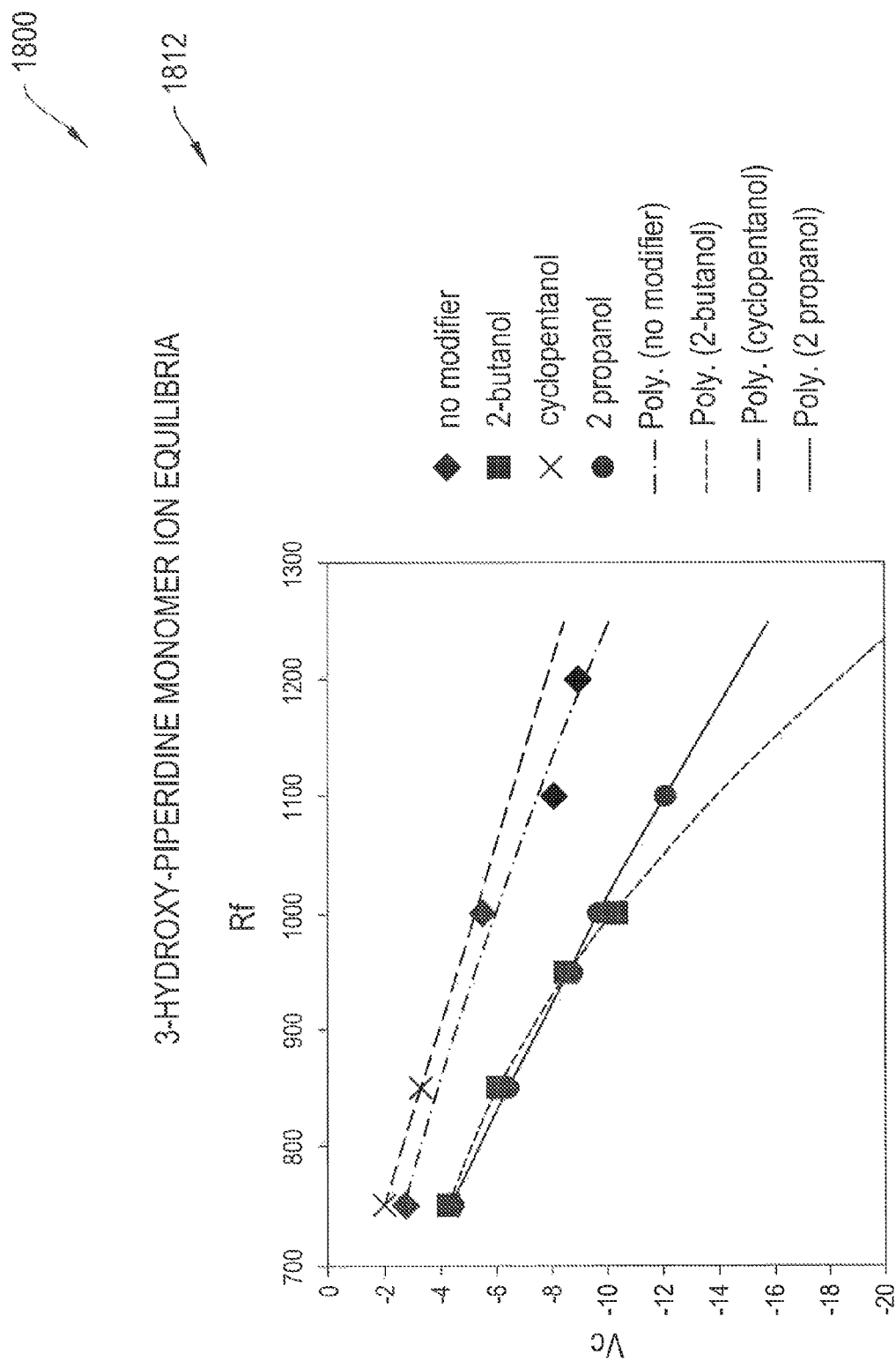

FIG. 17 is an exemplary view 1700 that shows the minimum conformation of the tetramethyl-piperidine monomer ion as well as the superimposed eight lowest energy conformations of the tetramethyl-piperidine monomer ion. The calculated percent change in surface volume for all five analyte monomer ions is reported in Table 3 in terms of the change in conformational freedom (displayed in the dimer ion row for each analyte).

As described previously, the DMS dispersion plots, DMS spectra, and mass spectra for various Rf and Vc settings were used to accurately identify the monomer and dimer ion' equilibria Vc point positions for various Rf settings. Based on this data, Rf versus Vc plots were generated for each test compound and drift gas modifier condition. A second order polynomial trend line was calculated and included in the plots for each condition.

FIG. 18 is a combined graphic view 1800 of various monomer ion equilibrium plots of Rf versus Vc under various conditions. FIG. 18 demonstrates the plots for various monomer ion' equilibria generated by the ESI-DMS-MS system 200. Plot 1802 compares the differential mobility behavior of the five test analytes when no drift gas modifiers were used. Plot 1804 demonstrates the differential mobility behavior for piperidine monomer ion equilibria with and without the three different drift gas modifiers. Plots 1806, 1808, 1810, and 1812 show the differential mobility behavior for the four other analyte monomer ion equilibria with and without the three drift gas modifiers. Table 3 demonstrates that piperidine, due to its lack of side chains, has the smallest change in conformational freedom of all five analyte monomer ions. This would indicate that the potential for Façade mechanism interactions to decrease the effective cross sectional area of the piperidine monomer ion' equilibrium is less than for all of the other analytes. This potentially explains a monomer Vc point shift to a greater Vc value for dimethyl-piperidine and tetramethyl-piperidine with the 2-propanol modifier but not for piperidine with the same modifier. The combined effects of the Façade and Core mechanisms provide an overall decrease in the cross sectional area for the monomer ion' equilibrium of dimethyl-piperidine and tetramethyl-piperidine with the 2-propanol modifier. However, the reduced potential for the Façade mechanism effect in the piperidine monomer ion' equilibrium, results in a more dominant Core mechanism effect.

Dimer Ion' Equilibrium

As discussed previously herein, two dimer ion formations have been observed, reflecting the dimer ion presence in both a "dimer ion Vc point" and "monomer ion Vc point". It is presumed that the shared proton dimer structure shown in FIG. 10B corresponds to the dimer Vc point. It is proposed that this dimer structure is not easily dissociated in the DMS filter 210 electric field and fosters clustering with other molecules.

Figure 19:
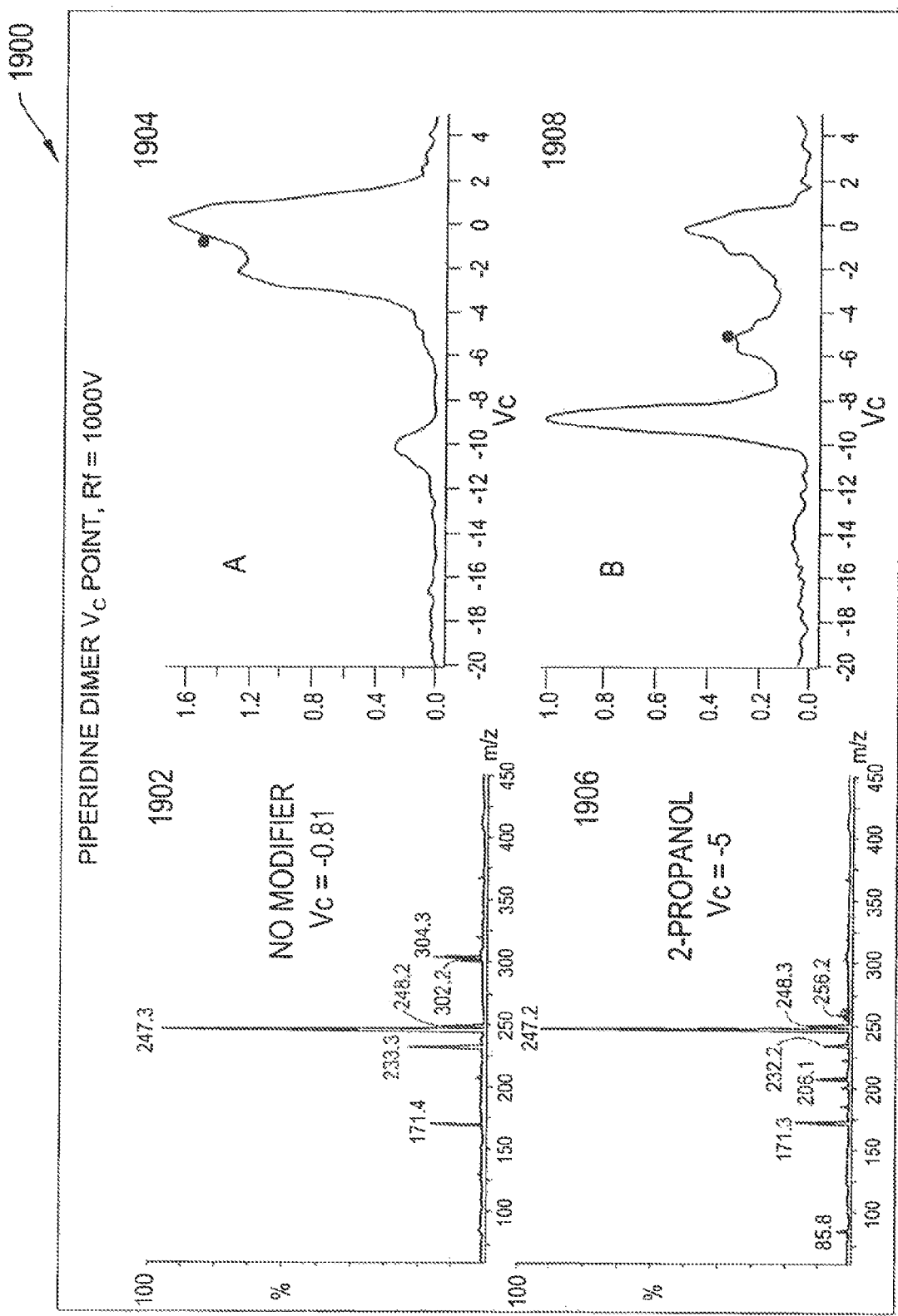
FIG. 19 is a combined graphic view of the DMS spectra for piperidine dimer at an Rf=1000 volts with no modifier and associated mass spectrometric spectra and the DMS spectra with a 2-propanol modifier and associated mass spectrometric spectra.

FIG. 19 is a combined graphic view 1900 of the DMS spectra 1904, highlighting the dimer Vc point positions, for piperidine dimer at an Rf=1000 volts with no modifier and associated mass spectrometric spectra 1902 and the DMS spectra 1908, highlighting the dimer Vc point positions, with a 2-propanol modifier and associated mass spectrometric spectra 1906. The use of the 2-propanol drift gas modifier provides a shift in the dimer Vc point position to a larger Vc, reflecting a decrease in the overall cross sectional area of the dimer ion' equilibrium. The m/z 171 ion is the shared proton piperidine dimer ion $[C_5H_{11}N+H^++C_5H_{11}N]^+$. The other ions present in the mass spectra 1902 and 1906 are possibly dimer based adduct ions contributing to the dimer ion' equilibrium or independent ions with similar differential mobility behavior as the piperidine dimer ion' equilibrium.

Figure 20:
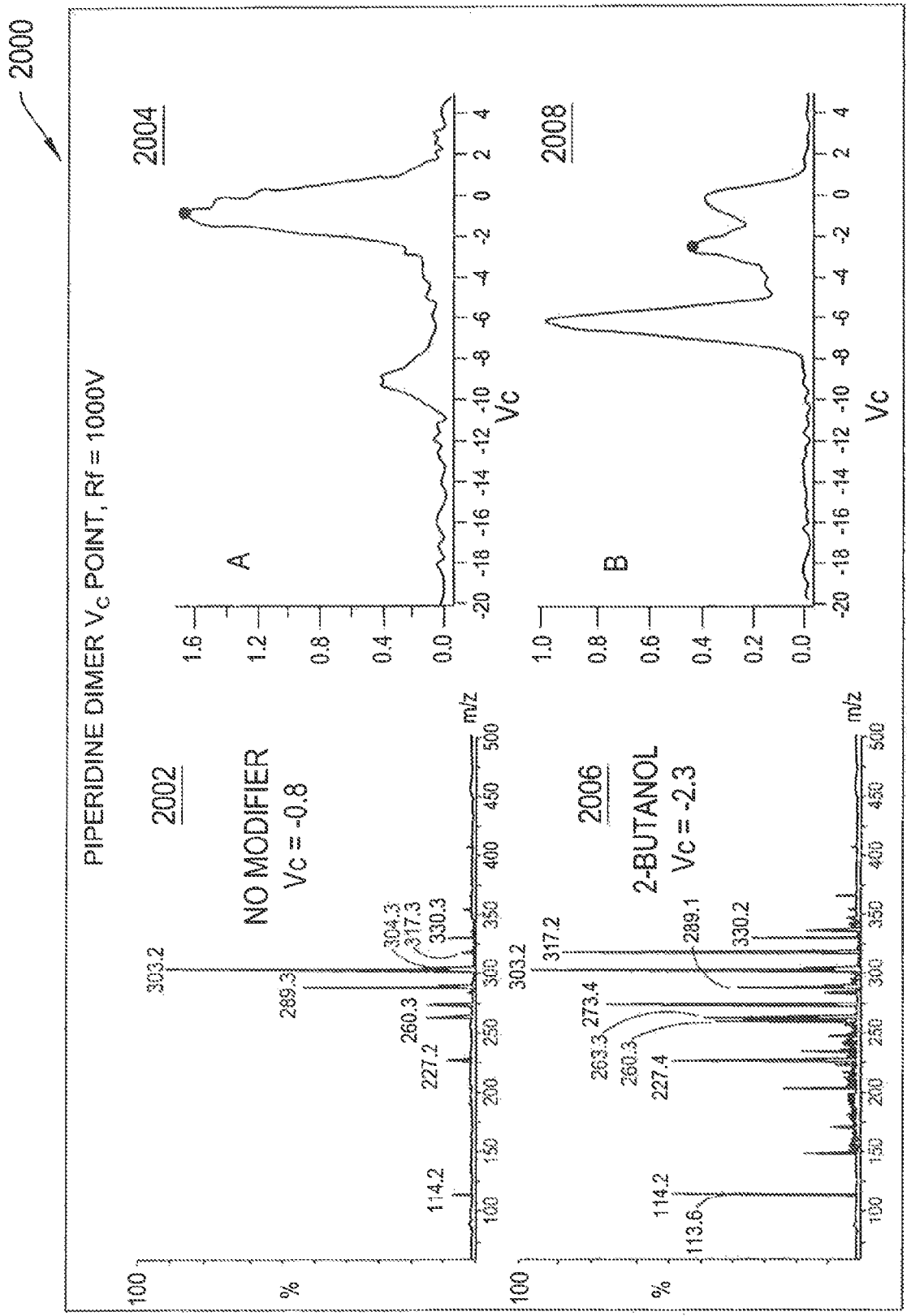
FIG. 20 is a combined graphic view of the DMS spectra for Dimethyl-piperidine dimer at an Rf=1000 volts with no modifier and associated mass spectrometric spectra and the DMS spectra with a 2-butanol modifier and associated mass spectrometric spectra.

FIG. 20 is a combined graphic view 2000 of the DMS spectra 2004, highlighting the dimer Vc point positions, for Dimethyl-piperidine dimer at an Rf=1000 volts with no modifier and associated mass spectrometric spectra 2002 and the DMS spectra 2008, highlighting the dimer Vc point positions, with a 2-butanol modifier and associated mass spectrometric spectra. The m/z 227 ion is the shared proton dimethyl piperidine dimer ion $[C_7H_{15}N+C_7H_{15}N+H^+]^+$. As is the case with piperidine, the addition of the drift gas modifier results in a dimer Vc point shift to a greater Vc. For both piperdine and dimethyl-piperidine, no dimer-modifier adduct ions are present in the mass spectra 2002 and 2006. However, at the dimer Vc points of both analytes, without any modifier, the presence of a dimer+62 m/z ion and dimer+76 m/z ion are shown.

For piperidine, these ions correspond to the m/z 233 and 247 ion peaks, whereas for dimethyl-piperidine correspond to the m/z 289 and 303 ion peaks. Both of the analytes dimer Vc points contain ions with the same mass difference, indicating that these are adduct/cluster ions containing the dimer. For both piperidine and dimethyl piperidine, the addition of the drift gas modifier decreases the intensity of the cluster ions with respect to the dimer ion, reflecting a reduction in clustering through the use of the modifier.

In certain circumstances, the reduced clustering results in a decrease to the dimer ion' equilibria effective cross sectional area, resulting in a dimer Vc point shift towards a larger Vc. Although the underlying interaction mechanism(s) taking place is not clear, it appears that a core type mechanism may be taking place, but the dimer-modifier adduct ions are just not visible in the mass spectra. Alternatively, the Façade type interaction may be dominating where the modifier disrupts the clustering and/or reduces the conformational freedom of the dimer ion. Regardless of the mechanism(s), the only drift gas modifier effect on the differential mobility behavior for all analyte dimer ion' equilibria, was a shift towards a larger Vc.

Figure 21A:
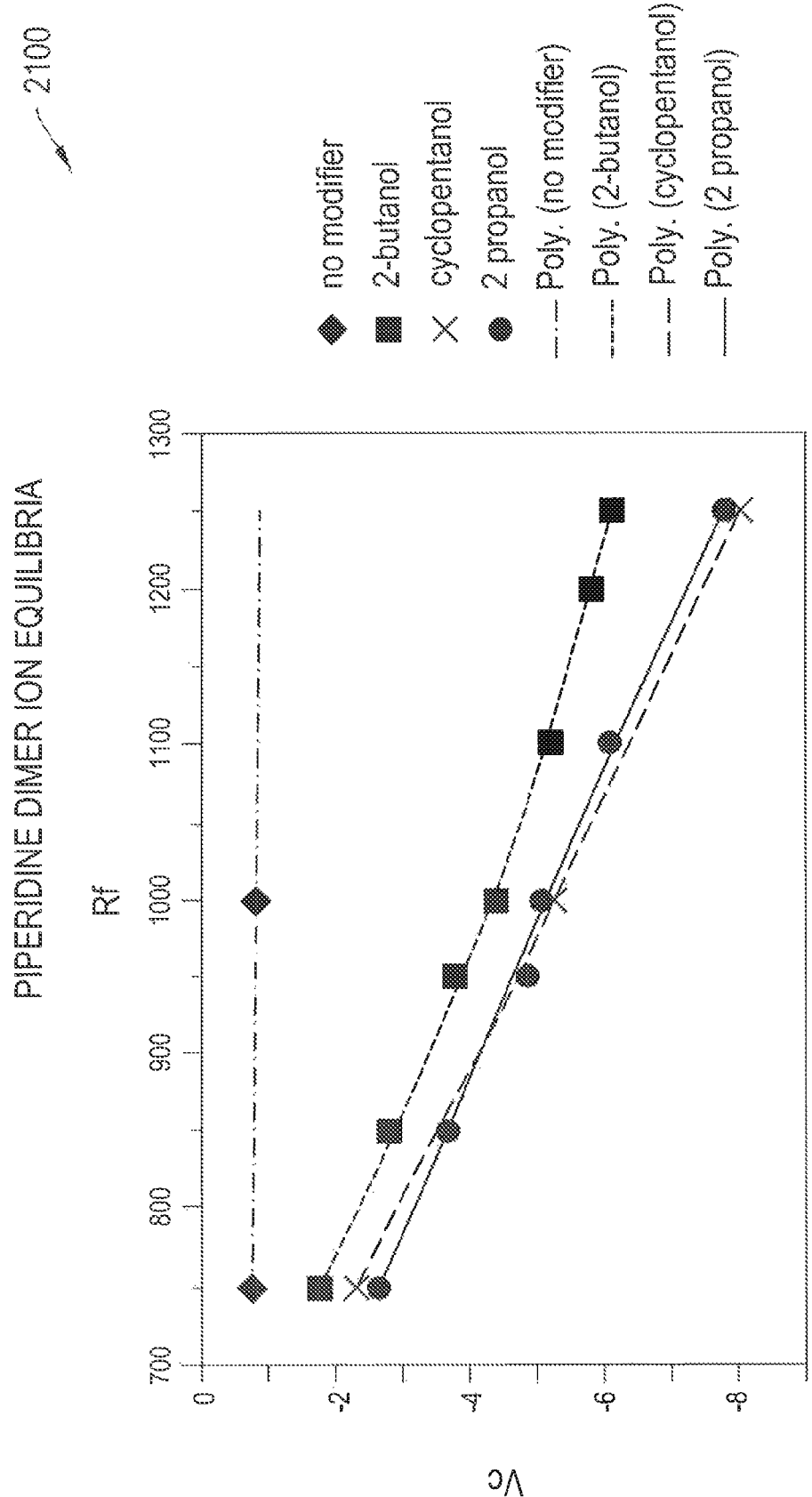
FIG. 21A is a Rf versus Vc plot of the piperidine dimer ion equilibrium under various conditions.
Figure 21B:
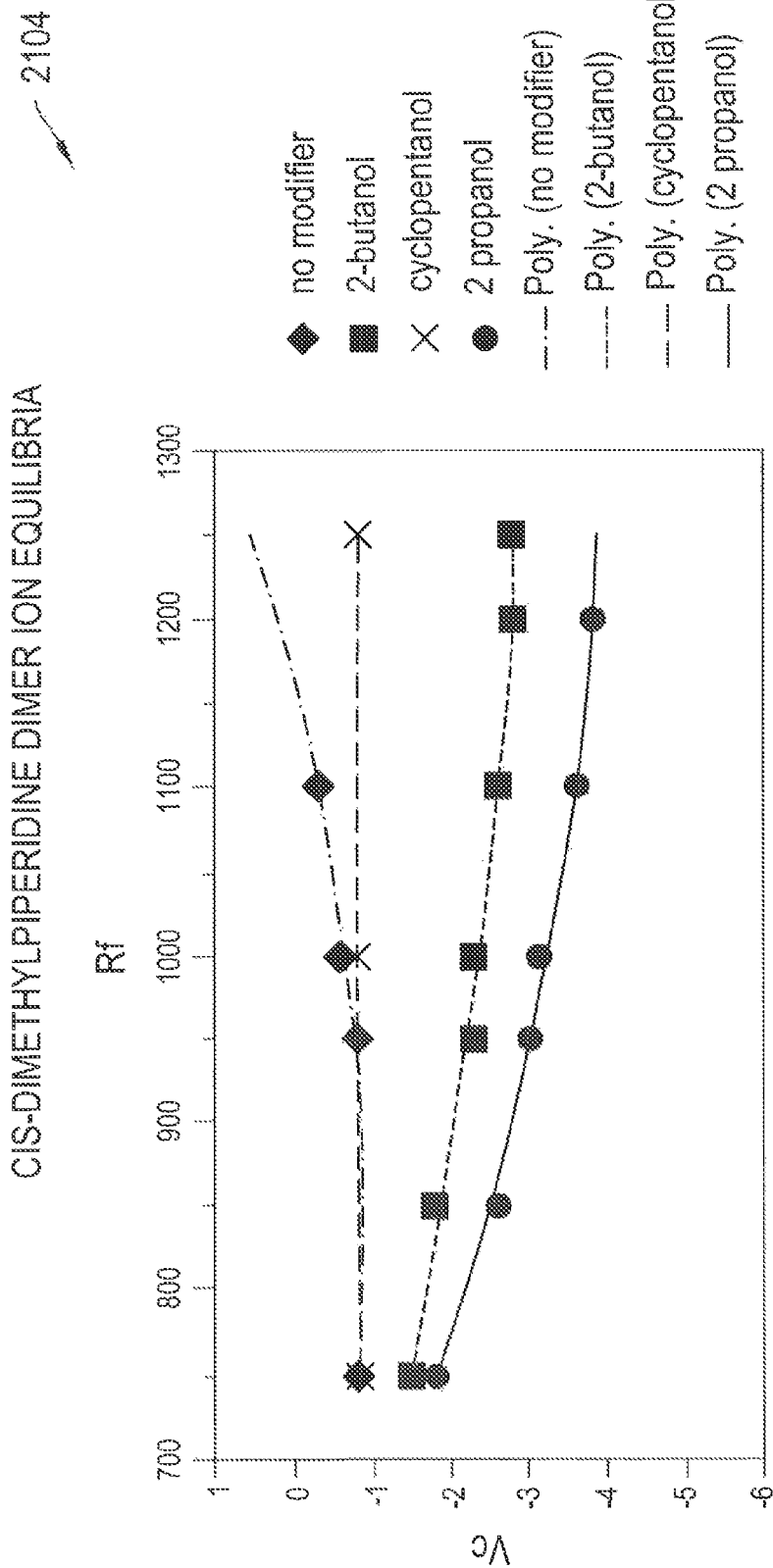
FIG. 21B is a Rf versus Vc plot of the Cis-dimethylpiperidine dimer ion equilibrium under various conditions.
Figure 21C:
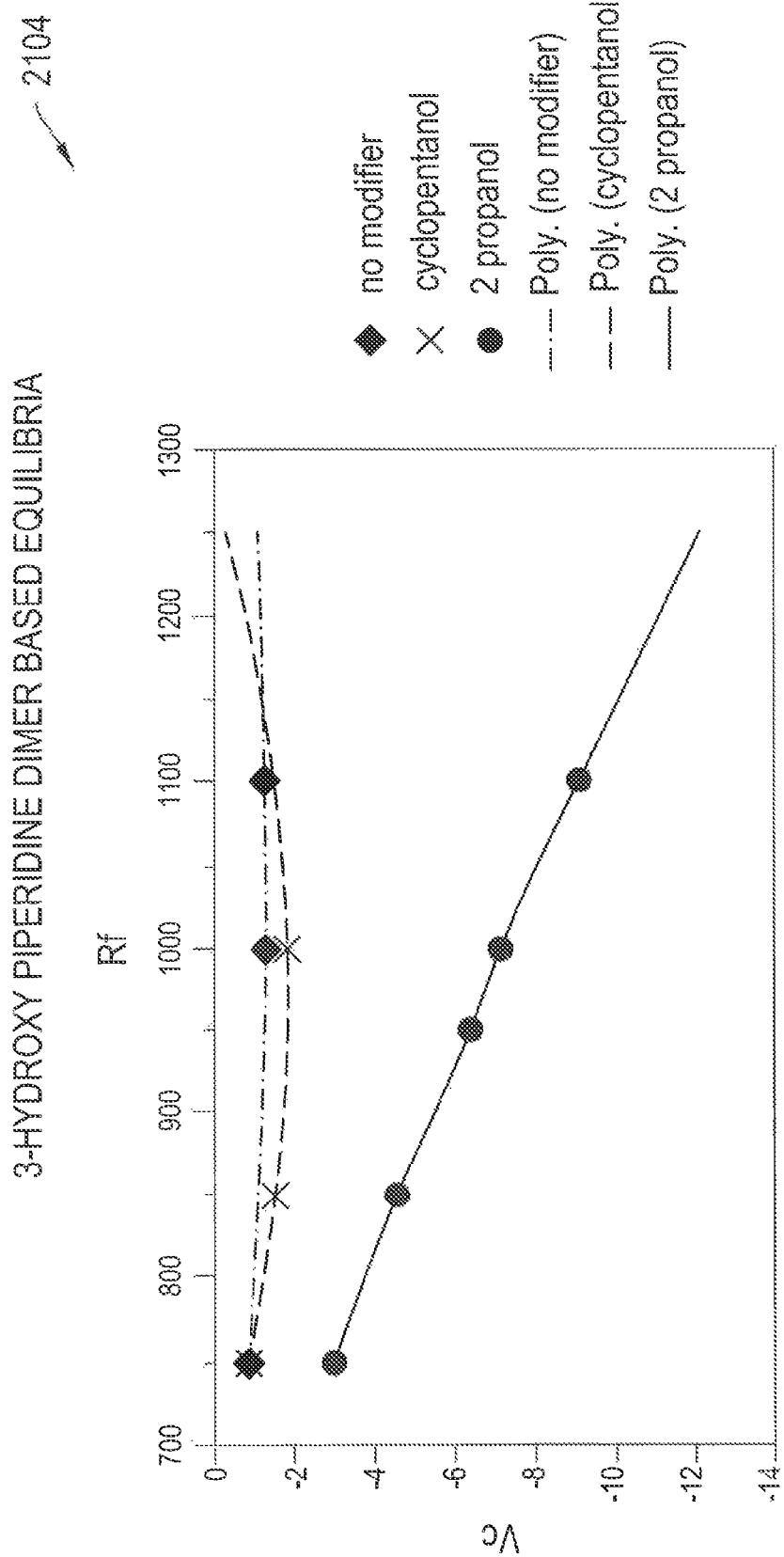
FIG. 21C is a Rf versus Vc plot of the 3-Hydroy piperidine dimer ion equilibrium under various conditions.

FIG. 21A is a Rf versus Vc plot 2100 of the piperidine dimer ion equilibrium under various conditions. FIG. 21B is a Rf versus Vc plot 2102 of the Cis-dimethylpiperidine dimer ion equilibrium under various conditions. FIG. 21C is a Rf versus Vc plot 2104 of the 3-Hydroy piperidine dimer ion equilibrium under various conditions. Under certain conditions, these three analytes were capable of generating enough dimer ion signal to detect and track the shifts for the dimer ion' equilibria. As shown in FIG. 21C, no dimer ion' equilibrium was present for the 3-hydroxy-piperidine with 2-butanol condition due to lack of MS analyzer 240 dimer ion signal.

DMS has demonstrated successful gas phase ion separation at atmospheric pressure for various types of compounds, enabling its use in many areas of chemical/biological analysis. However, desired separations are not always optimal. One of the fundamental ways in which analyte separation can be altered is by changing the pure bulk medium (drift gas) within which the separation is taking place, or using modified gas compositions.

In certain embodiment, the ESI-DMS-MS system 200 employs the Core and Façade mechanisms as key factors effecting the change in an analyte ion's differential mobility behavior through the use of drift gas modifications, as well as for compensating the quantization of certain ion species based on the nature of DMS filter 210 ion separation through, for example, molecular modeling of the ion species. The modeling may be performed, for example, by a software application and/or algorithm within a memory and/or database that is executed by the controller 242. In one embodiment, the data generated through molecular modeling of the proposed mechanisms provides support for describing the observed DMS analyte Vc point shifts and applying these observed shifts to later sample analysis within the ESI-DMS-MS system 200. More particularly, the molecular modeling data may enable the ESI-DMS-MS system 200 or any like DMS-MS system to predict how certain analyte ions would respond to various drift gas modifications or to predict certain equilibrium conditions between the DMS sensor and MS analyzer 240, and, thereby, compensate for and/or interpolate a more accurate quantity of certain ions of a sample. Such predictions may be based on empirical data and/or experimental observations for certain ion species. Other predictive tools may be based on one or models of the behavior of certain ions within the ESI-DMS-MS system 200.

In review, one aspect of the invention is directed to an ESI-DMS-MS combination system, which employs enhanced modeling techniques to compensate for effects of competitive ion suppression and, thereby, provide better sample resolution and quantization. The ESI-DMS-MS system may also employ enhanced predictive separation control based on predictive modeling of various gas phase molecular interactions for certain analytes of interest. The ESI-DSM-MS system may employ molecular modeling to predict the influence of drift gas modifications on analyte ion separation and, thereby, interpolate or estimate the actual quantity of a particular analyte within a sample more accurately. Such predictive modeling, in certain embodiments, may be applied to analyzing samples including constituent identification. The molecular modeling may enable the altering or controlling of an analyte ion's differential mobility behavior based on gas phase molecular clustering interactions.

The molecular model, in one feature, accounts for the influence of chemical structure, conformational freedom, H-bonding, electrostatic attraction, and steric repulsion on gas phase interactions and the mechanisms by which they alter an analyte ion's differential mobility behavior. More particularly, two gas phase interaction mechanisms, e.g., the Core and Façade mechanisms, are employed which detail drift gas modifier effects on analyte ion differential behavior.

According to one aspect, the invention provides a sample analysis system having at least one ion mobility based analyzer. The ion mobility based analyzer includes an ion mobility based filter for generating a time-varying electric field and compensation field through which ions of the sample flow along a flow path. The ion mobility based analyzer also includes an ion mobility based detector for detecting a first portion of the ions in the flow path. The sample analysis system also includes at least one mass analyzer for detecting a second portion of the ions delivered from the at least one ion mobility based analyzer. The sample analysis system further includes a controller for generating a first spectra associated with the first portion of ions and generating a second spectra associated with the second portion of ions.

In one feature, the controller is configured for generating a first standard spectrum based on the ion mobility of at least one known ion species. In another feature, the controller is configured for generating a second standard spectra based on the mass-to-charge ratio of at least one known ion species. In one configuration, a data store stores a set of conditions associated with at least one ion intensity peak of the standard spectra.

The set of conditions may include a time-varying voltage or a compensation voltage for at least one ion mobility based filter. At least one ion mobility based filter may be a differential mobility spectrometer or an ion mobility spectrometer. The set of conditions may also include, without limitation, a type of dopant, a concentration of a dopant, pressure, temperature, flow rate, or mass analyzer voltages associated with generating the first and second spectra.

In one configuration, the controller is configured for comparing the first spectra to the first standard spectra to identify at least one ion species. In another configuration, the controller is configured for comparing the second spectra to the second standard spectra to identify at least one ion species.

In a further configuration, the controller is configured for integrating the area of at least one ion intensity peak of the second spectra associated with at least one ion species to quantize at least one ion species in the sample. The controller may then match at least one ion intensity peak of the second spectra with a known standard spectra of a known ion species and adjust the ion species quantization based on a predicted deviation of the quantization of the known ion species under similar conditions. The predicted deviation may be based, at least in part, on certain molecular modeling. The molecular modeling may include at least one of a Core and Façade mechanism or a combination of both.

In one feature, the sample analysis system includes at least one electrospray ionization source. The electrospray ionization source may include a direct infusion ionization source. In another feature, the ion mobility based analyzer and mass analyzer are micromachined and included in an integrated circuit package. In a further feature, the ion mobility based analyzer, mass analyzer, and electrospray ionization source are included in an integrated circuit package. In yet another feature, the ion mobility based analyzer and electrospray ionization source are included in an integrated circuit package. In one configuration, the sample analysis system includes an interface for detachably connecting the integrated package to the mass analyzer.

Figure 22:
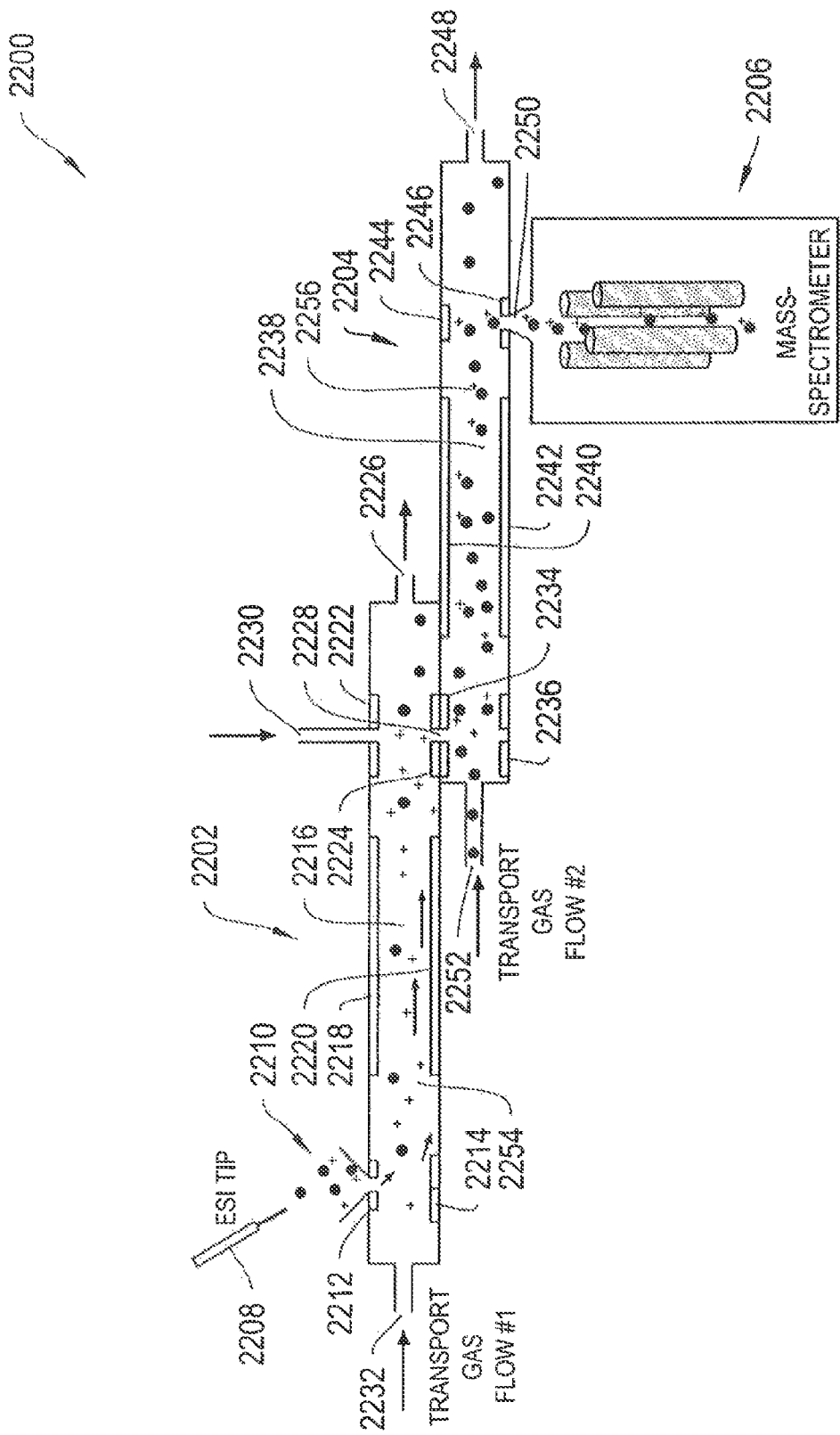
FIG. 22 is a conceptual diagram of an ESI-DMS-DMS-MS system according to an illustrative embodiment of the invention.

FIG. 22 is a conceptual diagram of an ESI-DMS-DMS-MS system 2200 according to an illustrative embodiment of the invention. The system 2200 includes a first DMS analyzer 2202, a second DMS analyzer 2204, and a MS 2206. The first DMS analyzer 2202 includes an ESI tip 2208, sample inlet 2210, directing electrodes 2212 and 2214, a DMS filter 2216, filter electrodes 2218 and 2220, detector and/or director electrodes 2222 and 2224, exhaust 2226, outlet 2228, director gas inlet 2230, transport gas inlet 2232, flow path 2254. The second DMS analyzer 2204 includes directing electrodes 2234 and 2236, a DMS filter 2238, filter electrodes 2240 and 2242, detector and/or director electrodes 2244 and 2246, exhaust 2248, outlet 2250, transport gas inlet 2252, and flow path 2256.

In operation, ESI tip 2208 generates ions from a liquid sample that are directed into the first DMS analyzer 2202 at least in part by director electrodes 2210 and/or 2214. In certain embodiments, one or both director electrodes 2210 and 2212 include an orifice or opening through which ions may pass. Once the ions reach the flow path 2254 of DMS analyzer 2202, the ions are transported by a transport gas from transport gas inlet 2232 through the DMS filter 2216. Adjustable asymmetric and compensation fields between filter electrodes 2218 and 2220 enable the DMS filter 2202 to selectively allow an ion species to pass through the filter 2202 while neutralizing other ion species. In one embodiment, the Vrf and Vc of the DMS filter 2202 are set to allow a particular ion species having a particular conformation to pass through the DMS filter 2202. A director gas may be introduced via inlet 2230 to direct ions exiting the filter to the outlet 2228. The electrodes 2222 and 2224 may function as detector electrodes, director electrodes, and/or both detector and director electrodes. In one embodiment, the electrodes 2222 and 2224 direct, at least in part, the ions exiting the DMS filter 2216 from the first DMS analyzer 2202 through the outlet 2228 and into the second DMS analyzer 2204. The exhaust 2226 exhausts neutrals or other interferents from the first DMS analyzer 2202.

The second DMS analyzer 2204 receives the selected ions from the first DMS analyzer 2202 via the outlet 2228. The director electrodes 2234 and 2236 may direct, at least in part, the ions from the outlet 2228 into the flow path 2256 of the second DMS analyzer 2204. A transport gas inlet 2252 may introduce a transport gas into the flow path 2256 to enable transport of ions through the DMS filter 2238. In one embodiment, one or more dopants are introduced via the transport gas inlet 2252 to manipulate the ions in the flow path 2256 and affect the separation of ions in the DMS filter 2238. The concentration of the dopant or dopants may vary to optimize the separation of the ions. In another embodiment, one or more ligands are introduced via the transport gas inlet 2252 to manipulate and/or affect the conformation of the ions in the flow path 2256. In one embodiment, the frequency and/or magnitude of Vrf is adjusted to affect the conformation of the ions in the flow path 2256. In certain embodiments, a process is configured to regulate or adjust of one or more conditions of the flow path, such as the amount and/or type of dopant, amount and/or type of ligands, magnitude and/or frequency of Vrf, temperature, pressure, flow rate, and other conditions in the flow path to manipulate the conformation of the ions of an ion species in the second DMS analyzer 2204. Once certain ions are manipulated and/or their conformation is altered, the DMS filter 2238 may then further separate different conformations of the ions in the flow path or channel 2256 because the different conformations will have different ion mobility characteristics.

Once the conformation of a particular ion species is manipulated in the DMS filter 2238, the conformation exiting the DMS filter 2238 is directed to the outlet 2250. Electrodes 2244 and 2246 may function a detector electrodes, director electrodes, or both detector and director electrodes. In one embodiment, the outlet 2250 is in communication with an MS 2206 to enable detection of the ions exiting the DMS analyzer 2204. In certain embodiments, the second DMS analyzer 2204 enables the filtration and analysis of various conformations of a particular ion species which are then delivery to the MS 2206 for detection. In a further embodiment, a second MS may be in communication with the MS 2206 to enable further analysis of the ions. In one embodiment, the dual channel DMS system 2206 enables separation of protein isomers and subsequent manipulation of their conformers in the gas phase by electric field or chemical modifiers or other conditions.

Figure 23:
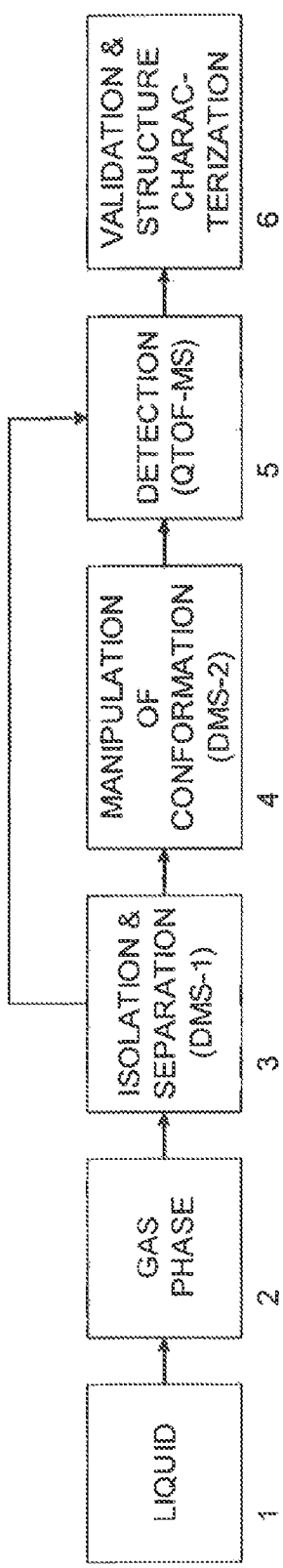
FIG. 23 is a flow chart of a process for analyzing ions according to an illustrative embodiment of the invention.

FIG. 23 is a flow chart of a process 2300 for analyzing ions according to an illustrative embodiment of the invention. In one embodiment, the inventive system of FIG. 22 and methodology enables rapid on-line manipulation of conformation, isolation and the characterization of the physical and chemical properties of individual proteins produced by electrospray ionization. In certain embodiments, Protein ions are formed and characterized using the following sequence of steps. First, a liquid sample is converted to gas phase ions using an ESI tip 2208 (Step 1). Then, the gas phase ions are delivered to a first DMS analyzer 2202 (Step 2). Then, for example, the system 2200 uses the first DMS analyzer 2202 in its dual DMS system to separate and isolate a specific protein conformer from an isomeric mixture (Step 3). After, the system 2200 uses the DMS analyzer 2204 for the manipulation and characterization of the physical and chemical properties of a single specific protein conformer via the use of dopant mixtures, ligands, electric fields, temperature, pressure, flow rate, and/or other conditions of the second DMS analyzer 2204 (Step 4). The system 2200 then further analyzes selected analytes from the second DMS analyzer 2204 using a quadrupole-time of flight mass spectrometer, e.g., MS 2206 (Step 5). The system 2200 may optionally use the MS 2206 for detection of ions from the first DMS analyzer or use one or both electrodes 2222 and 2224 for ion detection if desired. Further details on the design and construction of DMS-DMS-MS system 2200, methods for manipulation of protein conformation, rationale for protein selection and principles of separation of conformers and conformer complexes in a DMS are provided later herein.

Figure 24:
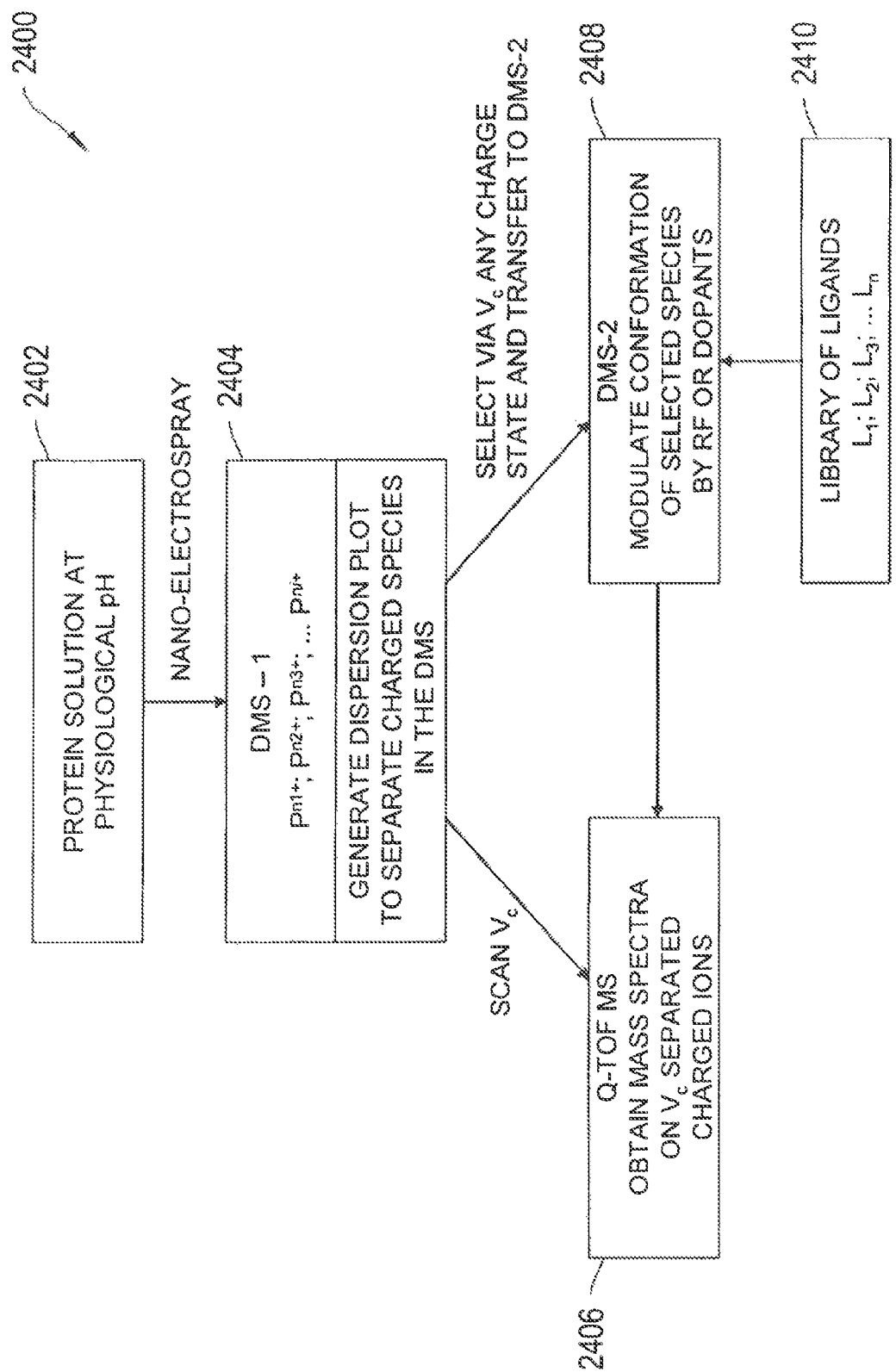
FIG. 24 is another flow chart of a process for analyzing ions according to an illustrative embodiment of the invention.

FIG. 24 is another flow chart of a process 2400 for analyzing ions according to an illustrative embodiment of the invention. As described previously, the invention includes a methodology for modulation of protein conformations in real-time and for characterizing their chemical and physical properties. One exemplary experimental approach is outlined in the flow diagram of FIG. 24. Briefly, the following sequence of steps may be performed. Referring to system 2200 of FIG. 22, the individual steps are further summarized as follows:

Introduction of protein sample at a physiological pH into a first DMS analyzer 2202 (Step 2402).

Generation of a dispersion plot (spectra for vs. RF voltage) separating the protonated species of the conformer(s) in the solution in DMS analyzer 2202 (Step 2404).

Configuration I—Acquisition of mass spectra of Vc selected bands (ion tracks in dispersion plots) (Step 2406).

Configuration II—Introduction of Vc/RF-selected individual conformers into a second DMS analyzer 2204 and manipulation of conformation of selected protein ion(s) by varying RF field or introduction of ligands or other conditions (Step 2408).

Introduction of libraries of ligands to assess propensity of conformers for selective binding and activity to ligands (toxins) (Step 2410).

Analysis of non-covalent complexes by MS/MS measurements.

We discuss next in more detail each one of the above steps.

System Operation for Isolation and Manipulation of a Single Protein (a) Protein containing solutions will be delivered to the nano-spray needle, e.g., ESI tip 2208 and sprayed on entrance 2210 of the first channel or flow path 2254.

(b) Protein ions formed in gas phase may have a charge state distribution related to protein conditions in liquid phase. In one embodiment, the system 2200 uses protein conformations which are represented in physiological conditions.

(c) Protein ions may be separated in the first channel or flow path 2254 of DMS analyzer 2202 based on compound (or conformer)-dependent changes in mobility. As discussed above, in one embodiment, a DMS analyzer 2202 in conjunction with an ESI source 2208 is able to separate and analyze different protein conformers that are co-populated in solution.

(d) In one embodiment, the process of ion separations in a miniature DMS, e.g., DMS analyzer 2204, takes a few milliseconds and occurs in a continuous mode (for specific combination of Vrf and $V_C$ voltages) which provides the conditions for on-line gas phase conformer separation.

(e) In certain embodiments, separated ions are injected into the second channel or flow path 2256 associated with the DMS analyzer 2204. The efficiency of ion injection from first channel 2254 to second channel 2256 may be dependent on the deflector potential of, for example, electrodes 2222 and/or 2224. Under certain conditions, only approximately 20 volts DC deflector potential are required to reach approximately 60-70% efficiency of transmission. In another embodiment, computer modeling shows that up to 90% efficiency is possible.

(f) Mass spectral corroboration using MS 2206 of the protein which was manipulated and analyzed in dual channel DMS system 2200.

(g) Capability for rapid switching between positive and negative ion selection and MS 2206 detection mode which provides additional power for protein characterization. Thus (if needed) the system 2200 may concurrently monitor proteins that may exhibit distinct features as negatively charged ions and positively charged ions.

In certain embodiments, the system 2200 provides:

a) Regulation of intensity of high frequency RF voltage (Vrf), allowing manipulation of protein conformations. The effect of RF amplitude on protein conformation may be visualized by observing the dispersion plot patterns.

b) By regulation of transport gas velocity, the residence time of protein ions may be adjusted in the analytical gap between the DMS filter electrodes, and consequently, the system 2200 may obtain information on the kinetics of protein transformation.

c) The system 2200 allows for the quick change of modifiers and, consequently, evaluation of the activity of selected conformers toward selected chemical agents (modifiers).

d) The miniature size of the DMS analyzers (e.g., about the size of a dime or smaller) simplifies temperature control of gas media in analytical gap.

e) By regulation of the exhaust gas stream, the system 2200 may adjust, regulate, and/or change the pressure in analytical gap, which may help optimize the conditions for modulation of conformation of selected proteins.

f) The system may include a controller and/or process that regulations the pH of the condensed phase to control protein conformation in the condensed phase prior to ionization and evaporation of protein samples.

In one embodiment, a novel feature of this dual DMS-DMS-MS system 2200 is that, prior to their introduction into second DMS analyzer 2204, conformational isomers are separated and then injected into the second channel 2256. All other ion species are neutralized and consequently transported with the gas flow to the exhaust 2226 of the first channel 2254. The second DMS analyzer 2204 channel 2256 is fully isolated from the first and, accordingly, different transport gases may be introduced that contain some chemical agents (dopant/modifiers) which have an effect on conformation of protein ions. In addition, this design offers the possibility of changing the RF voltage Vrf (and consequently compensation voltage Vc) to manipulate protein conformation and selectively to direct new protein conformations into the MS 2206.

Computational Approaches

In one embodiment, software, e.g., CAChe software, provides for simulation of ion movement in a DMS. The software may reside within a processor such as, for example, in controller 242 of FIG. 2. The simulation software may provide for the calculation of protein conformation parameter (for example, minimum energy, polarization, effect of strong RF electric field on cross section), and theoretical models related to charge distribution in gas-phase system that are used to analyze experimental data from, for example, system 2200, and then relate the experimental data to projected protein conformations. The microDMx™ CAChe software, developed at SIONEX Corporation of Bedford, Mass., is capable of simulating any type of mobility-based analytical device. The simulation software may, for example, provide for the modulation of ion movement in a DMS analyzer under the effect of sufficient flow rate, strong RF voltages, and DC compensation voltages for some ions species which have different coefficient and alpha parameters as illustrated in FIGS. 2C-2H.

Molecular modeling calculations with CAChe software may enable an in-silico simulation of the mechanisms associated with the folding/unfolding of the proteins and the changes in their ion cross sectional area in a DMS such as DMS analyzer 2204. While providing data with strong support of the proposed mechanisms, the molecular modeling data may also demonstrate the potential for predicting changes in DMS separation for various compounds through the use of drift gas modifiers. Examples presenting correlation between experimental information obtained in DMS and molecular modeling calculations can be found in Levin et al., "*Characterization of gas phase interactions utilizing a novel* nanoelectrospray ionization-differential mobility-mass spectrometer (nanoESI-DMS-MS) system", Anal. Chem., 78, 96-106 (2006), the entire contents of which are incorporated herein by reference.

Experimental Approach—Model Protein Selection

In one embodiment, the system 2200 uses as a model of the protein δ-toxin (δ-hemolysin), a surface active protein produced by the bacteria Staphylococcus aureus. This is a small polypeptide of 26 amino acids and 5 kDa and serves as an excellent exemplary model. The polypeptide toxin causes damage to other cells via a number of factors including, the activation of membrane phospholipase $A_2$, stimulation of prostaglandin synthesis, inhibition of the binding of epidermal growth factor to cell surface receptors, release of lysozyme and δ-glucuronidase from neutrophil granules, formation of platelet activating factor via the activation of acetyltransferase and exertion of proinflammatory effects on account of its binding specificity to neutrophils and monocytes.

Figure 25:
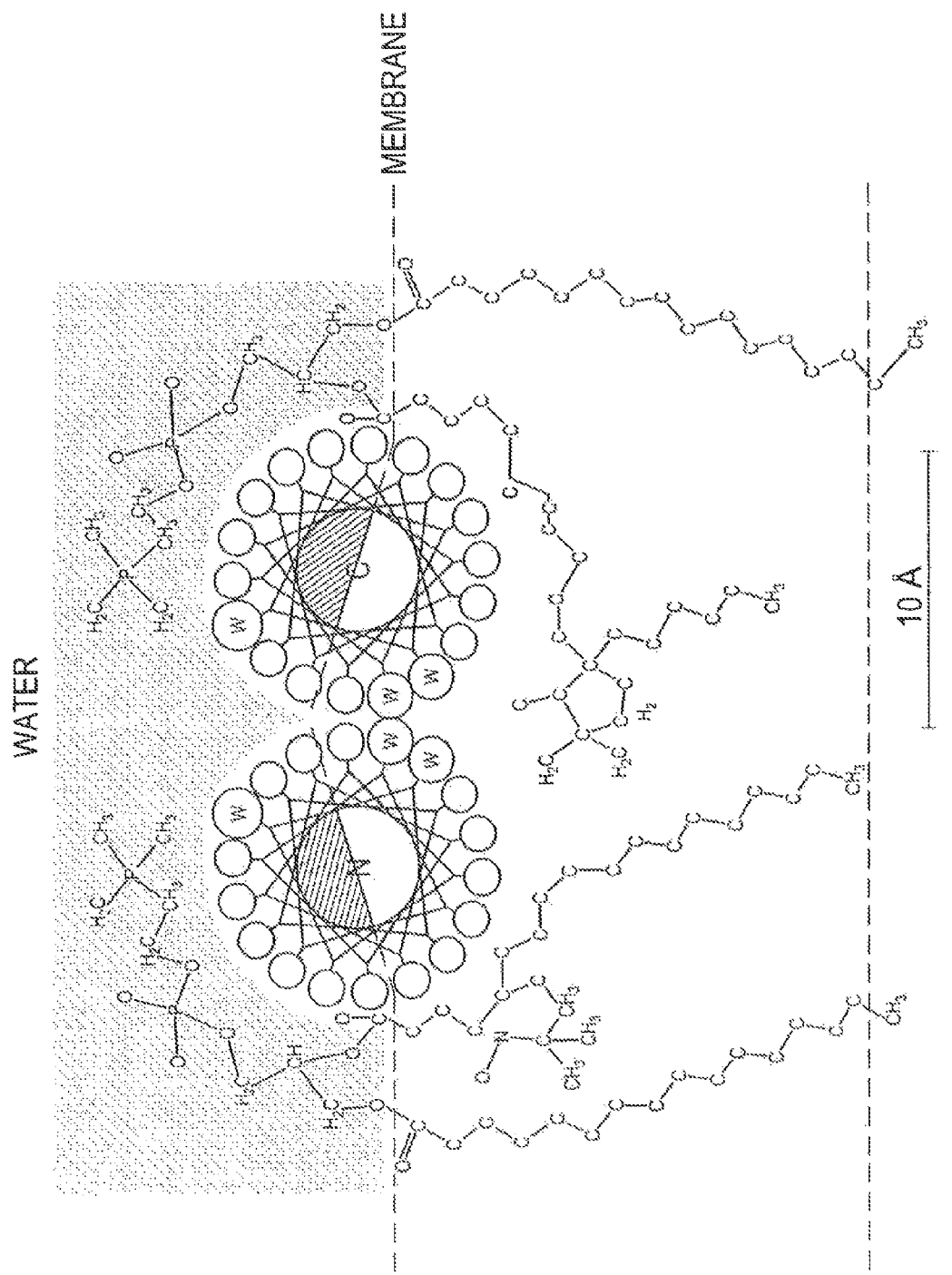
FIG. 25 shows a Polypeptide interaction with membranes where gray areas indicate the polar side of the helix.

FIG. 25 shows a Polypeptide interaction with membranes where gray areas indicate the polar side of the helix. Physical properties of the polypeptide such as solubility and surface activity suggest the formation of an amphiphilic helix upon binding to a lipid membrane, as shown in FIG. 25. FIG. 25 also illustrates the assumption of a helical conformation by the protein as it is surrounded by lipophilic long chain fatty acids. The helix formation has also been observed at high concentrations in water solutions, water/methanol mixtures, micelles or lipid vesicles.

Studies using saturated fatty acids suggest that δ-toxin activity may be controlled by the addition of saturated fatty acids and the effect on the activity is dependent on the chain length of the fatty acid. The ability of the protein to undergo conformational changes by assuming a helical structure upon interaction with lipophilic ligands makes it a good model for analysis based on the system 2200. In certain embodiments, the system 2200 enables the study of progressively larger protein targets of, for example without limitation, organophosphorous toxicants (e.g., nerve agents) such as acetylcholinesterase, arylformamidase and fatty acid amide hydrolase among others.

Sample Introduction

In certain embodiments, the system 2200 enables preparation of the protein sample in different pH conditions. In one embodiment, the system 2200 uses a physiological pH that is more representative of real life conditions. In addition, the system 2200 may use nano-electrospray conditions (flow rates of 50-200 mL/min) for introduction into the first DMS analyzer 2202 in order to minimize clustering, improve ionization efficiency and potentially ion suppression.

Figure 26:
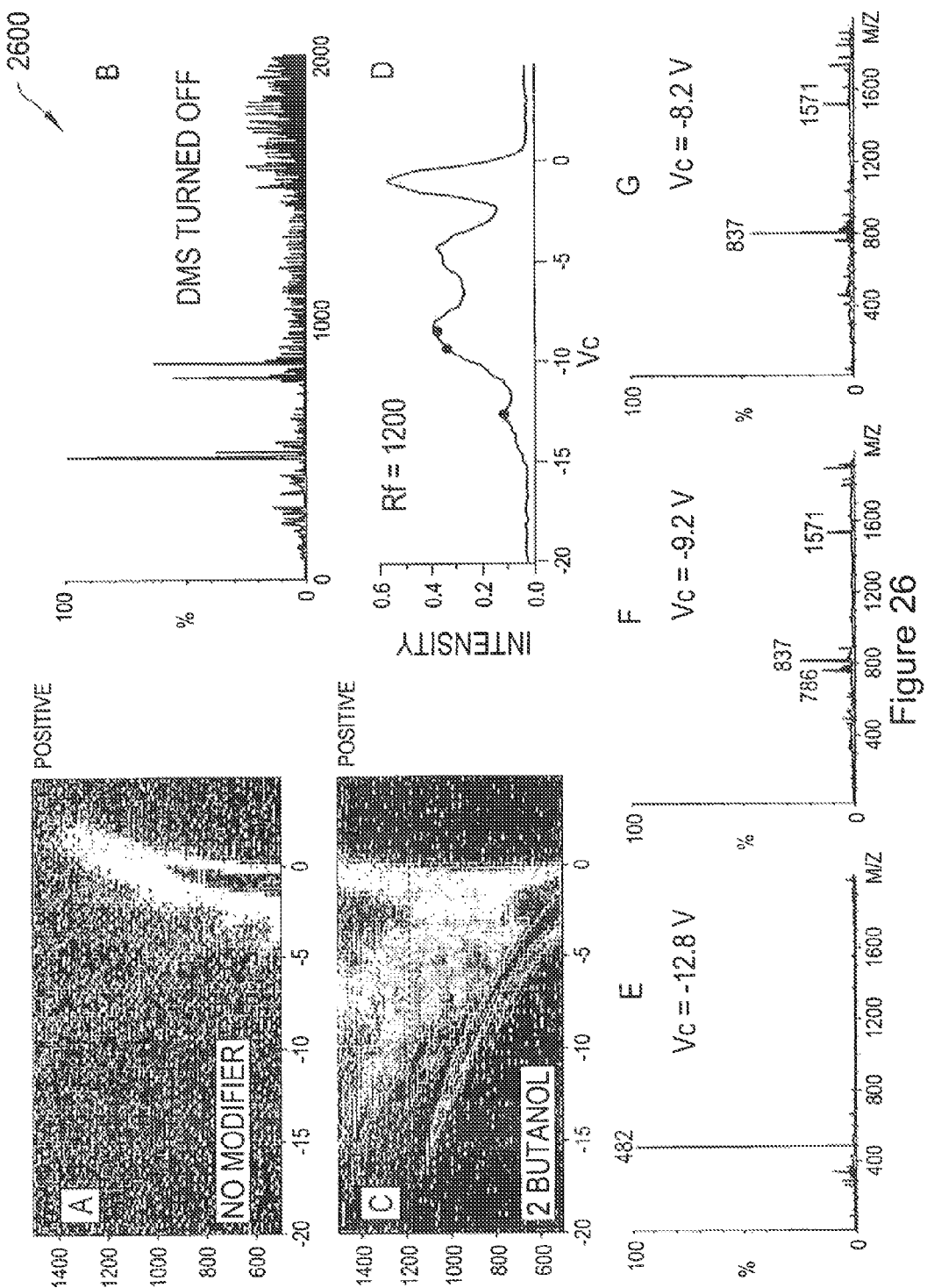
FIG. 26 shows various plots for 0.05 mg/ml each Angiotensin fragment 11-14, Glu-Fib B, and Neurotensin sample including DMS dispersion plots and collected mass spectra (DMS off) with no drift gas modifier (a & b) or for the same sample but with 8000 ppm 2-butanol according to an illustrative embodiment of the invention.

Techniques for Separation and Isolation of Conformers—Generation of Dispersion Plots FIG. 26 shows a combined plot 2600 for 0.05 mg/ml each Angiotensin fragment 11-14, Glu-Fib B, and Neurotensin sample including DMS dispersion plots and collected mass spectra (DMS off) with no drift gas modifier (a & b) or for the same sample but with 8000 ppm 2-butanol according to an illustrative embodiment of the invention. Following introduction of the protein sample into the first DMS analyzer 2202, one or more dispersion plots may be generated as illustrated in FIG. 26 that, for example, shows the separation of a mixture of three peptides angiotensin fragment ($[M+H]^+$ m/z 482); Glu-Fib B ($[M+2H]^{2+}$ m/z 786); and Neurotensin ($[M+2H]^{2+}$ m/z 837).

As shown in one exemplary operation according to FIG. 26, a drift gas modifier 2-Butanol, at a concentration of 8000 ppm, was used to enhance the differential mobility (DM) separation of the peptides. In the absence of the modifier (FIG. 26a), the DMS dispersion plot shows one main tract that consists of homo- and hetero-aggregate clusters of the peptides in the mixture. The Vc points used for the generation of the mass spectra in FIGS. 26e-f were selected based on Vc values determined to achieve optimum DM separation between the three peptide ions of interest. The results shown in FIG. 26 demonstrate that, with appropriate selection of drift gas modifier conditions, a DMS analyzer is capable of separating peptide ions of interest and, importantly, breaking up clusters. More particularly, FIG. 26 shows the resulting plots for 0.05 mg/ml each Angiotensin fragment 11-14, Glu-Fib B, and Neurotensin sample and collected mass spectra (DMS off) with no drift gas modifier (a & b). Figures c-g are for the same sample but with 8000 ppm 2-butanol, the DMS dispersion plot (c), DMS spectra, Rf=1200 (d), and selected Vc point mass spectra (normalized to same ion signal scale) for optimized separation of the three $MH^+$ ions, m/z 482 (e), m/z 786 (f), and m/z 837 (g).

Proteins selected according to Vc values in the DMS analyzer 2202 may be transferred to the DMS analyzer 2204 for further examination and manipulation as desired before submitting the ions to MS 2206 for detection and further analysis. Thus, in certain embodiments, the system 2200 uses dopants to provide an additional means for manipulation of protein conformations by breaking up intramolecular attraction forces (i.e., folded forms) and/or to expose or shield receptor sites to investigate selective affinity toward binding with ligands (e.g., chemical or biological agents).

Manipulation of Conformation by Modulation of RF Fields

Changes in the conformation of a molecule due to high temperature have been theoretically predicted and experimentally observed. In certain embodiments, the DMS analyzer 2204 may be controlled as to change the value of the RF voltage Vrf over a very broad range. The RF electric field in portions of the asymmetric waveform may reach values as high as 30,000 V/cm corresponding to effective temperatures well above kT. The strong RF field in the DMS analyzer 2202 and/or 2204 may create a relatively high temperature for ions due to the increasing kinetic energy of the ions, and consequently affect the ion conformation. This, in certain embodiments, enables the system 2200 to modify conformations and dipole moments of ion complexes. Hence, regulation of RF voltage Vrf may provide a precise control of the effective temperature (and conformation) of proteins.

Evaluation of Conformers Acting Via Protein/Ligand Interactions

Protein-drug binding greatly influences absorption, distribution, metabolism and excretion (ADME) properties of typical drugs and biological agents in general. Therefore, determining the binding characteristics of chemical agent with different protein conformations assists in screening for toxic candidates based on the selectivity for complex formation. To address such issues, a variety of affinity selection techniques may be employed by the system 2200 for screening ligands against protein receptors, based on the investigation of combinatorial libraries. In one embodiment, the system 2202 includes a data store, such as data store 244 of FIG. 2, that includes a library, list, and/or database of ligands. In at least one embodiment, the operation of the system 2200 adds a new dimension to the whole issue of protein/ligand interaction, not only in terms of high throughput but also in terms of the capability for further refinement of the screening for these processes by looking even at transient conformational intermediates.

Figure 27:
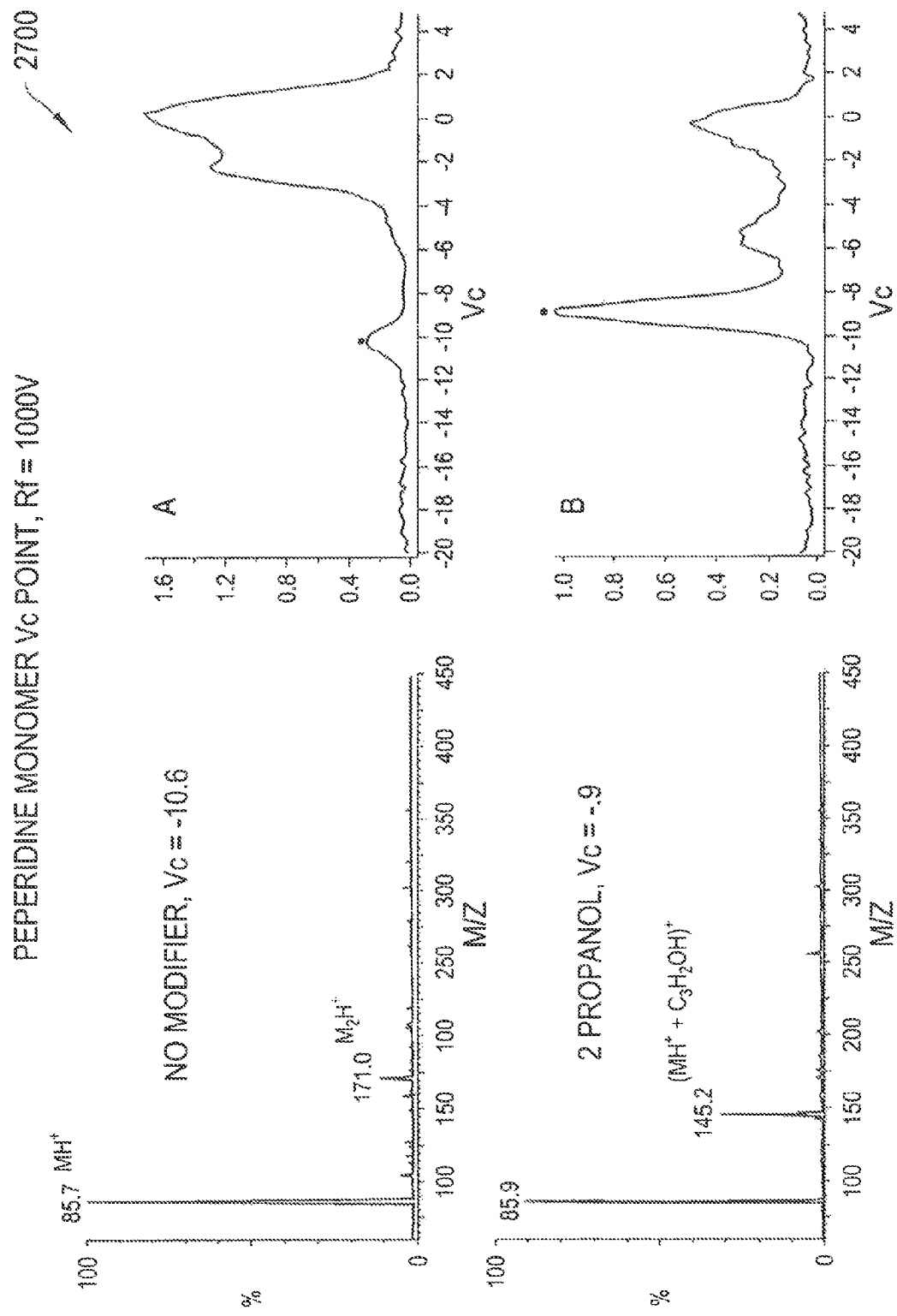
FIG. 27 shows the DMS spectra for piperidine at an Rf=1000 V with no modifier A and with 2-propanol modifier B according to an illustrative embodiment of the invention.

FIG. 27 shows a combined plot 2700 of the DMS spectra for piperidine at an Rf=1000 V with no modifier A and with 2-propanol modifier B according to an illustrative embodiment of the invention. More particularly, on the left are the collected mass spectra for the corresponding monomer Vc point (identified by blue circle in DMS spectra). Bottom table shows molecular modeling determined minimum conformation energy and surface volume values for piperidine dimer and 2-propanol adduct ions.

One important issue, in the context of the system 2200, is the ability of the system 2200 to selectively recognize and isolate conformational complexes and, to finally identify them in combination with mass spectrometry, e.g., MS 2206. The example combined plot 2700 demonstrates that the DMS analyzer 2204 of system 2200 possess this discriminatory power. Compared are the DMS spectra (generated from the DMS sensor electrometer plate ion signal, e.g., electrodes 2244 and/or 2246) for piperidine with and without the 2-propanol drift gas modifier at an RF voltage of 1000.

It is evident that the addition of the modifier produced a new piperidine monomer-modifier adduct ion (m/z 146), and resulted in a shift of the monomer Vc point to a lower value, reflecting an increase in the effective cross sectional area of the monomer ion equilibrium. In one embodiment, molecular modeling of global minimum conformation energy values were calculated for cluster ions of interest. The values determined for molecular interactions in vacuum provide direct comparison between cluster ion strength of formation. The global minimum conformation energy values for the piperidine dimer and piperidine-2-propanol adduct ion complexes are shown in the Table 4 below.

TABLE 4

Global Minimum Conformation Energy for Piperidine dimer and Piperidine-2 propanol

| | Minimum conformation energy (kcal/ml) | Surface volume |
|---|---|---|
| piperidine($H^+$)-piperidine | 6.3 | 7075 |
| piperidine($H^+$)-2-propanol | −16.1 | 6535 |

In one exemplary operation, a significant energy difference of 22.4 kcal/mol was observed between the two different complex ions. The lower minimum conformation energy value for the 2-propanol adduct ion complex indicates a greater strength of formation over that for the dimer ion. Under certain conditions it appears that the addition of the 2-propanol modifier resulted in an increase in the effective cross sectional area of the monomer ion equilibrium via changes in the participating ion equilibrium species (monomer, dimer, and 2-propanol adduct ions) and their degree of contribution to the equilibrium. Thus, the degree of ion contribution, based on strength of formation differences, appear to be a significant factor for the apparent increase in cross sectional area.

Under certain conditions, the binding of the ligands with the model protein selected has been known to result in complexes of distinct shape and, consequently cross sectional area, as discussed above. Accordingly, the demonstrated ability to separate such differently shaped molecular complexes based on shifts in the Vc point and differences in global minima energy values, provide criteria for comparison of selected protein by, for example, ligand interactions at least on a relative basis. In one embodiment, the system 2200 evaluates protein activity as a function of conformation by monitoring the complexation of δ-hemolysin with ligand libraries comprised of fatty acids of varying length (lipophilicity) and observing the changes in the DMS analyzer 2204.

Mass Spectrometric Analysis

During certain operational conditions, it may be important to identify the time frame associated with the generation of the spectral plots shown in FIG. 27. For example, the dispersion plots shown in FIGS. 27A and 27C may be generated manually where the process takes approximately 1 minute. In one embodiment, the dispersion plots are generated automatically under the control of a processor and/or controller such as controller 242 of FIG. 2. However, after the dispersion plot has been established, for any given RF or Vrf value, a conformer band may be isolated in matter of milliseconds and manipulated for transfer to DMS analyzer 2204 and/or MS 2206. Moreover, the complete Vc spectra for a selected Vrf value may be scanned in less than 5 seconds. Effectively, in certain embodiments, the limiting factor for data acquisition is the MS 2206 as far as the rate of data acquisition is concerned. Accordingly, mass spectrometric analyses may be conducted using a quadrupole time of flight MS which provides rapid scanning mode and also relatively high resolution (M/ΔM ~7,000).

It will be apparent to those of ordinary skill in the art that certain algorithms and methods involved in the present invention may be embodied in a computer program product that includes a computer usable and/or readable medium. For example, such a computer usable medium may consist of a read only memory device, such as a CD ROM disk or conventional ROM devices, or a random access memory, such as a hard drive device or a computer diskette, having a computer readable program code stored thereon.

While this invention has been particularly shown and described with references to preferred embodiments thereof, it will be understood by those skilled in the art that various changes in form and details may be made therein without departing from the scope of the invention encompassed by the appended claims.

What is claimed is:

1. A sample analysis system comprising,
   a DMS analyzer for i) receiving ion species, ii) affecting a non-transient alteration of the conformation including physical or chemical properties of the ion species, and iii) passing through a conformer of the ion species, and
   a controller for controlling at least one condition of the DMS analyzer to alter the conformation of the ion species, wherein the at least one condition includes at least one of an amount of a ligand and a type of ligand.

2. The system of claim 1 comprising a data store for storing a library of ligands, the controller configured to control the introduction of an amount of ligand listed in the library.

3. The system of claim 2, wherein the controller introduces each of a set of ligands into the DMS analyzer to adjust the conformation of the ion species in relation to each ligand.

4. The system of claim 3, wherein the controller introduces each ligand sequentially.

5. The system of claim 1, comprising a detector for receiving and detecting the conformer of the ion species.

6. The system of claim 5, wherein the detector includes a mass spectrometer.

7. The system of claim 6, wherein the mass spectrometer includes a time-of-flight mass spectrometer.

* * * * *